(12) United States Patent
Laudenslager et al.

(10) Patent No.: US 11,730,929 B2
(45) Date of Patent: Aug. 22, 2023

(54) METHODS AND DEVICES FOR TREATMENT OF STENOSIS OF ARTERIOVENOUS FISTULA SHUNTS

(71) Applicant: Ra Medical Systems, Inc., Carlsbad, CA (US)

(72) Inventors: James B. Laudenslager, San Marcos, CA (US); Dean S. Irwin, Carlsbad, CA (US)

(*) Notice: Subject to any disclaimer, the term of this patent is extended or adjusted under 35 U.S.C. 154(b) by 252 days.

(21) Appl. No.: 17/246,265

(22) Filed: Apr. 30, 2021

(65) Prior Publication Data

US 2021/0252258 A1 Aug. 19, 2021

Related U.S. Application Data

(60) Continuation of application No. 16/502,766, filed on Jul. 3, 2019, now Pat. No. 11,020,570, which is a
(Continued)

(51) Int. Cl.
| | |
|---|---|
| *A61M 25/09* | (2006.01) |
| *A61B 18/24* | (2006.01) |
| *A61M 25/00* | (2006.01) |
| *A61B 18/00* | (2006.01) |
| *A61M 25/10* | (2013.01) |
| *A61B 18/22* | (2006.01) |
| *A61M 25/01* | (2006.01) |
| *A61B 50/30* | (2016.01) |

(Continued)

(52) U.S. Cl.
CPC .......... *A61M 25/09* (2013.01); *A61B 18/245* (2013.01); *A61B 50/30* (2016.02); *A61B 2018/0041* (2013.01); *A61B 2018/00285* (2013.01); *A61B 2018/00577* (2013.01); *A61B 2018/206* (2013.01); *A61B 2018/2222* (2013.01); *A61B 2018/2238* (2013.01); *A61B 2050/314* (2016.02); *A61B 2090/3966* (2016.02); *A61M 25/002* (2013.01); *A61M 2025/0177* (2013.01); *A61M 2025/105* (2013.01)

(58) Field of Classification Search
None
See application file for complete search history.

(56) References Cited

U.S. PATENT DOCUMENTS

| | | |
|---|---|---|
| 3,740,113 A | 6/1973 | Cass |
| 3,995,934 A | 12/1976 | Nath |

(Continued)

FOREIGN PATENT DOCUMENTS

| | | |
|---|---|---|
| CN | 1652722 A | 8/2005 |
| CN | 1832708 A | 9/2006 |

(Continued)

OTHER PUBLICATIONS

"Prevalence and Cost of ESRD Therapy," USRDS Annual Data Report 1991, American Journal of Kidney Diseases, vol. 18, No. 3, Suppl 2, (Nov. 1991); pp. 21-29.

(Continued)

*Primary Examiner* — Manuel A Mendez

(57) ABSTRACT

Devices and methods are discussed directed to the use of a low profile laser ablation catheter for use in laser ablation removal of arterial plaque blockages to restore blood flow in the treatment of arteriovenous fistulas. Also discussed are devices and methods directed to packaging, long term storage and sterilization of liquid core ablation catheters.

9 Claims, 39 Drawing Sheets

Related U.S. Application Data continuation of application No. 15/723,062, filed on Oct. 2, 2017, now Pat. No. 10,384,038, which is a division of application No. 14/515,435, filed on Oct. 15, 2014, now Pat. No. 9,962,527.

(60) Provisional application No. 61/891,830, filed on Oct. 16, 2013.

(51) Int. Cl.
*A61B 90/00* (2016.01)
*A61B 18/20* (2006.01)

(56) References Cited

U.S. PATENT DOCUMENTS

| | | |
|---|---|---|
| 4,009,382 A | 2/1977 | Nath |
| 4,045,119 A | 8/1977 | Eastgate |
| 4,380,460 A | 4/1983 | Otstot et al. |
| 4,516,972 A | 5/1985 | Samson et al. |
| 4,530,569 A | 7/1985 | Squire |
| 4,641,912 A | 2/1987 | Goldenberg |
| 4,686,979 A | 8/1987 | Gruen et al. |
| 4,720,166 A | 1/1988 | Ohmori et al. |
| 4,732,448 A | 3/1988 | Goldenberg |
| 4,739,768 A | 4/1988 | Engleson |
| 4,747,405 A | 5/1988 | Leckrone |
| 4,747,662 A | 5/1988 | Fitz |
| 4,762,129 A | 8/1988 | Bonzel |
| 4,770,653 A | 9/1988 | Shturman |
| 4,784,132 A | 11/1988 | Fox et al. |
| 4,784,135 A | 11/1988 | Blum et al. |
| 4,793,359 A | 12/1988 | Sharrow |
| 4,799,754 A | 1/1989 | Goldenberg |
| 4,800,876 A | 1/1989 | Fox et al. |
| 4,834,093 A | 5/1989 | Littleford et al. |
| 4,844,062 A | 7/1989 | Wells |
| 4,848,336 A | 7/1989 | Fox et al. |
| 4,850,351 A | 7/1989 | Herman et al. |
| 4,862,886 A | 9/1989 | Clarke et al. |
| 4,907,133 A | 3/1990 | Nath |
| 4,913,142 A | 4/1990 | Kittrell et al. |
| 4,919,508 A | 4/1990 | Grace et al. |
| 4,927,231 A | 5/1990 | Levatter |
| 4,930,863 A | 6/1990 | Croitoriu et al. |
| 4,998,794 A | 3/1991 | Holzman |
| 5,005,944 A | 4/1991 | Laakmann et al. |
| 5,037,404 A | 8/1991 | Gold et al. |
| 5,040,548 A | 8/1991 | Yock |
| 5,041,108 A | 8/1991 | Fox et al. |
| 5,061,273 A | 10/1991 | Yock |
| 5,076,659 A | 12/1991 | Bekiarian et al. |
| 5,100,388 A | 3/1992 | Behl et al. |
| 5,157,750 A | 10/1992 | Grace et al. |
| 5,165,773 A | 11/1992 | Nath |
| 5,176,674 A | 1/1993 | Hofmann |
| 5,188,632 A | 2/1993 | Goldenberg |
| 5,263,952 A | 11/1993 | Grace et al. |
| 5,267,341 A | 11/1993 | Shearin |
| 5,267,993 A | 12/1993 | Grace et al. |
| 5,290,277 A | 3/1994 | Vercimak et al. |
| 5,304,171 A | 4/1994 | Gregory et al. |
| 5,321,783 A | 6/1994 | Nielson et al. |
| 5,350,395 A | 9/1994 | Yock |
| 5,374,266 A | 12/1994 | Kataoka et al. |
| 5,395,361 A | 3/1995 | Fox et al. |
| 5,412,750 A | 5/1995 | Nath |
| 5,419,760 A | 5/1995 | Narcisco, Jr. |
| 5,429,604 A | 7/1995 | Hammersmark et al. |
| 5,429,617 A | 7/1995 | Hammersmark et al. |
| 5,438,873 A | 8/1995 | Wlodarczyk et al. |
| 5,456,680 A | 10/1995 | Taylor et al. |
| 5,484,433 A | 1/1996 | Taylor et al. |
| 5,497,441 A | 3/1996 | Croitoru et al. |
| 5,514,128 A | 5/1996 | Hillsman et al. |
| 5,573,531 A | 11/1996 | Gregory |
| 5,584,558 A | 12/1996 | Nath |
| 5,675,689 A | 10/1997 | Nath |
| 5,722,972 A | 3/1998 | Power |
| 5,737,473 A | 4/1998 | Nath |
| 5,836,940 A | 11/1998 | Gregory |
| 5,857,052 A | 1/1999 | Nath |
| 5,868,665 A | 2/1999 | Biggs |
| 5,976,093 A | 11/1999 | Jang |
| 5,989,243 A | 11/1999 | Goldenberg |
| 6,022,309 A | 2/2000 | Celliers et al. |
| 6,106,510 A | 8/2000 | Lunn et al. |
| 6,117,128 A | 9/2000 | Gregory |
| 6,143,013 A | 11/2000 | Samson et al. |
| 6,163,641 A | 12/2000 | Eastgate |
| 6,165,163 A | 12/2000 | Chien et al. |
| 6,212,422 B1 | 4/2001 | Berg et al. |
| 6,263,236 B1 | 7/2001 | Kasinkas et al. |
| 6,306,124 B1 | 10/2001 | Jones et al. |
| 6,314,226 B1 | 11/2001 | Nath |
| 6,314,227 B1 | 11/2001 | Nath |
| 6,368,318 B1 | 4/2002 | Visuri et al. |
| 6,418,257 B1 | 7/2002 | Nath |
| 6,507,688 B1 | 1/2003 | Nath |
| 6,520,934 B1 | 2/2003 | Lee et al. |
| 6,571,049 B1 | 5/2003 | Nath |
| 6,585,760 B1 | 7/2003 | Fogarty |
| 6,609,014 B1 | 8/2003 | Allison et al. |
| 6,824,553 B1 | 11/2004 | Samson et al. |
| 6,893,427 B1 | 5/2005 | Jimenez |
| 6,963,688 B2 | 11/2005 | Nath |
| 6,974,473 B2 | 12/2005 | Barclay et al. |
| 7,050,692 B2 | 5/2006 | Harlen et al. |
| 7,144,248 B2 | 12/2006 | Irwin |
| 7,144,381 B2 | 12/2006 | Gertner |
| 7,167,622 B2 | 1/2007 | Temelkuran et al. |
| 7,402,151 B2 | 7/2008 | Rosenman et al. |
| 7,572,254 B2 | 8/2009 | Herbert et al. |
| 7,762,980 B2 | 7/2010 | Gertner |
| 8,152,795 B2 | 4/2012 | Farr et al. |
| 8,231,551 B2 | 7/2012 | Griffin et al. |
| 8,652,084 B2 | 2/2014 | Akingba |
| 9,339,628 B2 | 5/2016 | Adams et al. |
| 9,700,655 B2 | 7/2017 | Laudenslager et al. |
| 9,962,527 B2 | 5/2018 | Laudenslager et al. |
| 10,384,038 B2 | 8/2019 | Laudenslager et al. |
| 10,478,251 B2 | 11/2019 | Shuffler et al. |
| 10,485,613 B2 | 11/2019 | Hendrick et al. |
| 10,492,876 B2 | 12/2019 | Anastassiou et al. |
| 10,555,772 B2 | 2/2020 | Laudenslager et al. |
| 10,799,671 B2 | 10/2020 | Shimada et al. |
| 2003/0023236 A1 | 1/2003 | Ashok et al. |
| 2003/0078569 A1 | 4/2003 | Caldera et al. |
| 2003/0158561 A1 | 8/2003 | Kanesaka |
| 2004/0220473 A1 | 10/2004 | Lauldi |
| 2005/0031281 A1 | 2/2005 | Nath |
| 2005/0234436 A1 | 10/2005 | Baxter et al. |
| 2005/0254237 A1 | 11/2005 | Nath et al. |
| 2006/0253048 A1 | 11/2006 | Jones et al. |
| 2006/0271090 A1 | 11/2006 | Shaked et al. |
| 2007/0244495 A1 | 10/2007 | Kwon |
| 2008/0188793 A1 | 8/2008 | Kozak et al. |
| 2008/0249515 A1 | 10/2008 | Taylor |
| 2009/0112198 A1 | 4/2009 | Khanna et al. |
| 2009/0163899 A1 | 6/2009 | Burton et al. |
| 2009/0254074 A1 | 10/2009 | Splinter et al. |
| 2009/0264898 A1 | 10/2009 | Miller et al. |
| 2009/0299354 A1 | 12/2009 | Melsky et al. |
| 2010/0004607 A1 | 1/2010 | Wilson et al. |
| 2010/0016842 A1 | 1/2010 | Fix |
| 2010/0087783 A1 | 4/2010 | Weber et al. |
| 2010/0114081 A1 | 5/2010 | Keeler et al. |
| 2010/0152720 A1 | 6/2010 | Sauro et al. |
| 2010/0198193 A1 | 8/2010 | Trapp |
| 2011/0238041 A1 | 9/2011 | Lim et al. |
| 2012/0277671 A1 | 11/2012 | Fuentes |
| 2013/0096545 A1 | 4/2013 | Laudenslager et al. |
| 2015/0057639 A1 | 2/2015 | Storbeck et al. |
| 2015/0105714 A1 | 4/2015 | Laudenslager et al. |

(56) References Cited

U.S. PATENT DOCUMENTS

| | | |
|---|---|---|
| 2017/0143424 A1 | 5/2017 | Laudenslager et al. |
| 2017/0266351 A1 | 9/2017 | Laudenslager et al. |
| 2018/0008348 A1 | 1/2018 | Grace et al. |
| 2018/0021550 A1 | 1/2018 | Laudenslager et al. |
| 2018/0021551 A1 | 1/2018 | Laudenslager et al. |
| 2018/0021552 A1 | 1/2018 | Laudenslager et al. |
| 2018/0250498 A1 | 9/2018 | Stern et al. |
| 2019/0142517 A1 | 5/2019 | Chia et al. |
| 2019/0160259 A1 | 5/2019 | Cottone et al. |
| 2019/0290356 A1 | 9/2019 | Wood et al. |
| 2019/0366036 A1 | 12/2019 | Jalgaonkar et al. |
| 2020/0046429 A1 | 2/2020 | Tschida et al. |
| 2020/0230294 A1 | 7/2020 | Laudenslager et al. |
| 2020/0261154 A1 | 8/2020 | Ogata et al. |

FOREIGN PATENT DOCUMENTS

| | | |
|---|---|---|
| EP | 0247746 | 12/1987 |
| EP | 0368512 | 5/1990 |
| EP | 0590268 | 4/1994 |
| EP | 0727054 | 10/1994 |
| EP | 1757428 | 2/2007 |
| EP | 2301617 | 3/2011 |
| WO | WO 95/12138 | 5/1995 |
| WO | WO 97/039691 | 10/1997 |
| WO | WO 98/38538 | 9/1998 |
| WO | WO 00/30696 | 2/2000 |
| WO | WO 09/120871 | 10/2009 |

OTHER PUBLICATIONS

Bittl; Catheter Interventions for Hemodiaylysis Fistula and Grafts: J Am Coll Cardiol Intv vol. 3 pp. 1-11 (2010).

Das, "Excimer Laser-Assisted Angioplasty for Infrainguinal Artery Disease" J of Endovasc Therapy vol. 16 pp. 1198-11104(2009).

Drooz, "Ultrahigh-pressure angioplasty of a transposed brachiocephalic fistula with recurrent stenosis," ConQuest PTA Dilation Catheter, Bard Peripheral Vascular, Innova Fairfax Hospital; Fairfax Hospital, Aug. 2005.

Forauer, Hoffer, et al.; "Dialysis Access Venous Stenoses: Treatment with Balloon Angioplasty-1—versus 3-minute Inflation Times" Radiology vol. 249, pp. 375-381 (2008).

Gandini and Del Giudice; "Use of laser Atherectomy with drug-eluting balloon angioplasty shows benefit in treatment of in-stent restenosis" presented at EuroPCR 2014 Congress (May 20-23, 2014).

Haage, Verwerk et al.:"Percutaneous treatment of thrombosed primary arteriovenous hemodialysis access fistulae" Kidney International, vol. 57, pp. 1169-1175(2000).

Hamburger et al., New Aspects of Excimer Laser Coronary Angioplasty Physical Aspects and Clinical Results, printed by Optima Grafische Communicatie ISBN 90-73235-27-8, Rotterdam, Jaap N. Hamburger, Dec. 1998.

Hofstra et al., "Enhanced Cellular Proliferation in Intact Stenotic Lesions Derived From Human Arteriovenous Fistulas and peripheral Bypass Grafts. Does it correlate with Flow Parameters?" Circulation, 1996;94:1283-1290.

Janis et al. "Laser Thrombolysis in an in vitro Model" Lasers in Surg.: Advanced Characterization, Therapeutics and Systems, Pro. of SPIE vol. 3907 pp. 582-585 (2000).

Ma et al., "Interaction of excimer laser with blood components and thrombosis" Life Science J. vol. 5 pp. 19-26 (2008).

Mickley; "Stenosis and thrombus in hemodialysis fistula and grafts: the surgeon's point of view" Nephrol Dial Transplant vol. 19 pp. 309-311 (2001).

Miller and Friedman, "Balloon-Assisted Maturation of Arteriovenous Fistulas" Endovascular Today Endovascular Today, pp. 46-54 (2010).

Morph® "Universal Deflectable Guide Catheder," BioCardia® Cat # 01037-5.

Mysliwiec, "Vascular access thrombosis—what are the possibilities of intervention?" Nephrol Dial Transplant (1997) 12: Editorial Comments.

Ozkan, Gungor et al. "Endovascular Stent Placement of Juxtaanastomotic Stenosis in Native Arteriovenus Fistula After Unsuccessful Balloon Angioplasty" Iranian J of Radiology, vol. 10 pp. 133-139 (2013).

Papaioannou et al. "Excimer Laser Assisted Thrombolysis: The Effect of Fluence, Repetition Rate and Catheter Size" Proc. SPIE 4609, Lasers in Surgery; Advanced Characterization, Therapeutics and Systems XII 413 (2002).

Papaioannou et al. "Particulate debris analysis during excimer laser thrombolysis: An in-vitro study" Proc. SPIE 4609, Lasers in Surgery; Advanced Characterization, Therapeutics and Systems XII 404 (2002).

Shenoy, "Surgical anatomy of upper arm: what is needed for AVF planning" J of Vascul Access vol. 10 pp. 223-232(2009).

Sofocleous et al.;"Dialysis Fistulas" in Medscape (2013).

Staniloae et al. "Obrital Atherectomy: Device Evolution and Clinical Data" Periperal Vasc. Disease, vol. 26,pp. 215-219 (2014).

Van den Berg, Pedrotti et al.; "In-Stent Restenosis: Mid-Term Results of Debulking Using Excimer Laser and Drug-Eluting Balloons: Sustained Benefit?" J Invasive Cardiol vol. 26 pp. 333-337(2014).

Van den Berg; "Atherectomy and DCB in the SFA: A Summary of the Data" Endovascular Today pp. 28-32(2014).

Walker et al., "Excimer Laser-Assisted Angioplasty" Endovasc. Today ,pp. 75-76 (2007).

Zaleski; "Declotting, Maintenance, and Avoiding Procedural Complications of Native Arteriovenous Fistulae" Semin Intervent Radiol. vol. 21, pp. 83-93 (2004).

Zwaan et al., "Initial clinical experience with a new pulsed dye laser device in angioplasty of limb ischemia and shunt fistula obstructions," European Journal of Radiology, 14 (1992) pp. 72-76.

Extended European Search Report dated May 29, 2015 in European Patent Application No. EP 12840010.8, filed: Oct. 12, 2012.

International Preliminary Report on Patentability dated Apr. 24, 2014 in International Application No. PCT/US2012/060065 filed Oct. 12, 2012.

International Search Report and Written Opinion dated Mar. 29, 2013 in International Application No. PCT/US2012/060065 filed Oct. 12, 2012.

Notice of Allowance dated Apr. 20, 2017 in U.S. Appl. No. 13/651,070, filed Oct. 12, 2012 and published as: US-2013/0096545 on: Apr. 18, 2013 and now U.S. Pat. No. 9,700,655 on Jul. 11, 2017.

Final Office Action dated Sep. 15, 2016 in U.S. Appl. No. 13/651,070, filed Oct. 12, 2012 and published as: US-2013/0096545 on: Apr. 18, 2013 and now U.S. Pat. No. 9,700,655 on Jul. 11, 2017.

Non-Final Office Action dated Feb. 12, 2016 in U.S. Appl. No. 13/651,070, filed Oct. 12, 2012 and published as: US-2013/0096545 on: Apr. 18, 2013 and now U.S. Pat. No. 9,700,655 on Jul. 11, 2017.

Notice of Allowance dated Jan. 30, 2018 in U.S. Appl. No. 14/515,435, filed Oct. 15, 2014, published as: 2015/0105714 on Apr. 16, 2015 and now U.S. Pat. No. 9,962,527 on May 8, 2018.

ExParte Quayle Action dated: Dec. 12, 2017 in U.S. Appl. No. 14/515,435, filed Oct. 15, 2014, published as: 2015/0105714 on Apr. 16, 2015 and now U.S. Pat. No. 9,962,527 on May 8, 2018.

Notice of Allowance dated Apr. 19, 2019 in U.S. Appl. No. 15/723,062, filed Oct. 2, 2017, published as: 2018/0021551 on Jan. 25, 2018.

Non Final Office Action dated Dec. 31, 2018 in U.S. Appl. No. 15/723,062, filed Oct. 2, 2017, published as: 2018/0021551 on Jan. 25, 2018.

Non Final Office Action dated Nov. 30, 2018 in U.S. Appl. No. 15/723,057, filed Oct. 2, 2017, published as: 2018/0021550 on Jan. 25, 2018 and now U.S. Pat. No. 10,245,417 on Apr. 2, 2019.

Notice of Allowance dated Dec. 31, 2018 in U.S. Appl. No. 15/723,057, filed Oct. 2, 2017, published as: 2018/0021550 on Jan. 25, 2018 and now U.S. Pat. No. 10,245,417 on Apr. 2, 2019.

Notice of Allowance dated Feb. 26, 2019 in U.S. Appl. No. 15/723,057, filed Oct. 2, 2017, published as: 2018/0021550 on Jan. 25, 2018 and now U.S. Pat. No. 10,245,417 on Apr. 2, 2019.

(56) References Cited

OTHER PUBLICATIONS

Notice of Allowance dated Apr. 17, 2019 in U.S. Appl. No. 15/723,067, filed Oct. 2, 2017, published as: 2018/0021552 on Jan. 25, 2018.
Notice of Allowance dated Feb. 27, 2019 in U.S. Appl. No. 15/723,067, filed Oct. 2, 2017, published as: 2018/0021552 on Jan. 25, 2018.
ExParte Quayle Action dated: Nov. 29, 2018 in U.S. Appl. No. 15/723,067, filed Oct. 2, 2017, published as: 2018/0021552 on Jan. 25, 2018.
Extended European Search Report dated Aug. 13, 2019 in European Patent Application No. EP 19163464.1, filed: Mar. 18, 2019.
Notice of Allowance dated Oct. 17, 2019 in U.S. Appl. No. 15/359,412, filed Nov. 22, 2016, published as: 2017/0143424 on May 25, 2017.
Non-Final Office Action dated Aug. 5, 2019 in U.S. Appl. No. 15/359,412, filed Nov. 22, 2016, published as: 2017/0143424 on May 25, 2017.
Non-Final Office Action dated Sep. 30, 2020 in U.S. Appl. No. 16/502,766, filed Jul. 3, 2019 and published as: US-2019/0336732 on: Nov. 7, 2019.
Notice of Allowance dated Feb. 1, 2021 in U.S. Appl. No. 16/502,766, filed Jul. 3, 2019 and published as: US-2019/0336732 on: Nov. 7, 2019.
Non-Final Office Action dated Jan. 12, 2021 in U.S. Appl. No. 16/359,889, filed Mar. 20, 2019 and published as: US-2019/0290356 on: Sep. 26, 2019.
Invitation to Pay Additional Fees, dated Apr. 29, 2021 in International Patent Application No. PCT/US2021/019199 filed: Feb. 23, 2021.
Notice of Allowance dated Jun. 17, 2021 in U.S. Appl. No. 16/359,889, filed Mar. 20, 2019.
International Search Report and Written Opinion dated Jul. 12, 2021 in International Patent Application: PCT/US21/19199 filed Feb. 21, 2021.
Non-Final Office Action dated Aug. 24, 2022 in U.S. Appl. No. 17/028,910, filed Sep. 22, 2020 and published as: 2021/0015978 on Jan. 21, 2021.
Non-Final Office Action dated Mar. 10, 2022 in U.S. Appl. No. 16/843,736, filed Apr. 8, 2020 and published as: 2020/0230294 on Jul. 23, 2020.
Final Office Action dated Dec. 27, 2022, in U.S. Appl. No. 17/028,910, filed Sep. 22, 2020 and published as: 2021/0015978 on Jan. 21, 2021.
Non-Final Office Action dated Oct. 13, 2021 in U.S. Appl. No. 16/843,736, filed Apr. 8, 2020 and published as: 2020/0230294 on Jul. 23, 2020.

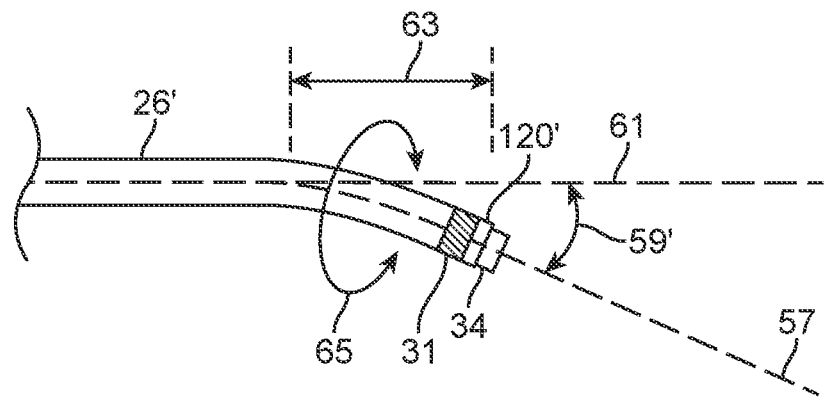
FIG. 22
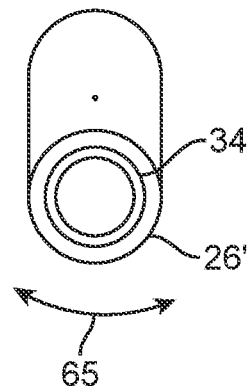
FIG. 23
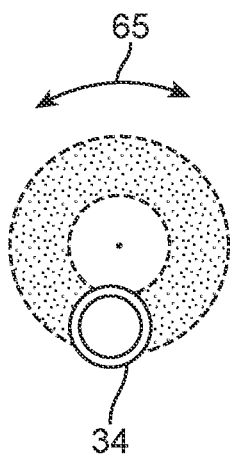 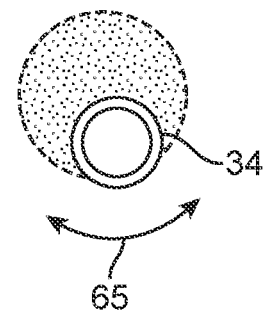
FIG. 24　　　　　　FIG. 25

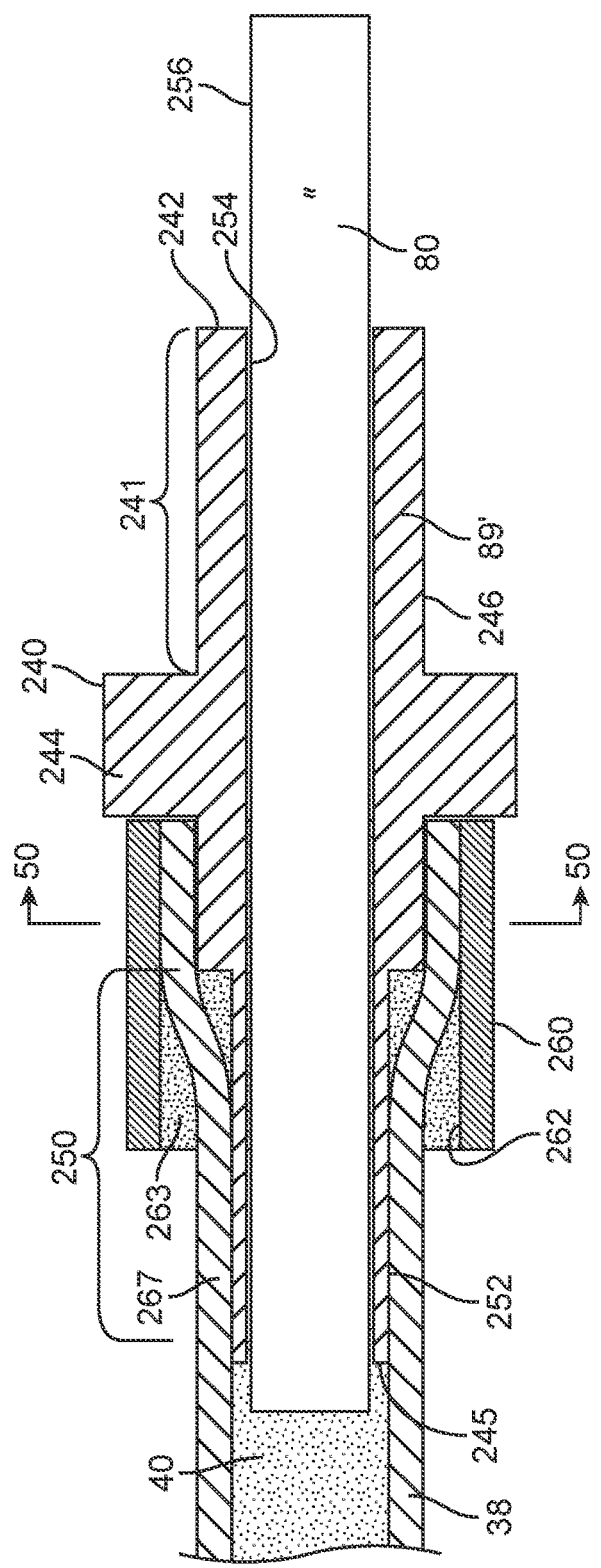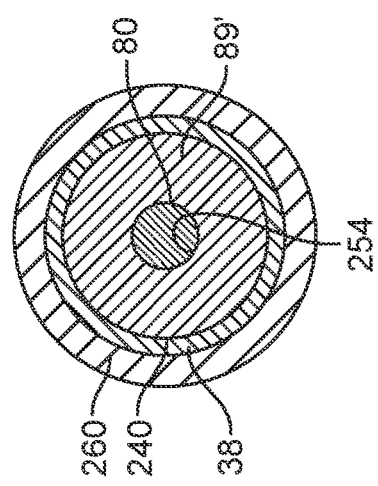
FIG. 49
FIG. 50

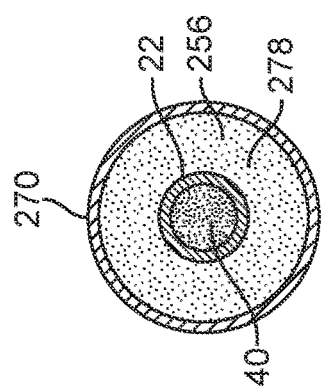
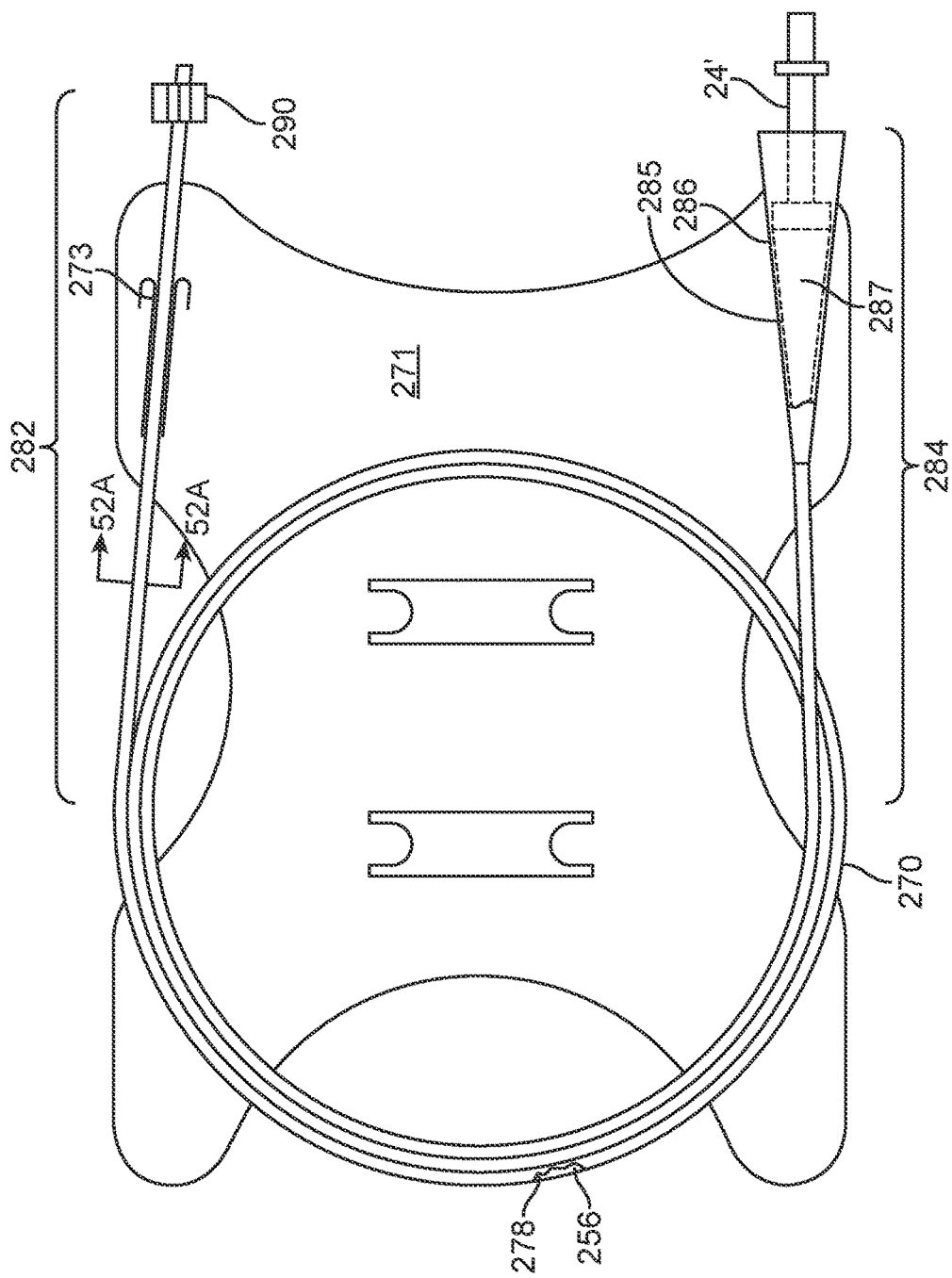

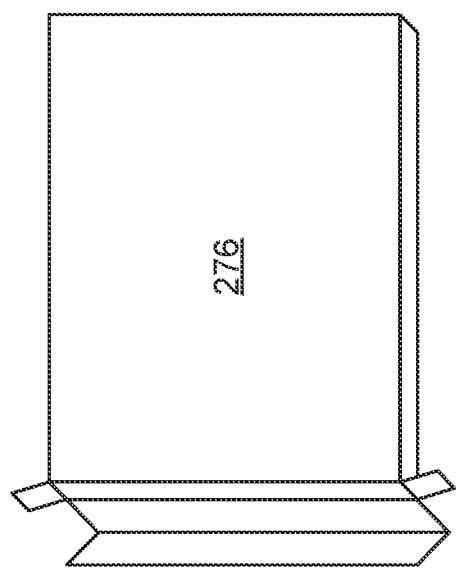
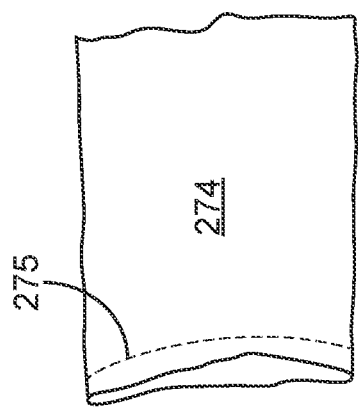
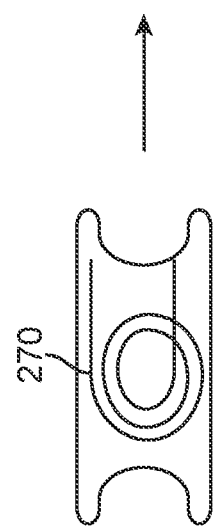
FIG. 53
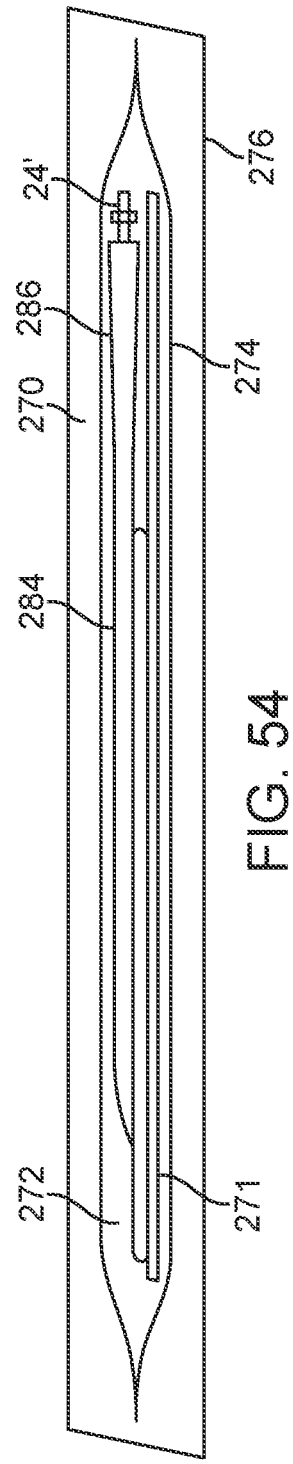
FIG. 54

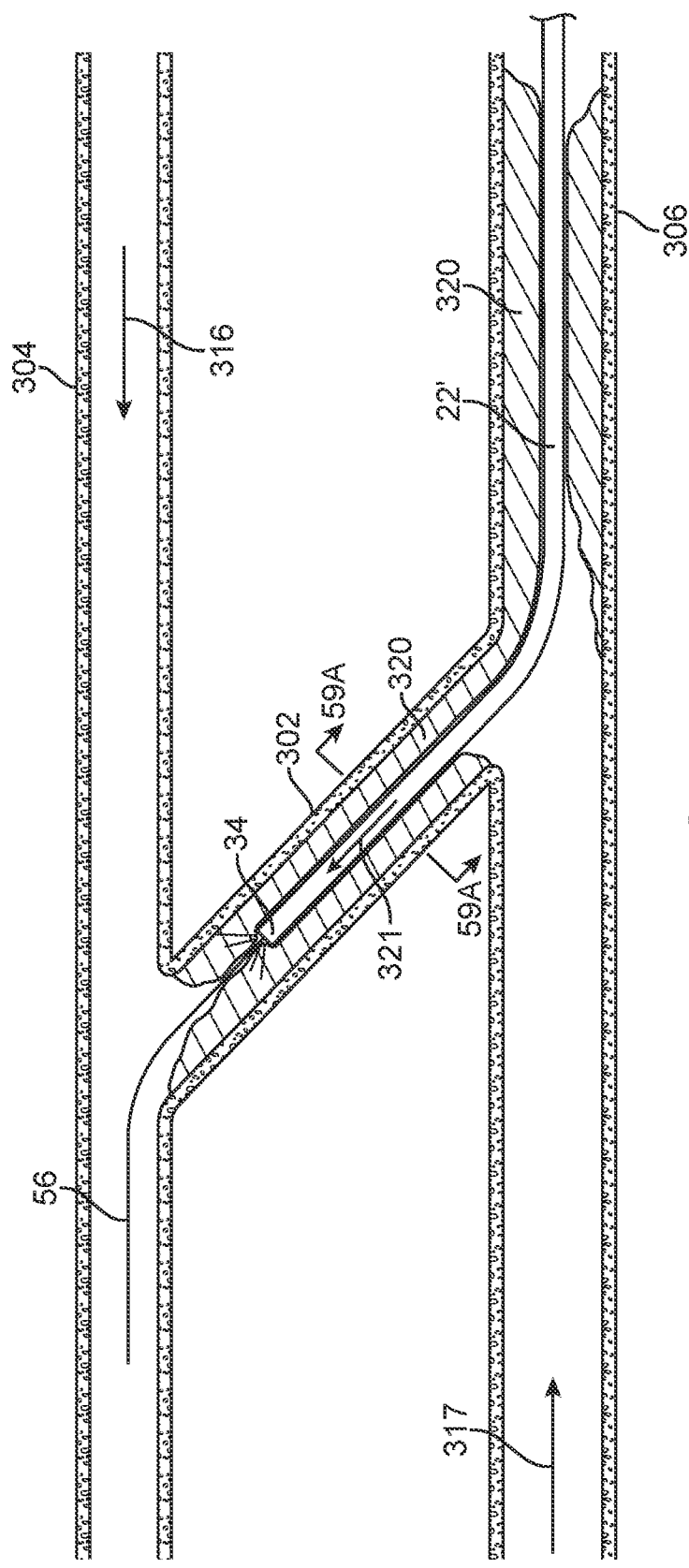
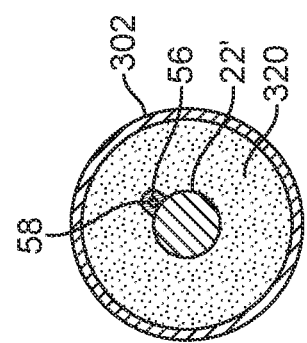
FIG. 59
FIG. 59A

METHODS AND DEVICES FOR TREATMENT OF STENOSIS OF ARTERIOVENOUS FISTULA SHUNTS

RELATED APPLICATIONS

This application is a continuation of U.S. patent application Ser. No. 16/502,766, Filed Jul. 3, 2019, by J. Laudenslager et al., titled "Methods and Devices for Treatment of Stenosis of Arteriovenous Fistula Shunts", which is a continuation of U.S. patent application Ser. No. 15/723,062, Filed Oct. 2, 2017, by J. Laudenslager et al, titled "Methods and Devices for Treatment of Stenosis of Arteriovenous Fistula Shunts", now U.S. Pat. No. 10,384,038, which is a divisional of U.S. patent application Ser. No. 14/515,435, filed Oct. 15, 2014, by J. Laudenslager et al., titled "Methods and Devices for Treatment of Stenosis of Arteriovenous Fistula Shunts", now U.S. Pat. No. 9,962,527, which claims priority under 35 USC 119(e) from U.S. Provisional Patent Application Ser. No. 61/891,830, filed Oct. 16, 2013, by J. Laudenslager et al., titled "Methods and Devices for Treatment of Stenosis of Arteriovenous Fistula Shunts", each of which is incorporated by reference herein in its entirety.

BACKGROUND

Laser catheters and laser delivery systems in general have wide range of applications in the medical field. Such systems may be used to deliver laser energy to desired sites of a patient's anatomy, and may be particularly suitable for delivering laser energy to locations within a patient's body that allow for minimally invasive treatment of a variety of indications using a variety of treatment modalities. Examples of some laser treatment modalities include heating tissue, stimulating tissue, drug activation within a patient's tissue and ablation of tissue.

Laser catheters currently approved for ablating and clearing blockages in human arteries may use a large single optical fiber, but may more commonly use a bundle of multiple optical fibers having a silica core, or a core of some other solid transmissive material. Large single fibers tend to be very stiff and contraindicated for use in tortuous anatomy and bundles of multiple fibers tend to lack ablation efficiency at the distal tip due to the gaps between adjacent fibers. This is particularly true for laser catheter systems that cut on contact. In addition, some indications for recanalization of blockages are particularly difficult to treat such that long term patency is maintained within a treated vessel that has been opened. This is often the case where blockages in veins present soft grumous type plaque lesions that often also include a large amount of soft thrombus.

What has been needed are fluid core waveguide based ablation catheters that are small and flexible enough to navigate a patient's vasculature, use biocompatible fluids, and are economical to manufacture. What has also been needed are such fluid core waveguide based ablation catheters that can be efficiently packaged and sterilized and maintain clinical integrity during a useful shelf life after shipment to an end user. What has also been needed are systems and methods suitable for treating grumous type lesions that improve long term patency of treated vessels.

SUMMARY

Some embodiments of a method of treating an arteriovenous fistula of a patient may include advancing a guiding device to the arteriovenous fistula, advancing a liquid core ablation catheter adjacent a blockage that is disposed within or adjacent the arteriovenous fistula and guiding the distal end of the liquid core ablation catheter with the guiding device. The method embodiment may also include axially advancing the liquid core ablation catheter through the blockage while emitting pulsed ultraviolet laser ablation energy from a distal end of the liquid core ablation catheter thereby ablating the blockage and debulking the blockage until the blockage is axially traversed by the distal end of the liquid core ablation catheter.

Some embodiments of a method of treating an arteriovenous fistula of a patient include axially advancing a liquid core ablation catheter through a blockage that is disposed within or adjacent the arteriovenous fistula while emitting pulsed ultraviolet laser ablation energy from an active emitting surface of a distal end of the liquid core ablation catheter. In some cases, such a liquid core ablation catheter may include an active emitting surface that is at least about 50 percent of an area of the distal end of the liquid core ablation catheter. The method may also include ablating and debulking the blockage while advancing.

Some embodiments of a method of treating an arteriovenous fistula of a patient include emitting pulsed ultraviolet laser ablation energy from a XeCl excimer laser at a nominal output wavelength of about 308 nm and a repetition rate of less than about 100 Hz into an input end of an ablation catheter and transmitting the pulsed ultraviolet laser ablation energy through the ablation catheter. The method may also include axially advancing and guiding a distal end of the ablation catheter through a blockage that is disposed within or adjacent the arteriovenous fistula while emitting the pulsed ultraviolet laser ablation energy from an active emitting surface of the distal end of the ablation catheter while ablating and debulking the blockage. The method embodiment may also include treating the blockage with a drug eluting balloon catheter after the distal end of the ablation catheter has traversed the blockage to improve long term patency of a lumen through the blockage.

Some package assembly embodiments to extend a shelf life of a liquid core catheter may include a liquid core catheter comprising a core liquid, a polymer spiral tube which includes an inner lumen filled with a storage liquid that is soluble in or miscible with the core liquid of the liquid core catheter and which is sealed at both ends to contain the storage liquid in the inner lumen of the polymer spiral tube, and a sealed pouch which is made of either metallized plastic or polychlorotrifluoroethylene that acts as a hermetic seal for liquids disposed within the sealed pouch. The sealed pouch may also include a hermetically sealed inner volume with the polymer spiral tube and liquid core catheter being disposed within the hermetically sealed inner volume.

Some embodiments of a liquid core ablation catheter may include a catheter tube having a fluoropolymer material and an internal coating disposed on an inner surface of the catheter tube. In some cases, the internal coating may include an amorphous fluoropolymer having a low index of refraction of less than about 1.34. The liquid core ablation catheter may also have an outer layer disposed on an outer surface of the catheter tube, the outer layer including polychlorotrifluoroethylene material that acts as a barrier to liquid diffusion out of an inner lumen of the catheter tube. Such prevention of liquid diffusion may include prevention of water vapor diffusion. The liquid core ablation catheter may also include a first solid window that seals the inner lumen at a first end of the catheter tube and a second solid window that seals the inner lumen at a second end of the catheter tube.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

FIG. 22 is an elevation view of a distal portion of a support catheter embodiment having an angled distal section configured for nutation of an ablation catheter disposed therein.

FIG. 23 is an end view of the support catheter of FIG. 22.

FIG. 24 is a schematic representation of an annular area of ablation swept by the distal end of the liquid core ablation catheter while undergoing nutation due to rotation of the angled support catheter of FIG. 22.

FIG. 25 is a schematic representation of a circular area of ablation swept by the distal end of the liquid core ablation catheter while undergoing nutation due to rotation of the angled support catheter of FIG. 22.

FIG. 49 is an enlarged view of the encircled portion 49 of the laser connector ferrule embodiment of FIG. 46.

FIG. 50 is a transverse cross section view of the input optic coupler assembly of the laser coupler of FIG. 49 taken along lines 50-50 of FIG. 49.

FIG. 52 is a top view of an embodiment of a liquid core ablation catheter disposed within a secondary liquid within an embodiment of a coiled polymer packaging tube which is supported by a cardboard support sheet.

FIG. 52A is a transverse cross section view of the polymer packaging tube and liquid core ablation catheter of FIG. 52 taken along lines 52A-52A of FIG. 52.

FIG. 53 is an exploded view of a package assembly embodiment including the coiled polymer packaging tube of FIG. 52 which may then be disposed within an interior volume of a sealed pouch which in turn may be disposed within an interior volume of a rigid box.

FIG. 54 is an elevation view in section of an embodiment of the assembled package assembly of FIG. 53.

FIG. 59 illustrates the laser ablation catheter of FIG. 58 being guided by a guidewire and axially advanced through the blockage while emitting pulsed ultraviolet laser ablation energy from a distal end of the liquid core ablation catheter and ablating and debulking the blockage.

FIG. 59A is a view of the arteriovenous fistula, the blockage, the ablation catheter embodiment and the guidewire of FIG. 59 in transverse cross section taken along lines 59A-59A of FIG. 59.

DETAILED DESCRIPTION

Figure 3:
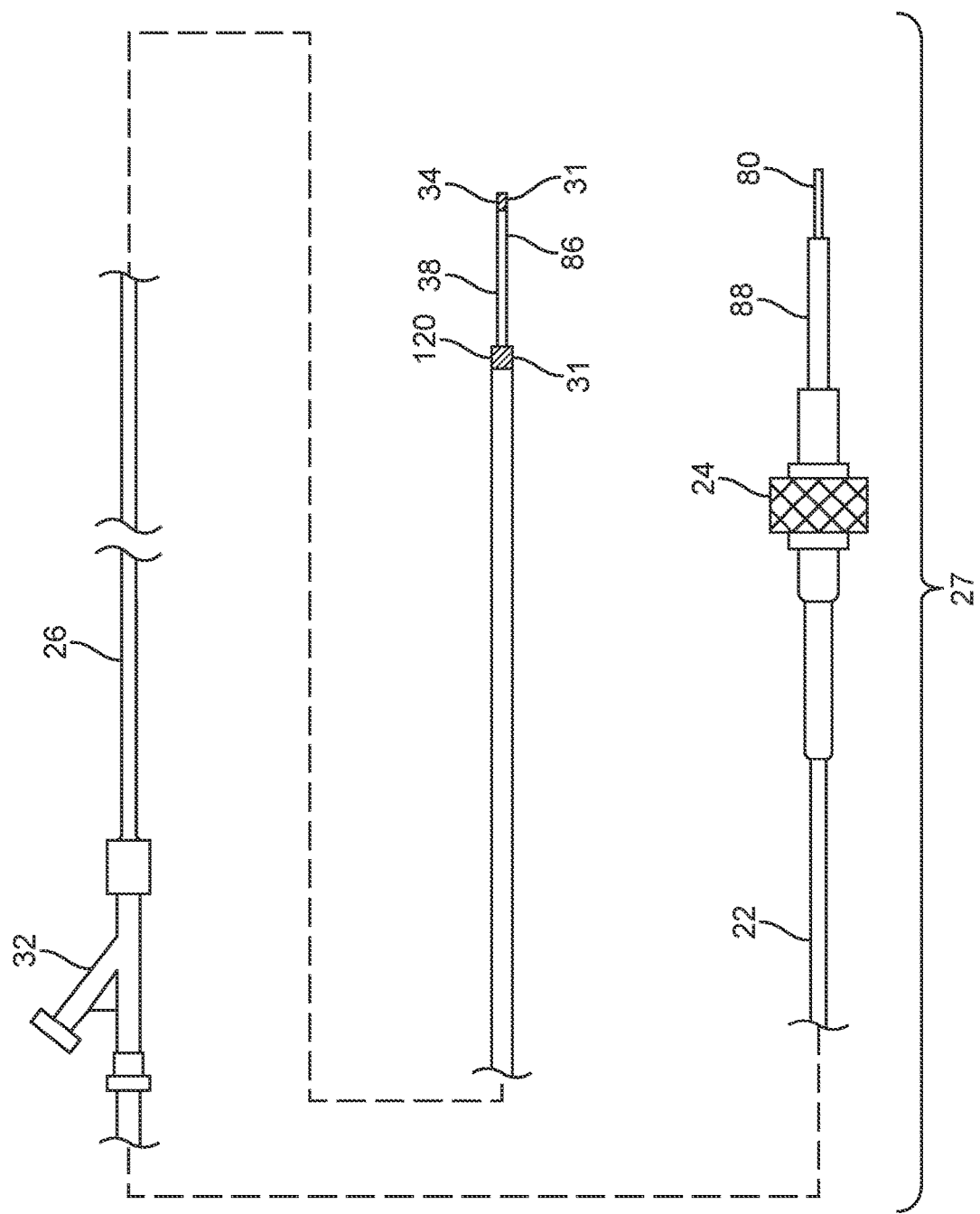
FIG. 3 is an elevation view of an embodiment of a laser catheter system including a liquid core ablation catheter disposed within a support catheter, the support catheter having a saline flush port.

As discussed above, laser catheters and laser delivery systems in general have wide range of applications in the medical field. Such systems may be used to deliver laser energy to desired sites of a patient's anatomy, and may be particularly suitable for delivering laser energy to locations within a patient's body that allow for minimally invasive treatment of a variety of indications using a variety of treatment modalities. Examples of some laser treatment modalities include heating tissue, stimulating tissue, drug activation within a patient's tissue and ablation of tissue or other organic material within a patient. Some examples of clinical indications for laser treatment may include laser atherectomy. One drawback of some current laser systems is the cost of the systems and devices used to deliver the laser energy, particularly with regard to those components that are designated as single use products. Liquid core catheter embodiments 22, as shown in FIG. 3, may generally be considerably less expensive than a silica fiber optic based catheter and may also have less dead space in the cutting area at the distal end of the catheter. The reduced dead space (that distal surface area that is not emitting laser energy) may be an important feature for ablation of blockages in arteries and for the ability of the catheter to cross a lesion in a patient's vessel.

Figure 18:
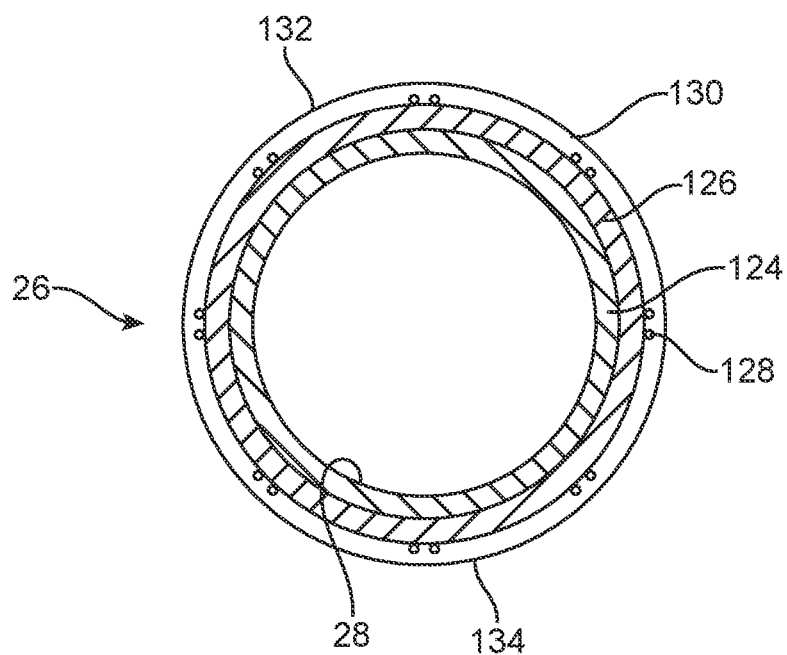
FIG. 18 is a transverse cross section view showing an embodiment of the support catheter of FIG. 4 and taken along lines 18-18 of FIG. 4.

FIGS. 1-27 show a laser ablation system embodiment 8 that includes a laser energy source 10 including a housing 12, a power cord 14, an activation footswitch 16, a control panel 18 and an output coupler 20. A liquid core ablation catheter 22 has a laser coupler 24 which is disposed at a proximal end 30 of the ablation catheter 22 and which is coupled to the output coupler 20 of the laser source 10. The ablation catheter 22 is disposed within an inner lumen 28 (as shown in FIG. 18) of a support catheter 26 which may be used to guide or support the ablation catheter 22 within a body lumen of a patient. The support catheter 26 includes a Y-adapter 32 coupled to a proximal end 30 thereof. The liquid core ablation catheter 22 is disposed within and passes through a central lumen (not shown) of the Y-adapter 32 as well. The support catheter 26 and ablation catheter 22 each may have a radiopaque marker 31 disposed at a respective distal end thereof. A working length of the liquid core ablation catheter 22 may include the length inside the patient's body between the access point and the target lesion site and the length outside the body necessary to couple or pass through the Y connector 32. An additional length may be needed to couple this working distance of about 90 cm to about 120 cm to the laser source 10 in some cases. If a laser source is large and located away from the patient, an additional length of waveguide may be necessary. Some laser catheter embodiments may be about 2 meters to about 3 meters long in some cases. In some cases, the laser source 10 of the laser system 8 may include a XeCl excimer laser which produces high energy pulses at a wavelength of about 308 nanometers, however, other high energy pulsed ultraviolet laser sources may be used. Some laser source embodiments 10 may have a pulse width of less than about 50 nanosec and a repetition rate of up to about 100 Hz. Some such laser source embodiments 10 may be capable of producing about 20 to about 100 mJ/pulse.

For some embodiments, the laser system 8 may also include an aiming diode (not shown) for applications where locating the distal tip 34 of liquid core ablation catheter 22 visually may be desirable. For some embodiments, a red color diode light source (not shown) may be used. This red diode wavelength may have a wavelength that is configured to penetrate some tissue types and may provide visibility of the distal tip 34 of the liquid core ablation catheter 22 and its position in the leg anatomy. The red diode light source may be located in the laser coupler 20 of the laser source 10 and coupled to the liquid core ablation catheter 22 by turning mirror or beam splitter (not shown) in some cases.

Figure 2:
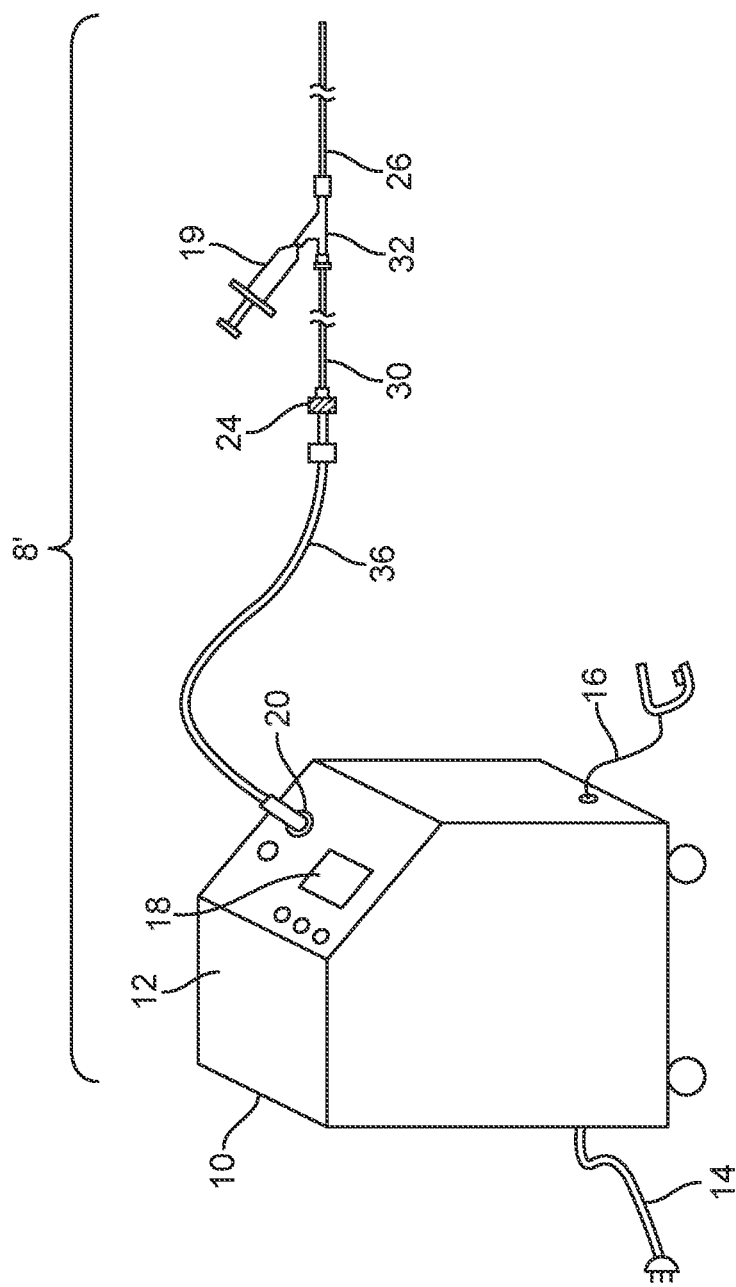
FIG. 2 is a perspective view of a laser system embodiment including a reusable extension waveguide connected between a laser and a disposable liquid core ablation catheter.

Since some ablation catheters 22 are generally disposable or single use only, the long 2-3 meter working length may be costly. For embodiments discussed herein, a robust liquid filled extension waveguide 36 for coupling from the laser source 10 to the single use disposable liquid core ablation catheter 22 may be used outside a patient's body and be designed to last for multiple uses. Such an optional extension waveguide 36, as shown in FIG. 2, may be used to connect the laser source 10 of the laser system 8' to a single-use liquid core ablation catheter 22 and have a length suitable to reach from the laser source 10 to the patient table (not shown). In some cases, the extension waveguide 36 may have a length of about 75 cm to about 300 cm, more specifically, about 75 cm to about 150 cm. The extension waveguide 36 may also be configured to contain a higher IR liquid core fluid than disposable liquid core ablation catheter embodiments 22 because it is generally disposed and used outside the patient's body and is not subject to some of the same design constraints as discussed above. As such, core liquids that have a higher IR may be used that may not be biocompatible in some cases.

Figure 1:
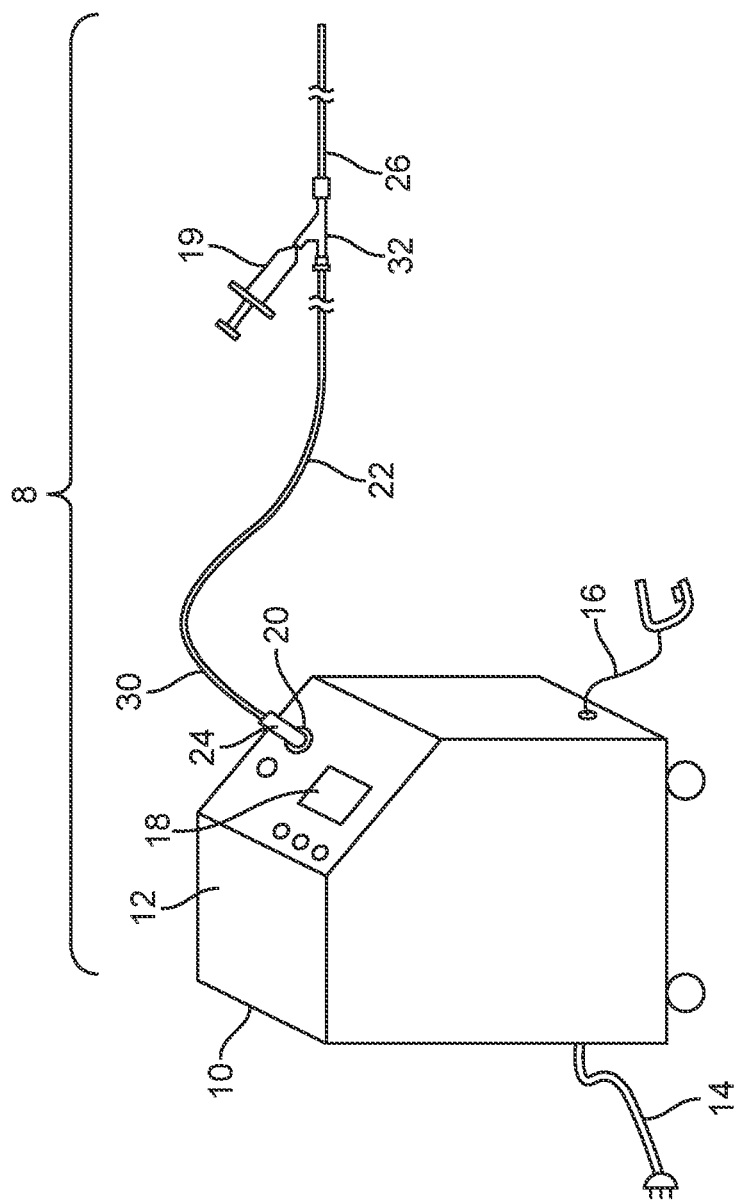
FIG. 1 is a perspective view of a laser system embodiment including a laser and a disposable liquid core ablation catheter coupled to the laser.
Figure 13:
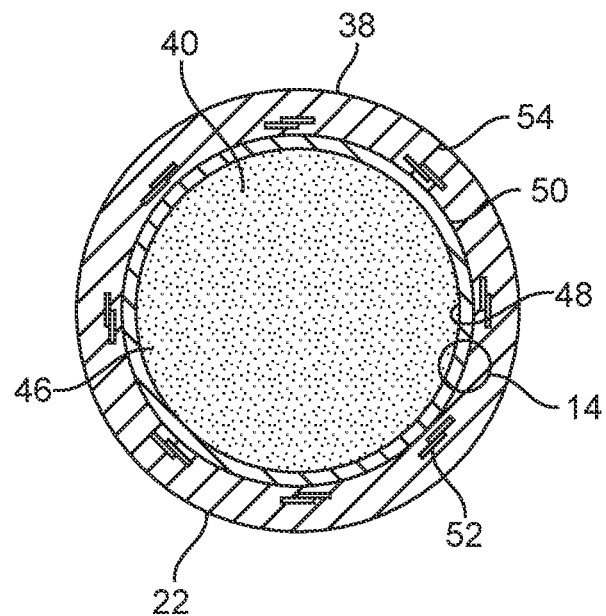
FIG. 13 is a transverse cross section of the liquid core ablation catheter embodiment of FIG. 5 taken along lines 13-13 of FIG. 5.

With regard to laser system embodiments 8 such as those shown generally in FIGS. 1 and 2, there are some features of the ablation catheter system 27, which includes the liquid core ablation catheter 22 and support catheter 26, shown in more detail in FIG. 3, that may be desirable or even necessary in some cases to function as desired. The liquid core ablation catheter 22, as shown in more detail in FIGS. 3, 5, 6, 8 and 10, includes a multi-layer catheter tube 38 having a low profile to fit inside particular blood vessels, which may have inner luminal diameters or inner transverse dimensions that vary in size from about 2 mm to about 6 mm. The wall thickness of the multi-layer catheter tube 38 of the liquid core ablation catheter 22 may be thin relative to a transverse dimension of the liquid core 40, as shown in FIG. 13, to ensure flexibility and to minimize the "dead space" between an outer distal surface 42 of the output window 82 (shown in FIG. 8) which emits tissue ablating energy and an outer dimension of the multi-layer catheter tube 38 which does not emit tissue ablating energy. The non-emitting wall of the catheter tube 38 forms the "dead space" that does not contribute to tissue cutting or ablation. As such, the ablation catheter 22 has a large fraction of cutting area relative to the overall area of the distal tip or surface of the ablation catheter. This may be achieved by having a multi-layer catheter tube 38 with a thin wall thickness as shown in FIG. 13.

For some embodiments, the multi-layer catheter tube 38 of the ablation catheter 22 is flexible enough to maneuver around bends in a patient's artery without kinking yet be stiff enough to be able to push the ablation catheter 22 through the vessel while ablating blockages. In some cases, the catheter tube 38 is able to be torqued and rotated at the distal end of the catheter tube 38 from a proximal portion 39 of the catheter tube 38 that extends outside the patient's body.

In some cases, the core fluid 40 used in the ablation catheter 22 is transparent in the ultraviolet laser energy wavelengths and may be a biocompatible fluid in case of accidental leakage from the catheter 22. In addition, the configuration of fluid core ablation catheter 22 may be capable of transmitting high power pulses above a tissue ablation threshold in the ultraviolet wavelength range preferably with pulse widths shorter than 50 nsec and at repetitions rates of up to 100 Hz in order to achieve the desired results in some cases. For some indications, the liquid core ablation catheter 22 may be designed for single use only but may also have a long shelf life after sterilization of typically one year or more for use in a clinical setting. Therefore, the core liquid 40 disposed in the inner lumen 46 of the ablation catheter 22 should not diffuse out of the thin wall multi-layer catheter tube 38 of the catheter system 27, as shown in FIG. 3, over this type of time period for some embodiments. Also, for some embodiments, the materials of the multi-layer catheter tube 38 may be sterilizable without significant degradation or degradation that would render the ablation catheter 22 unusable. Gamma or X-ray sterilization may be ideal in some situations and may be useful in order to ensure that any fluid, such as liquid water used for a transmissive core, inside the ablation catheter is sterilized.

Figure 14:
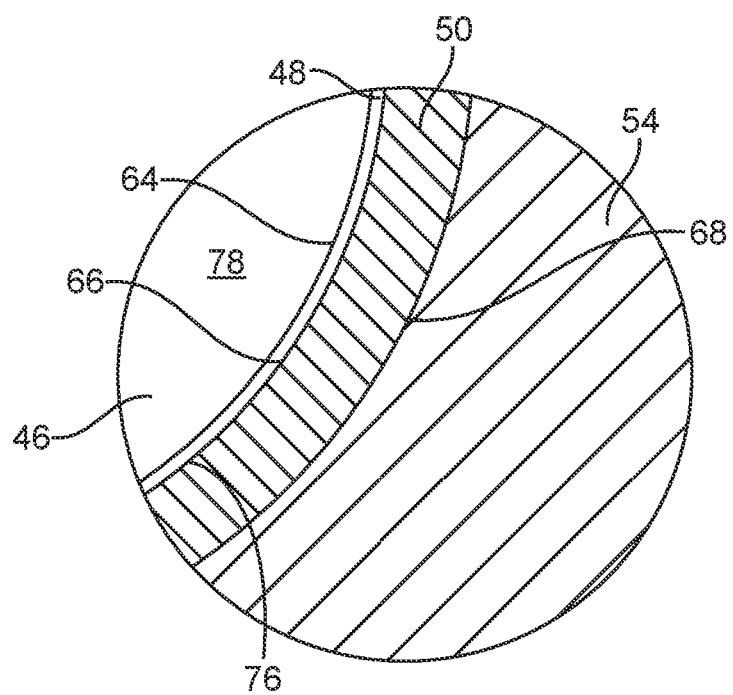
FIG. 14 is an enlarged view in section of the wall of the liquid core ablation catheter of FIG. 13 indicated by the encircled portion 14 in FIG. 13.

For some embodiments, the transmission of laser energy through the liquid core ablation catheter 22 is high enough to enable a relatively small laser source to be used for the laser system 8 in order to save cost. For some indications, the ablation catheter 22 allows sufficient transmission to achieve a minimum output energy per pulse to ablate differing arterial plaque types or any other organic material within a patient's body. In some cases, such a minimum output energy may range from about 4 milli-Joules/mm$^2$ (mJ/mm$^2$) to about 14 mJ/mm$^2$ for a XeCl laser at a wavelength of about 308 nanometers (nm) and an approximate pulse width of about 10 nanoseconds (nsec) in some cases. Longer 308 nm laser pulses of about 100 nsec may have slightly higher ablation thresholds for the same tissue types. As such, a fluid for the core of the liquid filled waveguide may transmit high power and high pulse energy ultraviolet excimer laser pulses in some cases and may be biocompatible for insertion into human arteries. Pure water and normal saline (0.9% NaCl aqueous solution) are highly transparent and are biocompatible but they both have very low indices of refraction (IR) compared to the IR of most polymer tubing materials used in liquid waveguide catheters. For example, at a temperature of about 20 degrees C., water has an IR of about 1.333 in the visible wavelength region and normal saline has an IR of about 1.335. Teflon® fluorinated ethylene propylene (FEP) tubing may have an IR in the visible range of light of about 1.338 which may be too high to produce an effective waveguide using water or saline for some ablation catheter embodiments 22. This is because the IR of the inner luminal layer 48 of the catheter tube 38 as shown in FIG. 14, must be less than the IR of the fluid core 40 to achieve total internal refraction of laser energy being guided by the liquid core ablation catheter.

Embodiments of the catheter system 27 may be used for navigation within the tortuous anatomy of a patient's vasculature may include a multilayer design or designs. In some cases, a central catheter tubing core 50 may optionally be braided with a metal wire or ribbon 52 and this portion may have an over jacket 54 as shown in FIG. 13. This type of design may be used for applications that require high torque, burst pressure resistance, pushability, steerability and kink resistance. The physical characteristics of such a braided catheter embodiment 27, as shown in FIG. 3, may be varied by using different durometer values for the plastic tubing of the catheter body and by varying the pitch and thickness for the metal braid. This basic design concept may be applied to the unique characteristics of liquid core ablation catheter embodiments 22.

Figure 15:
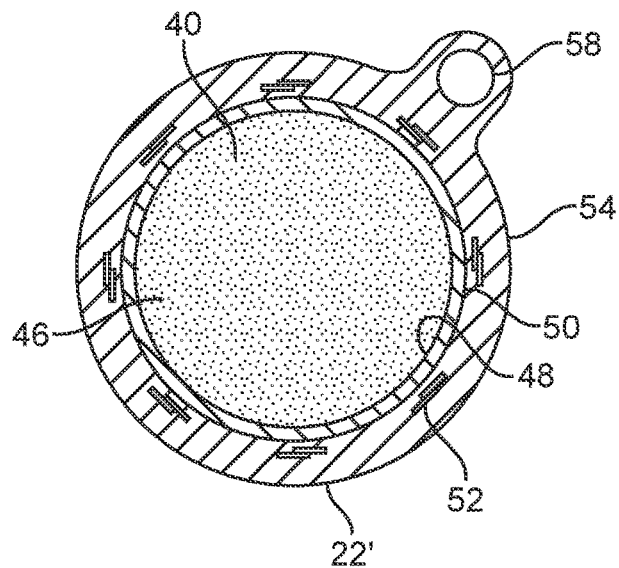
FIG. 15 is a transverse cross section view of an embodiment of a liquid core ablation catheter with an eccentric guidewire lumen.
Figure 16:
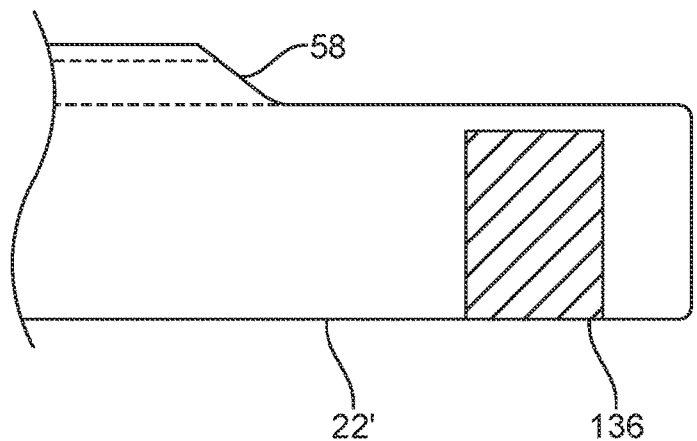
FIG. 16 is an elevation view of a distal portion of the liquid core ablation catheter embodiment of FIG. 15.
Figure 26:
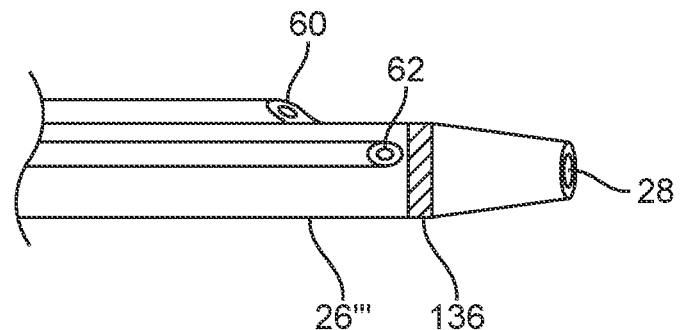
FIG. 26 is a perspective view of a distal portion of an embodiment of a multi-lumen support catheter having two eccentric guidewire lumens.
Figure 27:
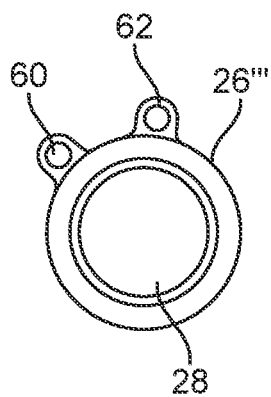
FIG. 27 is an end view of the support catheter embodiment of FIG. 26.
Figure 31:
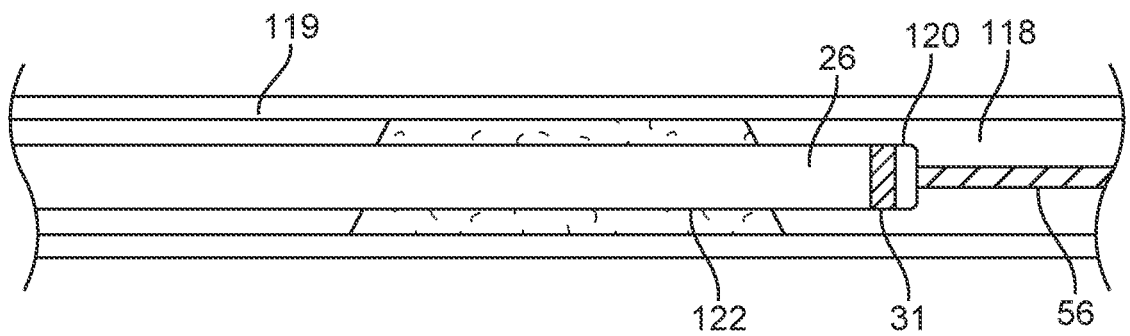

In some cases, the laser ablation catheter system 27 includes a guiding device or other suitable means of guidance of the ablation catheter through a vessel lumen or blockage thereof, such as an arterial blockage. Guidewire 56, as shown in FIG. 31, which is disposed in a concentric or eccentric position within a vessel 119 may be used in some cases as a guiding device and may pass through one or more guidewire lumens, such as guidewire lumen 58 of the liquid core ablation catheter embodiment 22' as shown in the embodiments of FIGS. 15 and 16. The ablation catheter 22' includes an eccentric guidewire lumen 58 disposed along an outer surface of the ablation catheter 22. The guidewire lumen may have a distal port disposed proximally from a distal end of the ablation catheter 22' by at least about 5 mm. The guidewire lumen 58 may have a longitudinal length of at least about 10 cm. Support catheter embodiments 26''' including one or more guidewire lumens such as the two guidewire lumens 60 and 62, as shown in the embodiments of FIGS. 26 and 27, may also be used to guide and support the ablation catheter.

Figure 19:
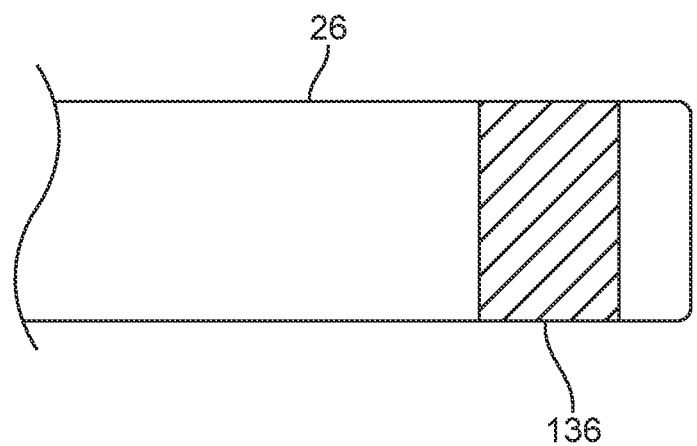
FIG. 19 is an elevation view of a distal portion of the support catheter embodiment of FIG. 18.
Figure 20:
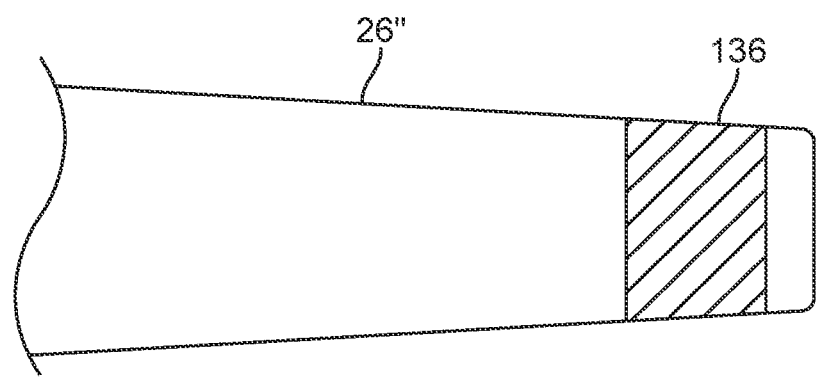
FIG. 20 is an elevation view of a distal portion of a support catheter embodiment that includes a tapered distal portion.
Figure 21:
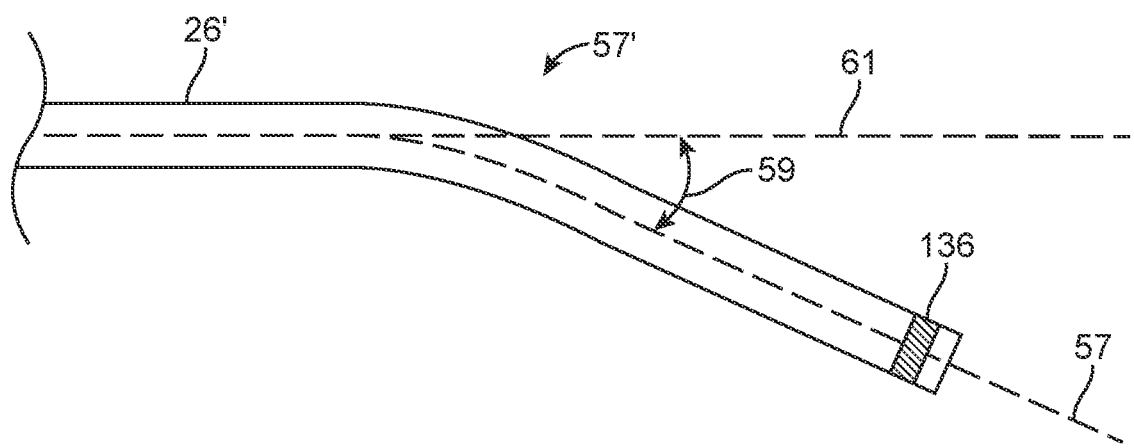
FIG. 21 is an elevation view of a distal portion of a support catheter embodiment that includes an angled distal end.
Figure 62:
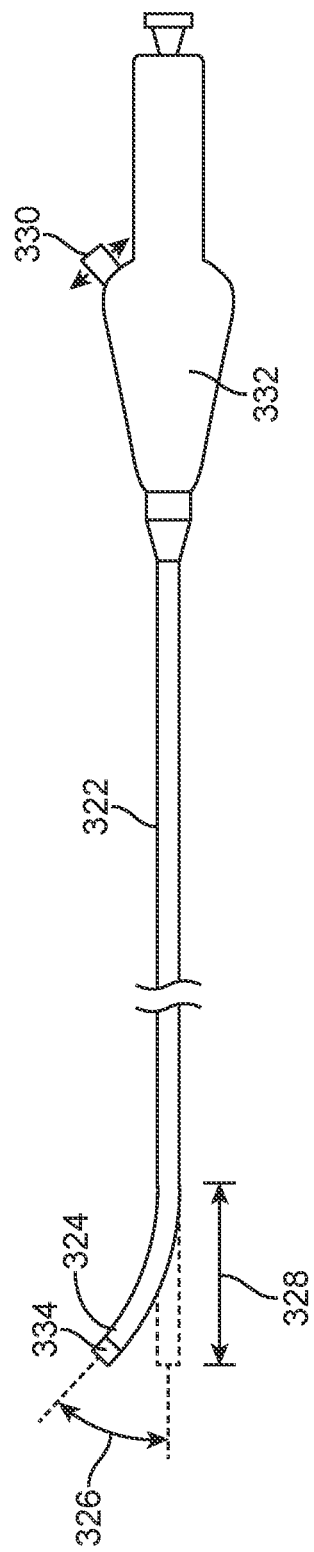
FIG. 62 is an elevation view of an embodiment of a support catheter which includes a deflectable distal section.

In addition, straight support catheters 26 as shown in FIG. 19 or angled support catheters 26' as shown in FIG. 21, may be used as a guiding device for guiding a liquid core ablation catheter 22 through restenosed stents in that the stent itself may serve as a guide to maintain a desired position of the distal end of the ablation catheter 22 within the patient's anatomy or prevent the ablation catheter 22 from causing an arterial wall perforation. Some support catheter embodiments may include a tapered support catheter embodiment 26", angled support catheter embodiment 26' or profiled support catheter embodiment as shown in FIGS. 20 and 21 to help center the liquid waveguide ablation catheter 22 remain in the vessel lumen 118 during use as shown for example in FIGS. 28-32. The angled support catheter embodiment 26' as shown in FIG. 21, may have an angled distal tip section 57' with a discharge axis 57 disposed at an angle, indicated by arrow 59, with respect to a nominal longitudinal axis 61 of the support catheter 26'. For some embodiments, the angle 59 of the discharge axis of the support catheter 26' may be about 5 degrees to about 45 degrees, more specifically, about 10 degrees to about 30 degrees. In other cases, a straight support catheter with a means to angle or otherwise transversely deflect the tip in one or more directions or axes, as shown in FIG. 62, can be used to deflect the tip from a straight configuration to an angled deflected configuration having an angle 59 of up to a 45 degree angle for proper positioning of the ablation catheter cutting tip. An example of such a support catheter having a deflecting tip or distal section may include a Universal Deflectable Guide Catheter, model 01415 manufactured by BioCardia Corporation located at 125 Shoreway Road, Suite B, San Carlos, Calif.

In addition, an angled support catheter embodiment 26', as shown in FIGS. 22-25, may be rotated about its longitudinal axis, as shown by arrow 65 in FIG. 22, over an ablation catheter, such as liquid core ablation catheter 22, which extends distally therefrom. Such rotation of an angled support catheter 26' with a deflected distal section may result in orbiting or nutation of the distal tip of ablation catheter 22 during the ablation process, i.e. during emission of ablation energy suitable for tissue ablation from the distal end of the liquid core ablation catheter 22. This nutation of the ablation energy emitting surface of the liquid core ablation catheter 22 may produce a band or annulus of ablation or tissue removal as shown in FIG. 24. Such a process is also illustrated in the elevation view of a tissue ablation process shown in FIG. 36. The band or annulus of ablation produced by such and configuration and method may be suitable to create a larger neo-lumen or passage through a lumenal blockage, obstruction or constriction than would be possible by pushing the same liquid core ablation catheter 22 directly through the obstruction or constriction in a straight line.

Figure 36:
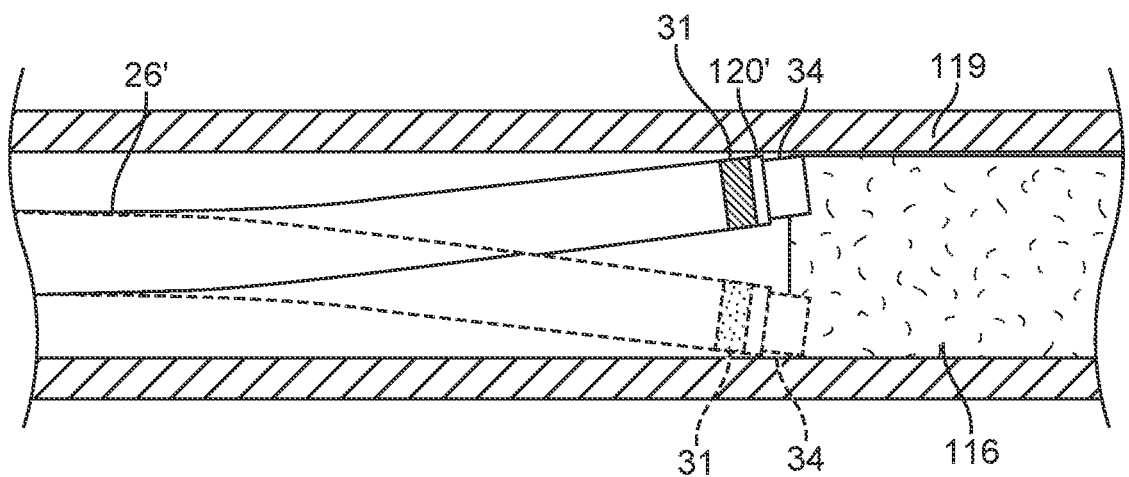
FIG. 36 is an elevation view in partial section illustrating creation of an annular area of ablation of a vessel blockage by nutation of an ablation catheter as shown in FIGS. 22-24.

Although FIGS. 24 and 36 illustrate a band or annulus of ablation carried out by nutation of the support catheter 26' about the liquid core ablation catheter 22, a circular area of ablation may also be generated for rotations with lesser nutation magnitudes as shown in FIG. 25. In such cases, some portion or portions of the emitting surface of the distal end of the liquid core ablation catheter 22 would be disposed over a center of the neo-lumen being ablated into the obstructive tissue. In such cases, the neo-lumen may still be substantially larger than an outer surface of the emitting surface or outer transverse dimension of the liquid core ablation catheter 22. In some instances, the angled distal section 57' of the angled support catheter 26' may have a length, as shown by arrow 63 in FIG. 22, of about 5 mm to about 50 mm, more specifically, about 5 mm to about 15 mm. In some cases, a discharge angle as indicated by arrow 59' in FIG. 22 may be about 3 degrees to about 10 degrees.

In some cases, the numerical aperture of a liquid core ablation catheter 22 may be above a certain minimum value in order to prevent losses in the catheter, particularly due to bending of the catheter. The numerical aperture of the liquid core ablation catheter 22 depends to a large extent on the difference between the IR of the core liquid 40 and the IR of an inner luminal layer 48 of the multi-layer catheter tube 38. The inner luminal layer 48 is a tubular layer of material or materials of the catheter tube 38 which surrounds the core liquid 40 within the liquid core ablation catheter 22. The inner luminal surface 64 (shown in FIG. 14) of the inner luminal layer 48 is the surface that contacts the core liquid 40. It is the interface between the core liquid 40 and the inner luminal layer 48 that may be configured to generate total internal refraction of laser light disposed and propagating within the core liquid 40. As such, in some cases, the IR of the core liquid 40 should be greater than an IR of the inner luminal layer 48 of the catheter tube 38 by at least about 0.02.

The inner luminal layer 48 of the catheter tube 38 may also be transparent or substantially transparent to the wavelength of laser energy being transmitted through the core liquid 40. This may be particularly desirable because the U.V. radiation refracting at the core liquid 40 inner luminal layer 48 interface may extend into the inner luminal layer 48 (and possibly beyond the inner luminal layer 48 of the multi-layer catheter tube 38) by a distance of about several wavelengths during the refraction process. When the refracted light extends into the inner luminal layer 48 (or any other subsequent layers of the multi-layer catheter tube 38 such as the base layer tube 50 as shown in FIG. 14) during the refraction process it may be strongly absorbed if the material of the inner luminal layer 48 is not transparent or substantially transparent to the wavelength and energy density of the refracted light. This means that many materials may be incompatible for use as an inner luminal layer 48 of the multi-layer catheter tube 38 of the liquid core ablation catheter 22, particularly for embodiments using a core liquid 40 of water or normal saline.

In view of the foregoing, inner luminal layer embodiments 48 may be generated by coating an internal surface 66 of the base layer 50, as shown in FIG. 14, of a multi-layer catheter tube 38 made from common catheter materials with a film of material having an IR of less than about 1.33. As discussed above, it may be important for such a coating material to be transparent or substantially transparent to the ultraviolet wavelength used in the corresponding catheter. In addition, the inner luminal layer 48 may also have a sufficient wall thickness to retain the high power U.V. laser energy and prevent substantial losses through the inner luminal layer 48 to those layers of the catheter tube 38 surrounding the inner luminal layer 48 as for some embodiments, the surrounding tubular layers may include materials which absorb the U.V. laser energy and may be damaged or destroyed by it.

Certain amorphous fluoropolymers may be used as coatings having a low IR relative to some core liquids 40 and thus may be used for the generation of an inner luminal layer 48 of catheter tubes 38. DuPont® Corporation located in Wilmington Del. has developed certain coatings including, in particular, fluorinated (ethylenic-cyclo oxyaliphatic substituted ethylenic) copolymer (Teflon AF®) which is a family of amorphous fluoropolymers based on copolymers of 2,2-bistrifluoromethyl-4,5-difluoro-1,3-dioxole (PDD) and tetrafluoroethylene (TFE). According to DuPont, the principle difference between the various grades of Teflon AF® is based solely on the relative amounts of TFE to PDD in the polymer chain. Teflon AF® polymers have the lowest index of refraction of any known polymer and are substantially transparent to light, even at U.V. wavelengths making these materials suitable as low index coatings for waveguide applications. In some cases, these amorphous fluoropolymers may be formulated with different IRs. Teflon AF 2400® has a TFE to PDD ratio of about 11:89 and a particularly low IR of about 1.29 in the visible light wavelength range. Teflon AF 1601® has a TFE to PDD ratio of about 36:65 and an IR of about 1.31 at the visible light wavelength range. Either of these formulations may be used to form an inner luminal layer 48 of the multi-layer catheter tube 38 of the ablation catheter 22. It should be noted that the IR of these fluorinated polymers as well as the IR of water and normal saline, increase in value for UV wavelengths relative to values for light in the visible wavelength range.

We have measured the transmission of 308 nm laser pulses through both water and saline filled tubes of uncoated Teflon® FEP and observed that the light was lost in the first foot of the tube. Pulses having a wavelength of about 308 nm may be readily transmitted through a meter long FEP tube filled with the same fluids when the tube was lined with Teflon AF 1601®. Therefore, in the UV the IR difference between water or saline and the Teflon AF 1601® or Teflon AF 2400® appears to be sufficient for total internal refraction and high transmission of short pulse laser energy having a pulse width of less than about 50 nsec and a wavelength of about 308 nm.

These amorphous fluoropolymers discussed above may be soluble in selected solvents to facilitate coating processes. In some cases, these amorphous fluoropolymer coatings adhere best to fluorocarbon polymers but not very well to other plastic types. As such, when using an amorphous fluorinated polymer material for an inner luminal layer 48 of the embodiments herein, the choice of suitable materials for the remaining layers of the catheter tube 38 may be limited. These and other properties of the amorphous fluorinated polymer materials may also create difficulties for construction of suitable catheter tubes 38 utilizing amorphous fluorinated polymer materials for the inner luminal layer. For example, Teflon AF 2400® which has an IR of about 1.29 is generally produced in a 1% solution which may be too dilute to achieve a sufficient coating thickness to confine U.V. laser energy to the core liquid 40 and inner luminal layer 48. Teflon AF 1601® with concentrations up to about 18% may be used to produce a coating for an inner luminal layer 48 with sufficient thickness to confine U.V. laser energy at 308 nm wavelength and with an IR of about 1.31.

Teflon® FEP tubes may not be as suited for use with liquid filled laser waveguides 22 in some cases because water and aqueous solutions of saline over time may diffuse out of the FEP tube in low humidity environments. As an example, we filled a thick wall tube of Teflon® FEP with water, sealed the ends and placed it in an oven at 50 degrees C. and saw bubble formation within 10 days. In some cases, this diffusion of water might be prevented by placing the FEP water filled tube in a plastic enclosure which also contains water. For example, the finished FEP liquid filled ablation catheter can be packaged in a spiral plastic tube filled with a second liquid that may be the same as the liquid disposed within the core of the liquid filled ablation catheter, or a second liquid that is soluble in or miscible with the liquid that is disposed within the core of the liquid filled ablation catheter. In some cases, the second liquid may include water or a saline solution. The spiral plastic tube may be sealed at both ends for long storage shelf life. This spiral package may then be sealed in a hermatic pouch formed of either PCTFE or metalized plastic material as shown in FIGS. 52-54 and discussed in more detail below. The entire package containing the catheter may then be sent for gamma sterilization to sterilize all the fluid contained in the catheter and spiral. In some cases, catheters 22 may be placed in an oven at about 50 degrees C. to about 60 degrees C. for several months to perform accelerated lifetime testing to simulate a one year shelf life. Therefore, in some cases, it may be desirable for the multi-layer catheter tube 38 of the ablation catheter 22 to not have a high permeability for water transfer at oven temperatures of about 50 degrees C. to about 60 degrees C. to qualify as a medical catheter for long shelf life in some cases. In addition, for some applications, the tubing material or materials of the multi-layer catheter tube 38 and/or support catheter 26 should be suitable for sterilization with gamma radiation or x-rays without significant degradation. Teflon® FEP is generally not as suitable for high levels of gamma radiation sterilization.

Another disadvantage with using an FEP tube liner may be that the hardness shore durometer of about 55D is about half that of PCTFE which may have a shore hardness of about 85D to about 95D. When the FEP liner is thin and has a low durometer then there may be an impression of thin elements of an optional braid material 52 used on an outside surface 68 (shown in FIG. 14) of a base tube 50 of the multi-layer catheter tube 38 to transfer into the inner luminal surface 64 of the inner luminal layer 48 which may cause the light to be scattered out of the tube. Also, when an ablation catheter 22 is placed in the Y adapter 32 and a corresponding hemostatic valve thereof, the valve may compress a low durometer ablation catheter embodiment 22, distort the wall structure of the ablation catheter and hinder transmission of light therethrough.

We have found that polychlorotrifluoroethylene, PCTFE, has one of the lowest diffusion rates for water compared to other polymer plastics, and can be coated with Teflon AF® solutions and can also be sterilized using radiation. We filled a thin wall PCTFE tube with water and sealed the ends of the tube and placed the sealed assembly in an oven at 60 degrees C. for one month. No diffusion of the water in the PCTFE tube was apparent even after the one month dwell time in the oven. As such, PCTFE may be used in some cases for certain layers of the multi-layer catheter tube 38. In fact, a liquid filled UV ablation catheter made of FEP or similar material with a low index coating applied can be over extruded with a thin layer of PCTFE to provide an alternative or cumulative means for providing a water barrier or vapor barrier for other liquids for long term shelf life storage.

The higher durometer for PCTFE of about 90 D even with thin walls of about 0.002" may provides extra stiffness that resists penetration or transfer of a braid pattern onto an inner luminal surface 64 of the inner luminal layer 48 a liquid core ablation catheter 22. This higher durometer may also add stiffness and pushability to the multi-layer catheter tube 38, but might kink easily in some cases without the optional metal braid 52. PCTFE tubing does have a draw back in that the maximum working temperature of the material may be about 125 degrees C. in some cases. For some embodiments, the ablation catheter 22 may include a multi-layer catheter tube 38 an outer layer or over-jacket 54, as shown in FIGS. 13 and 15, having a lower hardness durometer of about 65D to about 75D, more specifically, about 70D. In some cases, the outer layer or over-jacket layer 54, as shown in FIG. 13, may have to be processed at a temperature level where the PCTFE wall of the base tube is not compromised. This may have the effect of substantially limiting the choice of materials and processing methods for the over-jacket 54 for the multi-layer catheter tube 38 of the liquid core ablation catheter 22.

There are several options for forming the inner luminal layer 48 of the multi-layer catheter tube 38 from an amorphous Teflon AF® or other suitable amorphous fluoropolymer on the inside of a base tube 50, such as a PCTFE or FEP base tube 50. One method of creating such an inner luminal layer 48 includes using a solution of Teflon AF® dissolved at percentages of about 1% to about 18% Teflon AF® solids in a suitable solvent such as Fluorinert solvent. One type of Fluorinert is a perfluorocarbon made by 3M Company under the description FC-40. The Fluorinert solvent may be offered in various formulations that have differing boiling points. In some cases, a Fluorinert solvent having a boiling point of about 155 degrees C. may be used for the processes discussed herein.

One or more coatings may be applied to the inside of the PCTFE tube and the solvent may then be evaporated off to leave a thin layer solid film of low IR of Teflon AF® of about 5 microns to about 50 microns thick, more specifically, about 5 microns to about 20 microns thick. Various Teflon AF® layers with differing IRs and concentrations may be applied or mixtures of differing solutions may be applied in a single mixed layer. Examples of amorphous coatings with low indices of refraction may include Teflon AF 1601®, Teflon AF 2400®, Cytop® manufactured by Asahi Glass Company located in Japan, and Hyflon AD 40® or Hyflon AD 60® made by Solvay Solexis Company located in Italy. Any of these amorphous fluoropolymers may be mixed with a high boiling point perfluoropolyether (PFPE) oil to provide thicker layers at lower cost. In some cases, a PFPE oil such as Fomblin YR 1800® sold by the Solvay Solexis Company may be used. The boiling point of such a PFPE oil may be about 220 degrees C. to about 275 degrees C. for some embodiments.

Regarding the processing of some inner luminal layer embodiments 48, the manufacturer recommends in some cases that these amorphous fluoropolymer coatings be annealed above the boiling point of the solvent used and then tempered for several minutes above the glass transition temperature, Tg, of the solid amorphous fluoropolymer film which may be about 160 degrees C. for Teflon AF 1601® and about 240 degrees C. for Teflon AF 2400®. Exposure to these temperatures might be detrimental for the PCTFE tube and other low melt plastics such as Pebax® used for the over-jacket 54 on the optional metal braid 52 of the multi-layer catheter tube 38 of the liquid core ablation catheter 22. In some embodiments, Pebax® materials may have a melting temperature of about 135 degrees C., which is well below the recommended processing temperatures to both remove the solvents and get the materials above the Tg of the amorphous fluoropolymer. Method embodiments discussed herein were specifically developed to enable the application of these films onto an inner luminal surface of a PCTFE tube (or the like) to create the inner luminal layer 48 of the ablation catheter 22. In some cases, these techniques use relatively lower process temperatures for longer time durations to achieve workable amorphous fluoropolymer inner luminal layers 48, as shown in FIG. 14, for multi-layer catheter tubes 22 which may then be filled with a liquid core 40 such as water or saline.

For some embodiments, a method of generating a multi-layer catheter tube 38 may include a drip coating method whereby a solution of amorphous fluoropolymer or mixtures thereof are dissolved in solution such as Fluorinert FC-40® from 3M at concentrations high enough to provide at least a 5 micron or more layer thickness per coat. One or more multi-layer catheter tubes 38 may be mounted vertically and cleaned on the inside luminal surface with isopropyl alcohol or the like. The inner luminal surface of the catheter tube 38 may then be coated with the solution of amorphous fluoropolymer for a given dwell time and annealed at temperatures less than about 100° C. or the melting point of the multilayer catheter material for times sufficient to remove all the solvent. In some cases, dwell time at temperatures of less than about 100° C. may be up to about 4 hours. The lower temperatures for annealing may be configured or otherwise selected in order to prevent thermal damage to the polymer materials of the multi-layer catheter tube 38 to which the coating is being applied. This drip coating process may be repeated multiple times to produce an inner luminal layer 48 thickness and uniformity that encapsulates or otherwise contains high power laser energy at a wavelength of about 308 nm in the resulting waveguide core of an ablation catheter 22 constructed from such a multi-layer catheter tube 38 and core-inner luminal layer junction therein. After processing, the multi-layer catheter tube 38 may be filled with an appropriate core liquid 40 and sealed with suitable windows at both proximal and distal ends thereof.

For some embodiments, the inner luminal layer 48 may also be thick enough to smooth out any surface irregularities on the inner surface of a drip coated tube, such as a base layer tube 50 made from PCTFE, FEP or the like. For some embodiments, a thickness of about 5 microns to about 15 microns for the low IR internal material of the inner luminal layer 48 might provide for an efficient coating. In some cases, Teflon® FEP or other fluoropolymer based materials may be used as an alternative to PTCFE for making base layer tubes 50 (see FIG. 14), however, there may be issues with regard to keeping core fluids 40, such as water core fluids, from diffusing out of the liquid core ablation catheter 22 during shelf life storage. Packaging the finished and sterilized liquid core ablation catheter 22 in a high humidity package may mitigate this problem in some cases, particularly in instances where FEP is used. Suitable materials for such a package may include an openable enclosure made from metal coated plastic, PCTFE or any other suitable material capable of producing a hermetic or hermetic type seal that is sealable about a finished ablation catheter or catheter system and is suitable for a desired type of sterilization such as gamma e-beam or the like.

Figure 8:
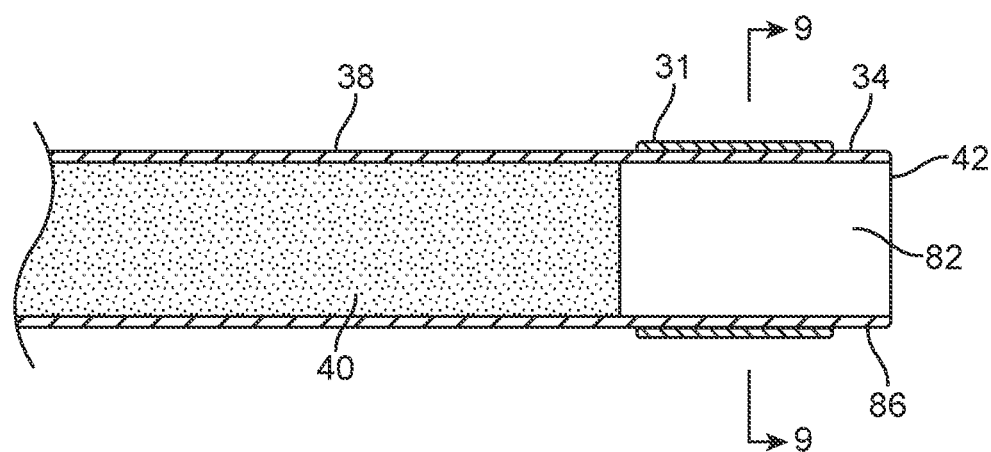
FIG. 8 is an elevation view in partial section of a distal portion of the liquid core ablation catheter embodiment of FIG. 3.
Figure 9:
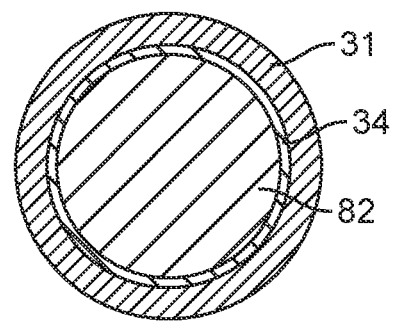
FIG. 9 is a transverse cross sectional view of the liquid core ablation catheter of FIG. 8 taken along lines 9-9 of FIG. 8.

Other methods for forming such a low index layer from these materials may include extruding a thin layer, for example, of solid Teflon AF 2400® or Teflon AF 1601®, over a smooth polished metal mandrel to form the inner luminal layer 48 of the multi-layer catheter tube 38 of the liquid core ablation catheter 22. In some cases, such an extruded thin layer of low index material may have a thickness of about 5 microns to about 50 microns. Once the amorphous fluoropolymer inner luminal layer 48 is extruded over the mandrel, the outer surface 76 (shown in FIG. 14) of the inner luminal layer 48 may then be etched to promote surface adhesion thereto. A thicker wall PCTFE base layer tube 50, or base layer tube 50 made from another suitable material, such as FEP, may then be over extruded onto the etched outer surface 76 of the inner luminal layer 48, followed by braiding of an optional multi-filament braid 52 over the outer surface of the PCTFE tube 50. Then an over-jacket 54 may be extruded over an outer surface of the braided layer 52 and PCTFE base tube 50. For some embodiments, the mandrel may then be removed from the multi-layer catheter tube embodiment 38. The tubular inner lumen 78 that remains once the mandrel has been removed may then be filled with transmissive liquid 40 and sealed with optical windows at each end, specifically an input optical window 80 at the proximal end 84 (shown in FIGS. 3 and 6) of the multi-layer catheter tube 38 and an output optical window 82, as shown in FIG. 8, at the distal end 86 (shown in FIG. 3) of the multi-layer catheter tube 38. The optical windows 80 and 82 may also be transparent to the wavelength of laser energy to be guided therein.

Some methods may include placing multiple coating layers of an amorphous fluorocarbon material dissolved in a solvent over a mandrel wire with heat annealing between layers to above the Tg of the polymer to form the inner luminal layer 48. The outer surface 76 of the inner luminal layer 48 may then be etched in order to facilitate adhesion thereto. A PCTFE base layer tube 50, or base layer tube 50 made from another suitable material, may then be over-extruded or otherwise applied over the outer surface 76 of the inner luminal layer 48 with a subsequent optional braid 52 applied to an outer surface of the base layer tube 68 and over jacket 54 added to an outer layer of the braid 52 and base layer tube 50 to complete the multi-layer catheter tube 38. In this example, all the high temperature annealing is done with a high temperature mandrel wire before the plastics are overlaid. No matter which method is used, the PCTFE base tube 68 is independent of the inner luminal layer 48 which may be a thin low IR coating where all the refraction of the guided laser energy takes place. In some cases, the thickness of this thin inner luminal layer 48 must be at least several wavelengths thick for refraction as discussed above.

This method may also include coating a mandrel wire with a concentrated solution of an amorphous fluoropolymer dissolved in a solvent. The percentage of solids may be greater than 10% for maximizing wall thickness per coating layer. The coated mandrel wire may then be annealed above the boiling point of the solvent, which may be FC-40 whose bp is 155° C. and then annealed up to 30 minutes at or above the glass transition temperature, Tg, of the solid fluoropolymer, which for Telflon AF 1601® may be about 160 degrees C. The thickness of this layer may be about 10 microns to about 50 microns for some embodiments. This layer may then etched and over extruded with a water barrier layer such as PCTFE, braided and then overjacketed.

Figure 6:
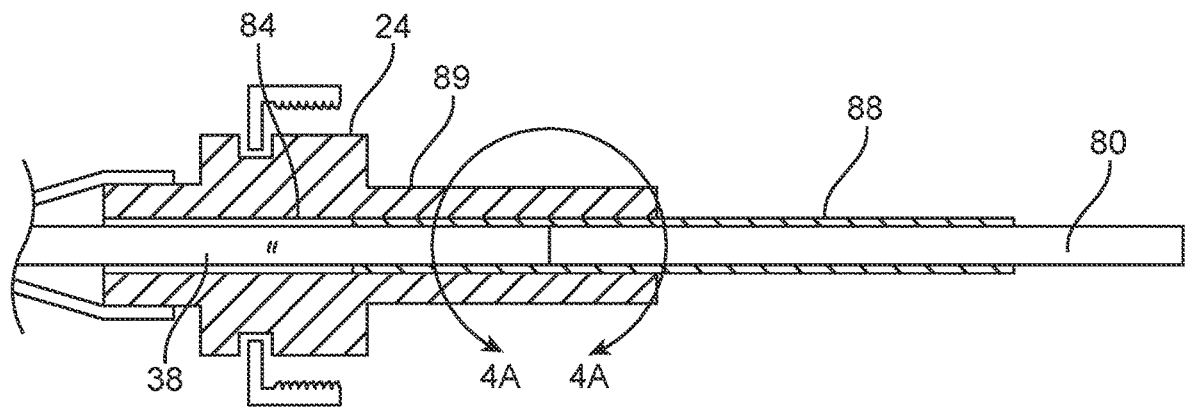
FIG. 6 is an enlarged elevation view in partial section of the laser connector ferrule embodiment of FIG. 3 for use with a liquid core ablation catheter.
Figure 7:
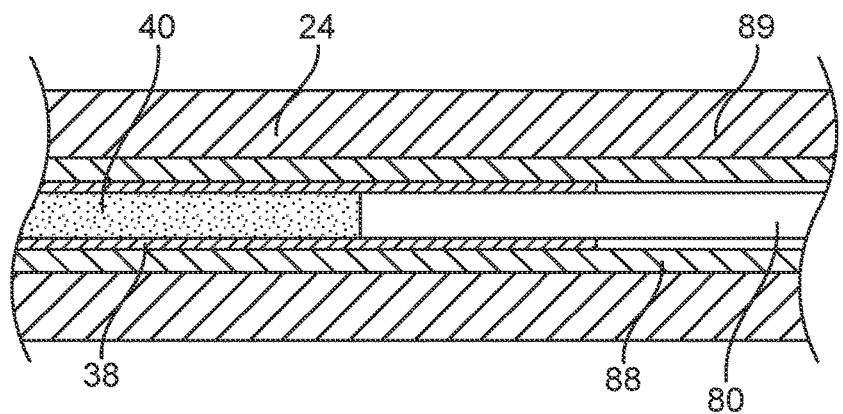
FIG. 7 is an enlarged view of the encircled portion 7 of the laser connector ferrule embodiment of FIG. 6.

The input window 80 and output window 82 enclosing the fluid volume 40 of the fluid core ablation catheter 22 generally include a material with a high transparency to the ultraviolet high power light pulses from the excimer laser or other suitable high power laser sources. The input optical window 80 as shown in FIG. 6 extends past the interface with the multi-layer catheter tube 38 in order that input laser energy spill over from an associated optical coupler 20 does not impinge on the multi-layer catheter tube 38 which could be heated and damaged. A tubular capillary shield 88 (see FIG. 6) may also be placed over the elongated cylindrical window 80 to further shield the catheter tube 38. The input optical window 80 may have a numerical aperture (NA) that is less than or matches the NA of the core fluid 40 of the ablation catheter 22 for optimum coupling in some cases. For some embodiments, the input optical window 80 may include a silica core silica clad window, but it may also include an optically polished silica rod that is radially surrounded by an air interface. The input optical window 80 of the ablation catheter 22 may also include a silica rod 90 (see FIG. 10) that has a low index amorphous fluoropolymer coating 91 such as Teflon AF 1601® or similar material applied to an outer surface thereof. For some embodiments, the input optical window 80 may have an outer diameter or transverse dimension of about 0.5 mm to about 1.5 mm, more specifically, about 0.8 mm to about 1.2 mm. The input window 80, capillary shield 88 and proximal end of the ablation catheter 22 are held in alignment and position for efficient coupling by a coupler body 89, as shown in FIG. 6, which includes a barrel member made from a high strength material with an inner lumen disposed therein. The proximal end of the ablation catheter 22 and distal end of the window 80 abut each other within the lumen of the barrel of the coupler body 89 as shown in FIG. 7. The capillary shield 88 may extend over the operative junction between the proximal end of the catheter tube 38 and distal end of the input window 80.

Figure 10:
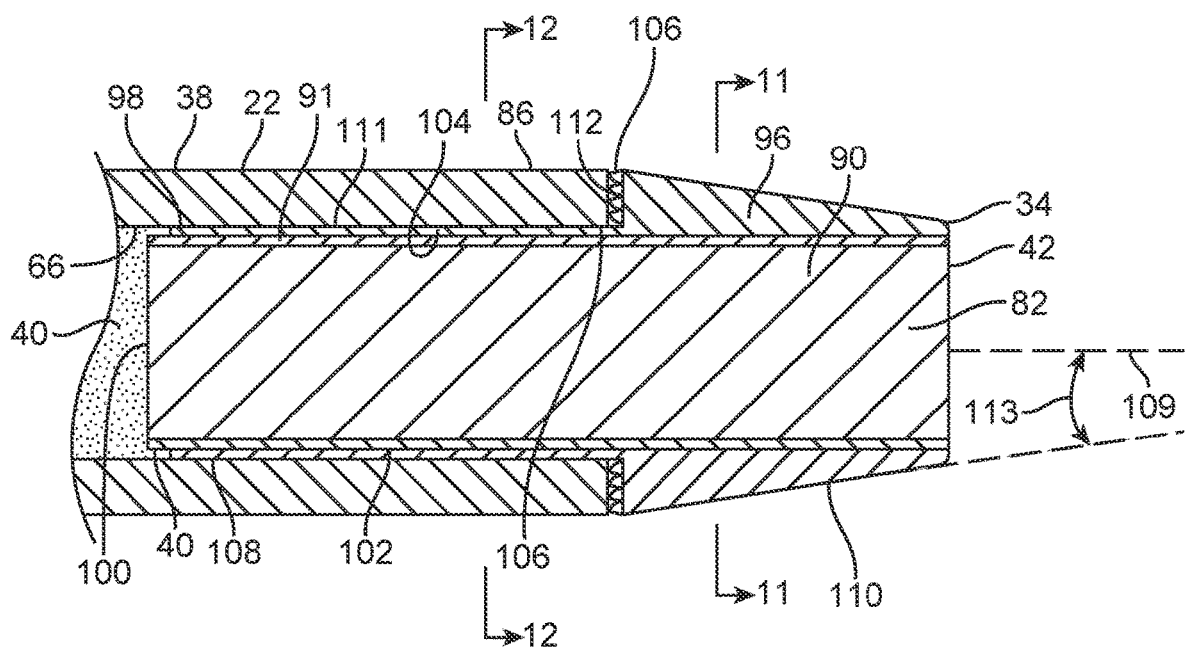
FIG. 10 is an elevation view in section of a distal portion of a liquid core ablation catheter embodiment including a tapered metal housing.
Figure 11:
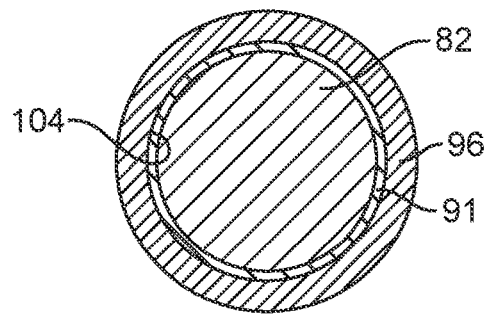
FIG. 11 is a transverse cross sectional view of the liquid core ablation catheter of FIG. 10 taken along lines 10-10 of FIG. 10.
Figure 12:
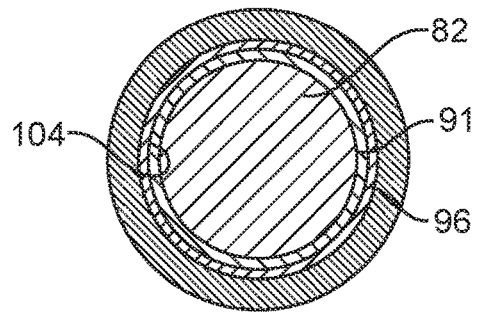
FIG. 12 is a transverse cross sectional view of the liquid core ablation catheter of FIG. 10 taken along lines 12-12 of FIG. 10.

The output optical window 82 as shown in FIG. 10 may have an overall length selected to minimize stiffness of the distal end 34 of the ablation catheter 22. In some cases, the output optical window 82 may have a length less than about 10 mm, more specifically, less than about 8 mm, even more specifically, less than about 6 mm, to allow the tip to negotiate curves in the body lumen. This output optical window 82 may have a numerical aperture equal to or greater than the numerical aperture of a tubular body portion of the liquid core ablation catheter 22 for maximum coupling of laser energy out of the liquid core 40. This output optical window 82 again may include a high NA optical fiber or a silica rod 90 coated with a low index amorphous fluoropolymer coating 91. For some embodiments, the output optical window 82 may have an outer diameter or transverse dimension of about 0.5 mm to about 1.5 mm, more specifically, about 0.8 mm to about 1.2 mm.

In order to protect the output optical window 82 from stresses and to ease passage of the fluid filled ablation catheter 22, a tapered metal housing 96 may be used to encapsulate the output optical window 82 as shown in the embodiment of FIG. 10. The output window 82 assembly at the distal end 34 of the ablation catheter 22 may be arranged with the proximal end 100 of the output optical window 82 extending proximally beyond a proximal end 98 of the tapered metal housing 96. The proximal end 100 of the output optical window 82 may extend proximally slightly into the core liquid 40 of the ablation catheter 22 in some cases as shown in FIG. 10. The tapered metal housing 96 may include an inner bore that extends the length of the tapered metal housing 96 from a proximal end to a distal end thereof. An inside surface 104 of the inner bore may be sized to fit closely with an outer surface 102 of the coating 91 of the output optical window 82 in some cases such that the output optical window 82 is stabilized laterally relative to the tapered housing but with enough gap to allow materials such as adhesives to extend therein. In some instances, the tapered metal housing 96 may be secured to the output optical window 82 by any suitable means such as by crimping, adhesive bonding, brazing, soldering or the like. In some cases, the tapered metal housing 96 may be so secured such that there may be little to no gap between the inside surface 104 of the inner bore of the tapered metal housing 96 and the outer surface 102 of the coating 91 output optical window 82. The tapered metal housing 96 may include a tapered distal section 110 that tapers down in outer diameter or dimension from a nominal outer diameter. The tapered distal section 110 may taper down to a reduced diameter or transverse dimension that may be up to about 0.012 inches larger than an outer transverse dimension or diameter of the output optical window 82. In some cases, the tapered distal section 110 may have a wall thickness at the distal end of the tapered distal section 110 of about 0.003 inches to about 0.005 inches. The tapered metal housing 96 may also include a stepped portion 111 that extends proximally from a proximal shoulder surface 112 of the tapered distal section 110.

The stepped portion 111 may have a thin wall disposed between the inner bore and an outer surface 108 that has an outer transverse dimension or diameter that is small enough to be pushed into the inner lumen of the multi-layer catheter tube 38. In some cases, the wall thickness of the stepped portion 111 may be about 0.002 inches to about 0.006 inches, more specifically, about 0.003 inches to about 0.004 inches.

An outer surface 102 of the coating 91 of the output optical window 82 may be bonded to the inside surface 104 of the metal housing 96 with any suitable adhesive 106, such as a medical grade class VI adhesive. The inside surface 104 of the metal housing 96 may also be secured to the outer surface 102 of the output optical window 82 by any suitable method including crimping, adhesive bonding, soldering, brazing or the like depending on whether the window 82 is an all glass embodiment or polymer coated embodiment. The outer surface 108 of the stepped portion of the metal housing 96 may be secured to a surface such as an inner luminal surface 66 of the catheter tube 38 by bonding, such as adhesive bonding, or any other suitable method. The tapered distal section 110 of the metal housing 96 may provide for a more efficient cutting tip during the laser ablation process in that the configuration may provide for more active cutting area relative to the non-cutting area at the distal end of the ablation catheter embodiment 22. In addition, the tapered end 110 of the metal housing 96 may facilitate passage of the ablation catheter 22 through a lumen created by the laser ablation process. For some embodiments, an outer surface of the tapered end or section 110 may form an angle with respect to a longitudinal axis 109 of the ablation catheter 22 indicated by arrow 113. The angle 113 of the tapered end 110 of the metal housing 96 may be up to about 5 degrees in some cases, more specifically, about 1 degree to about 2 degrees, for some embodiments. In other embodiments, the angle 113 may be up to about 8 degrees, more specifically, about 6 degrees to about 8 degrees. Further, the metal housing 96 may provide mechanical support and strength to the output optical window 82 which may be made from brittle or relatively fragile materials, such as quartz, silica or the like. The tapered metal housing 96 may be made from a single piece of high strength metal such as stainless steel, NiTi, titanium or the like. Depending on the metal material of the tapered metal housing 96, the tapered metal housing 96 may be visible under fluoroscopic imaging and may be configured to serve as a radiopaque marker for the distal end of the liquid core ablation catheter 22. Other metals such as gold, tantalum, platinum or the like may also be included in the tapered metal housing 96 in order to facilitate radiopacity of the tapered metal housing 96.

Figure 58:
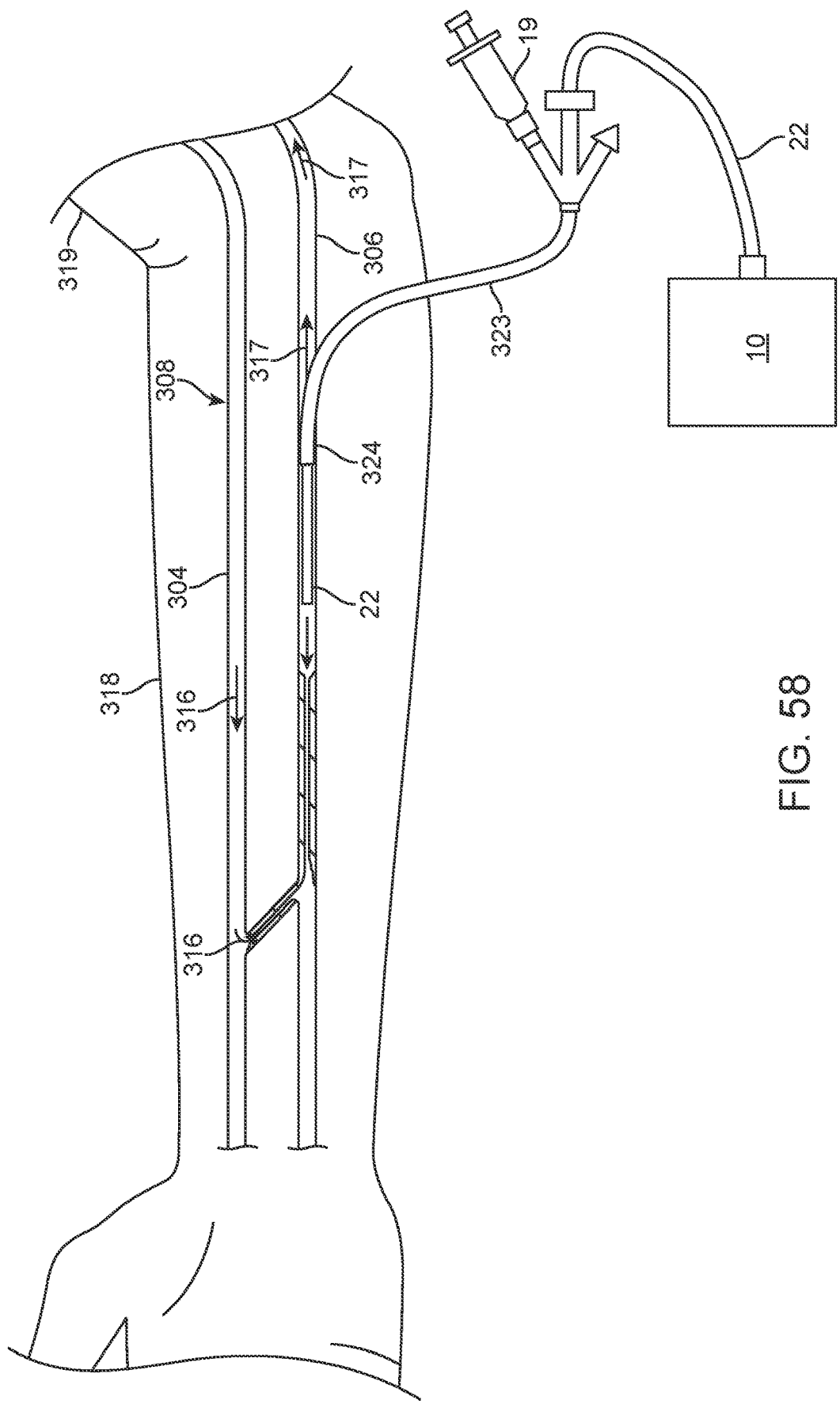
FIG. 58 illustrates the introduction of a guided laser ablation catheter being advanced within a vein towards the arteriovenous fistula.

Specific examples for use of the liquid core ablation catheter 22 are discussed herein that are directed to clearing obstructions in peripheral arteries of a patient, but similar approaches may be used for coronary arteries and other lumens 118 in the human body. Additionally, the unique problems of stenosed AV fistulas can be addressed with similar catheters that use liquid filled UV ablation catheter designs with various guidance methods. To initiate a percutaneous procedure, a short introducer sheath 323 may be placed into an artery of the groin of a patient or a fistula vein (as shown in FIG. 58). All other devices may generally be introduced through this introducing catheter, which may include a hemostatic valve to eliminate blood flow out of the introducing catheter during the procedure. Contrast fluid may be introduced through this introducer sheath or a longer introducing catheter may be inserted through the sheath over a guide wire 56, as shown in FIG. 31, to locate this catheter near a target lesion 116 disposed within the patient's anatomy.

Figure 28:
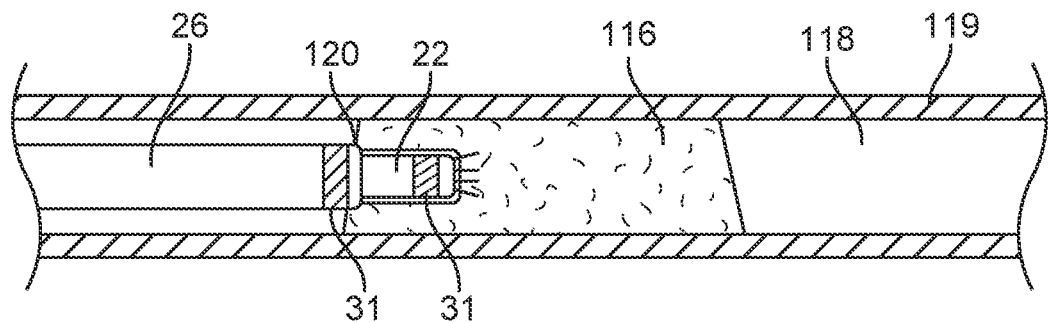
FIGS. 28 through 32 illustrate a method embodiment of an ablation method embodiment.

In some cases, a method embodiment for using a liquid core ablation catheter system 22 may include placing the low profile support catheter 26 through the introducing sheath and advancing the support catheter 26 distally into close proximity to a target lesion or material 116 as shown in FIG. 28. In some instances, the support catheter 26 may be advanced, guided or positioned over a guidewire 56 during this process. If a guiding device such as a guidewire 56 is used for advancing the support catheter 26, the guidewire 56 may then be removed once the distal end 120 of the support catheter 26 is disposed adjacent a target site or lesion 116. Once the guidewire 56 is removed from the inner lumen 28 of the support catheter 26, the liquid core ablation catheter 22 advanced distally within the inner lumen 28 of the support catheter 26 to the target lesion 116 as shown in FIG. 28. Saline may then be flushed through the inner lumen 28 of the support catheter 26 and around an outer surface of the liquid core ablation catheter 22 to remove blood from the tip of the ablation catheter 22. The laser source 10 may then be energized by depressing the footswitch 16 and laser energy at a level sufficient to ablate tissue then be emitted from the distal end 34 of the ablation catheter 22.

Figure 4:
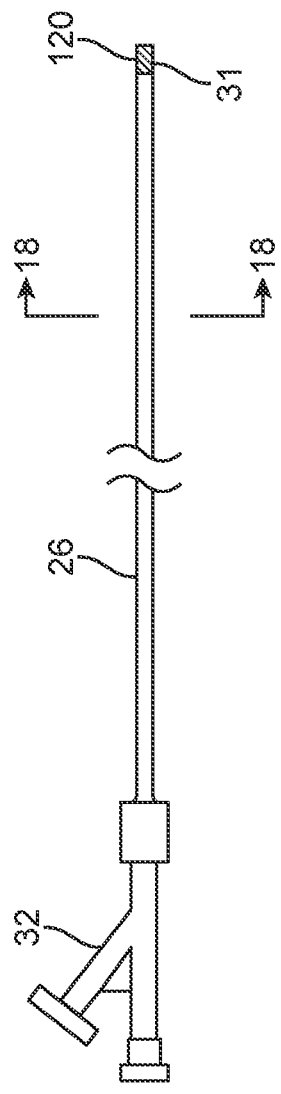
FIG. 4 is an elevation view of the support catheter embodiment of FIG. 2.
Figure 5:
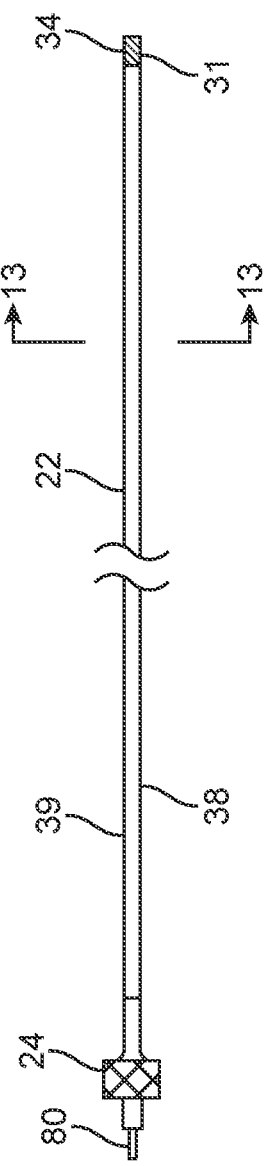
FIG. 5 is an elevation view of the liquid core ablation catheter embodiment of FIG. 2.
Figure 29:
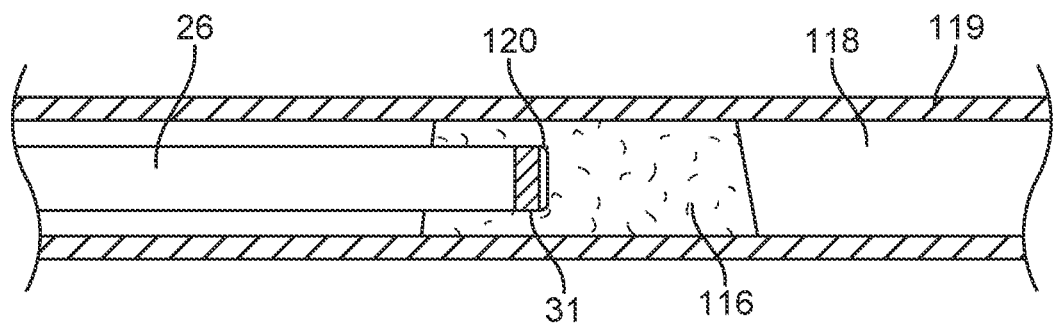
Figure 30:
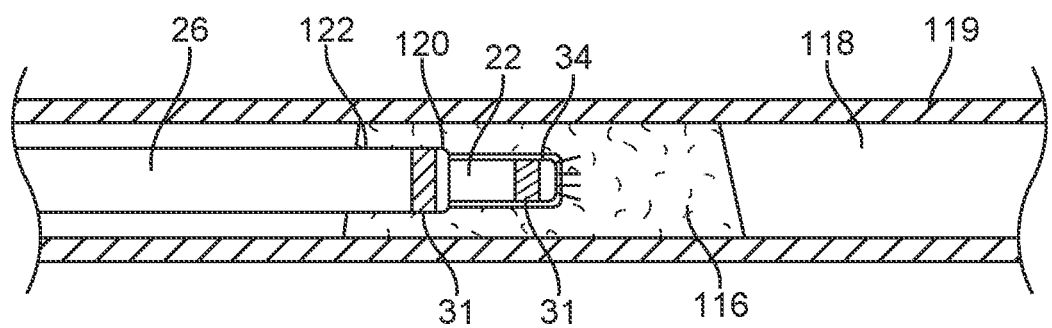
Figure 32:
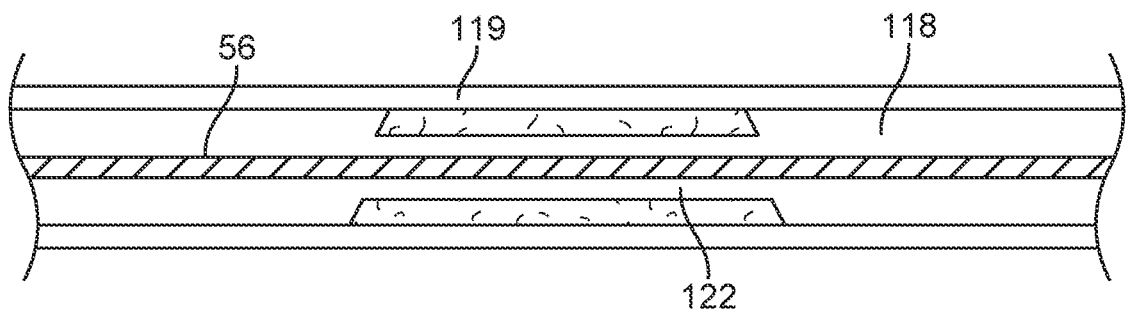

Upon activation of the laser, the distal end of the ablation catheter 22 may be advanced distally in an axial orientation into the target lesion 116 by a distance of about 5 to 10 mm for some embodiments, while the support catheter 26 remains substantially stationary with regard to its axial position. The support catheter 26 may then be advanced distally over the ablation catheter 22 and through the lumen 122 created by the active ablation catheter 22 until the distal tip 120, as shown in FIG. 4, of the support catheter 26 is substantially even with the distal tip 34 of the ablation catheter 22 as shown in FIG. 29. The relative positions of the respective distal ends 120 and 34 of the support catheter 26 and ablation catheter 22 may be determined by fluoroscopic imaging of the respective radiopaque marker bands 31 at the respective distal ends 120 and 34. The process is repeated as shown in FIG. 30 until the ablation catheter 22 crosses the lesion 116 as shown in FIG. 31. The ablation catheter 22 is removed with the support catheter 26 left in place and a guidewire 56 is advanced though the newly created channel or lumen 122. The support catheter 26 may then be retracted as shown in FIG. 32. Other devices, such as a balloon or a stent, may then be deployed over this guidewire 56 to achieve the necessary opening diameter in the vessel for adequate blood flow. If the laser catheter 22 produces a sufficient lumen 122, then no further treatment with additional devices is required in some instances.

For such a procedure, the support catheter 26 may be configured to have a low profile with thin walls to be able to follow the ablation catheter 22 through the lesion 116 and maintain the ablation end parallel to the lumen 122 to prevent perforation. To achieve this, the support catheter 26 may be a multilayer design with a thin wall liner 124 of a low friction Teflon®, such as polytetrafluoroethylene (PTFE) to allow passage of the ablation catheter with ease. An embodiment of the structure of a suitable support catheter is shown in FIG. 18.

Referring to FIG. 18, this liner 124 of the support catheter 26 may have an over layer or base layer tube 126 then a metal braid layer 128 disposed or braided over the base layer tube 126 to achieve pushability and kink resistance and torque. The base layer disposed over the PTFE liner 124 may have a high durometer with a very thin coating and an ideal material may include a polyimide base layer tube 126 covered with a thin over-jacket 130 of a lower durometer material for flexibility over the braid material layer 128. A wall thickness of the support catheter 26 of less than about 0.005" may be used for low profile for passage of the support catheter 26 through the opening or lumen 122 made by the liquid core ablation catheter 22. In essence this method may produce a result which is equivalent to a result achieved by using an external guidewire 56 for location of a cutting tip of an over-the-wire type design of the ablation catheter 22 as shown in FIGS. 15 and 16. The inner lumen 28 of the support catheter 26 may also include sufficient space or cross sectional area to accommodate both the ablation catheter 22 and a lumen or longitudinal space therebetween for flow of saline. A flow of saline or other desired fluid between an outside surface of the liquid core ablation catheter 22 and an inside surface of the inner lumen 28 of the support catheter 26 may be used to clear the blood which is disposed at the target lesion 116 site. In some cases, the saline may be introduced into the inner lumen 28 of the support catheter 26 with a syringe 19, as shown in FIG. 1, coupled to the Y connector 32 of the catheter system 27 as shown in FIGS. 1 and 2.

Some support catheter embodiments 26 may be straight as shown in FIG. 19 or have an angled tip as shown in the support catheter embodiment of FIG. 21 depending on the vessel contour at the lesion site. The support catheter 26 may have a low friction lubricious outer coating 132 on an outer surface 134 thereof (as shown in FIG. 18) for low friction passage though tissue follow the ablation catheter 22 through the lumen 122 created by the ablation catheter 22 through the target lesion 116. Visualization of the location of both the support catheter 26 and the ablation catheter 22 in the vessel lumen 118 and with respect to each other may be made by means of one or more radiopaque markers 31 or 136 disposed on the respective catheters at desired locations and with a least one marker located at each distal tip (120 and 34 respectively) of the catheters.

Interventional physicians often rely on a guidewire 56 for advancing multiple devices to treat a lesion 116 within a patient's vasculature and to maintain the position of a catheter inside the lumen walls. Some method embodiments discussed herein may include the use of a guidewire 56 to advance and/or position the support catheter 26. Once the support catheter 26 is properly positioned at a desired site within the patient's body, the guidewire 56 may then be removed and replaced with an ablation catheter such as the liquid core ablation catheter 22. Some interventionalist's may prefer the protection of a guidewire 56 to place other devices over in case of adverse event. In such cases, the ablation catheter 22 may be removed and a guidewire 56 inserted through the inner lumen 28 of the support catheter 26 and other treatment devices may then be passed over the guidewire 56 through the inner lumen 28 of the support catheter 26. In addition, the support catheter 26 may be removed before inserting other devices in some cases. One or more separate guidewire lumens 60 and 62 may also be attached to or integral with the support catheter 26 as shown on the support catheter embodiment 26''' of FIGS. 26 and 27. Additionally, a guidewire lumen may be added to the ablation catheter 22' as shown in FIGS. 15 and 16.

In some cases, a separate guidewire lumen 60 or any of the guidewire lumens discussed herein may be suitable for passage of a 0.014" sized guidewire or the like may be used for additional protection. In some cases, this guidewire lumen would only have a short length at the distal end for a rapid exchange type configuration. This configuration could apply to the both the ablation catheter 22' and the support catheter 26'''. That way the physician would always have a guidewire present in case of an adverse event and has the ability to withdraw the liquid core ablation catheter 22 and advance a guidewire 56 over a total occlusion after the dense cap entrance to the total occlusion is cleared by energy emitted from the liquid core laser ablation catheter 22 as shown in FIG. 32. For some embodiments, the guidewire lumens 60 and 62 may have a length of at least about 10 cm. In addition, the respective distal ports of the guidewire lumens 60 and 62, which may be disposed along an outer surface of support catheter embodiments 26''', may be disposed proximally from a distal end of the support catheter 26''' by at least about 5 mm.

For some embodiments, a support catheter such as the support catheter 26''' may have multiple guidewire lumens 60 and 62 as shown in the embodiment of FIGS. 26 and 27, a support catheter such as the support catheter 26'' may have a tapered distal section as shown in the embodiment of FIG. 20, and the support catheter 26' may have a bend at the end as shown in the support catheter embodiment of FIG. 21 to negotiate bends in the artery or to displace the ablation catheter 22 towards an eccentric plaque. The multiple guidewire lumens 60 and 62 may be used for saline flush, contrast injection or for passage of a guidewire 56 in some cases.

Figure 33:
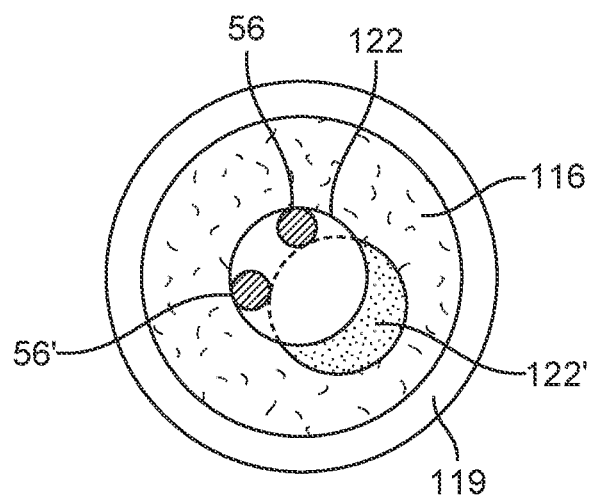
FIG. 33 is a transverse section view of a patient's vessel illustrating a method embodiment of producing a larger lumen after a first pass of an ablation catheter.
Figure 34:
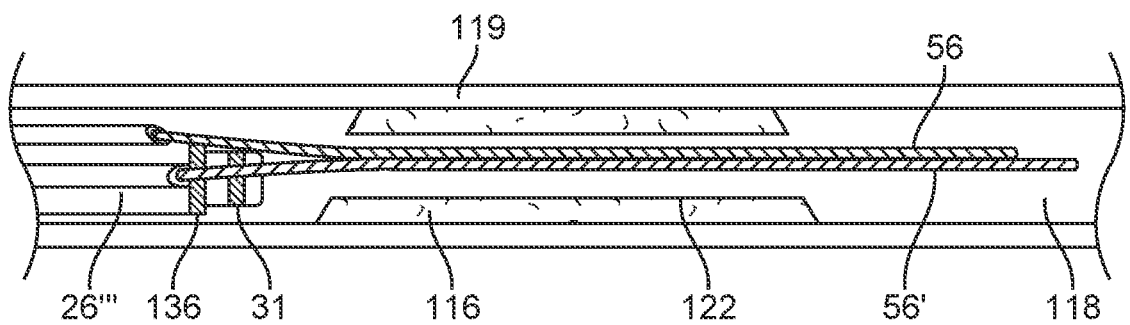
FIG. 34 is an elevation view in partial section of a patient's vessel lumen and catheter system embodiment disposed therein.
Figure 35:
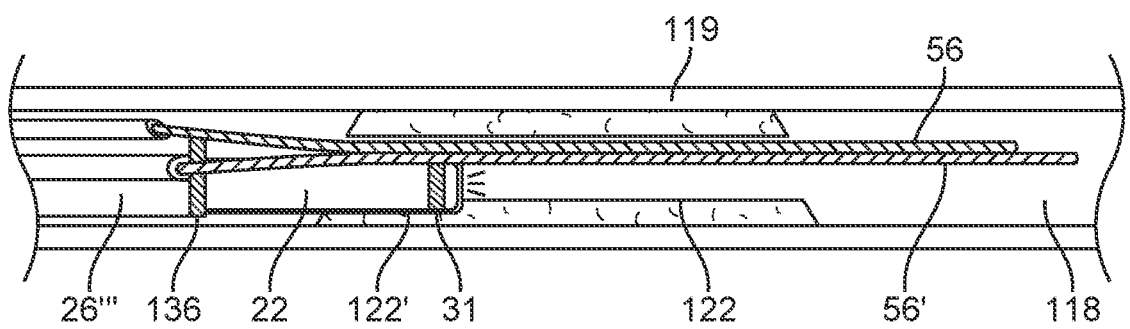
FIG. 35 is an elevation view in partial section illustrating an ablation catheter ablating additional material laterally adjacent the pilot lumen.

For some indications, it may be desirable to make a channel in a patient's vessel lumen that is larger in transverse dimension than a transverse dimension of the ablation catheter 22 itself. For some such cases, after the liquid core ablation catheter 22, or any other suitable ablation catheter embodiment discussed herein, forms an initial channel and opens an occlusion 116 in a patient's vessel 118, a guidewire 56 or other device may then be inserted in the opening or newly formed channel 122. The ablation catheter 22 may then be activated to emit ablation energy and advanced through the initial channel 122 adjacent the substantially parallel guidewire 56 to produce a lumen 122' which is larger than the lumen made with the first active pass of the ablation catheter 22. Such a technique embodiment is shown in FIGS. 33-35. Embodiments of this procedure may be completed with a second guidewire 56' in a second guidewire lumen 60 or 62 of a support catheter embodiment 26''' and a final pass made. This method may produce a lumen 122' having a larger inner transverse dimension or diameter and corresponding larger transverse cross section than an outer transverse dimension or diameter or cross section of the ablation catheter 22 used to make the initial channel 122. During this type of method embodiment, the guidewire placements after the first or initial lumen is made block part of the initially created lumen which laterally forces the distal end of the liquid core ablation catheter 22 up against the remaining plaque 116. Such partial filling the first or initial channel with one, two, three or more guidewires 56 and 56' forces the ablation catheter 22 to ablate tissue disposed laterally with respect to the initial channel 122 formed by the ablation catheter 22. Without the guidewire placement in the initial channel 122, the ablation catheter 22 would likely just go through the first or initial lumen 122 on a second pass with no further ablation or channel widening or increase in cross sectional area. Such an increase in cross sectional area of the ablation channel allows more blood or other fluid to flow therethrough for a fixed pressure.

Figure 37:
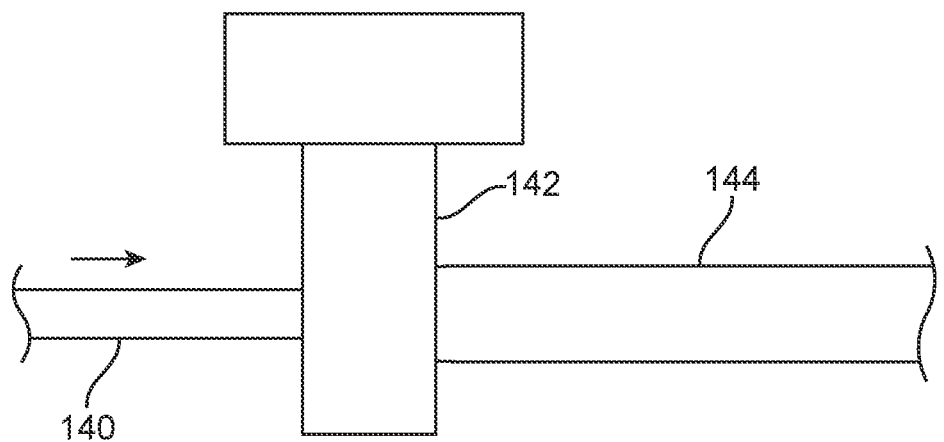
FIGS. 37 through 43 illustrate schematic representations of various catheter manufacturing process embodiments.
Figure 38:
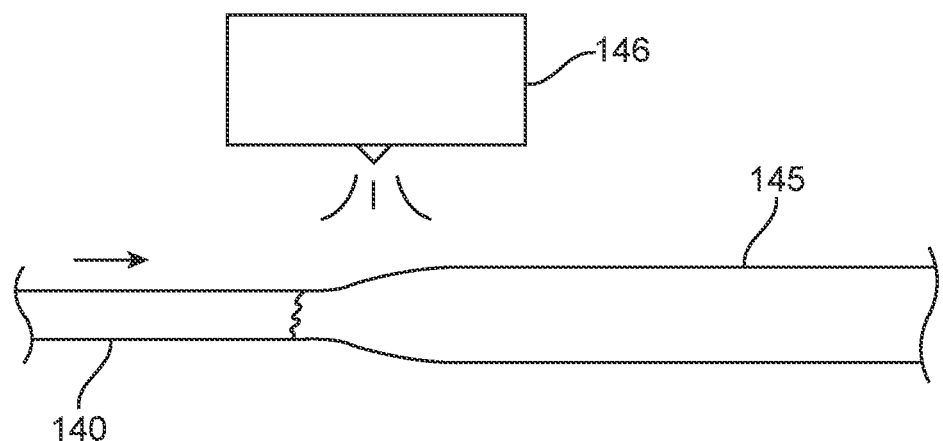
Figure 39:
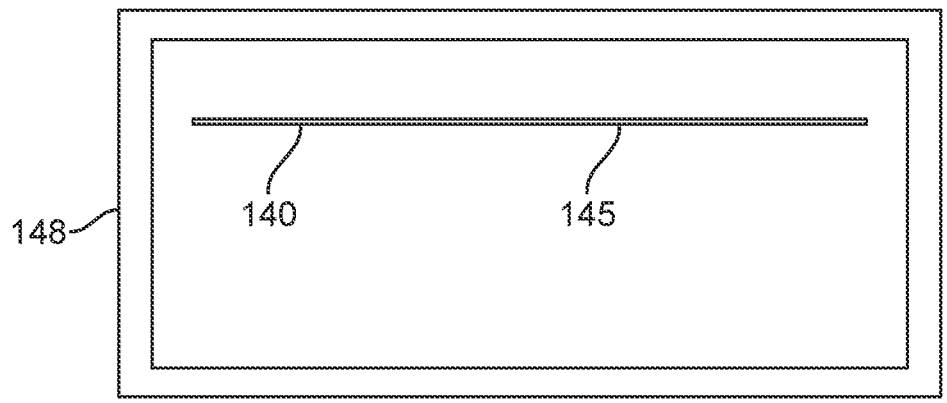
Figure 40:
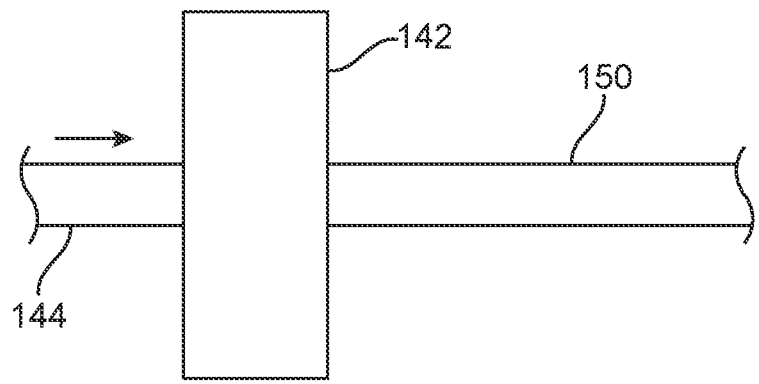
Figure 41:
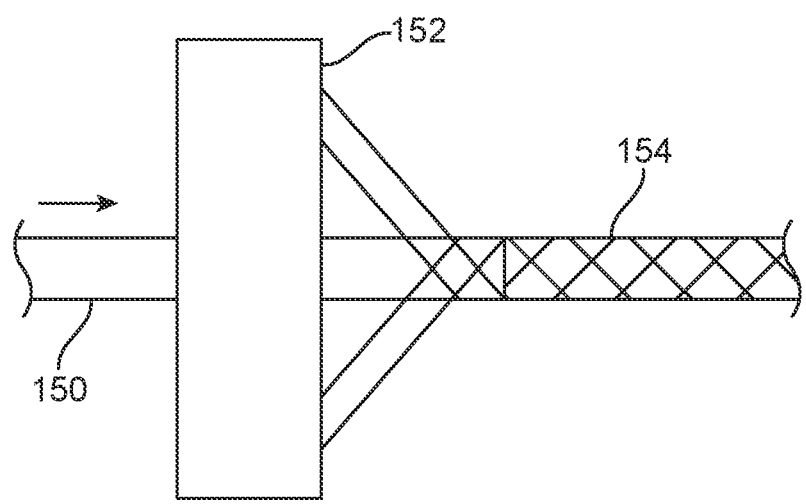
Figure 42:
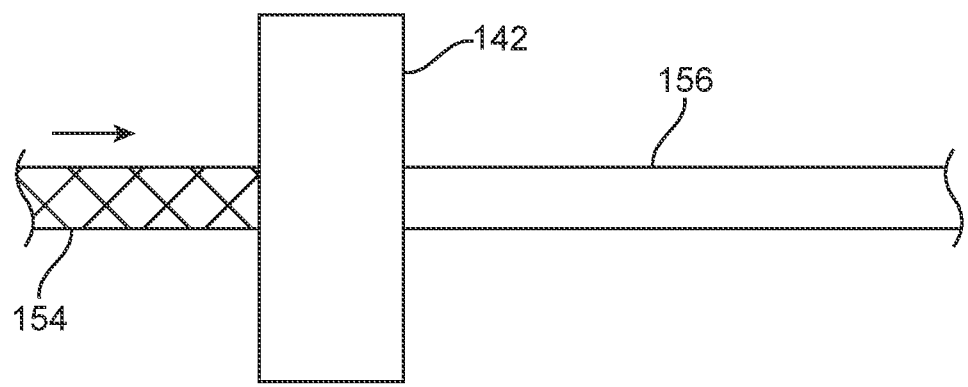
Figure 43:
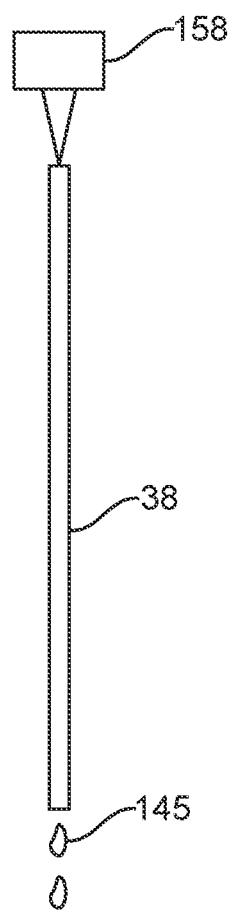

Referring to FIGS. 37-42, a variety of manufacturing steps are shown which may be useful for some or all of the processing method embodiments discussed above. In particular, FIG. 37 illustrates a polished metal mandrel 140 being passed through an extruder device 142 and applying a layer of amorphous fluoropolymer 144 to an outer surface of the mandrel 140. FIG. 38 shows a mandrel 140 having a solution of amorphous fluoropolymer 145 being applied to an outside surface of the mandrel 140 by a spray coating device 146 to produce a thin layer of amorphous fluoropolymer 144. FIG. 39 depicts a mandrel 140 with a coating of amorphous fluoropolymer solution 145 disposed in an oven 148 for thermal processing to drive off the solvent of the fluoropolymer solution 145. FIG. 40 shows a mandrel 140 with a layer of amorphous fluoropolymer 144 applied thereto being passed through an extruder 142 to apply a layer of base tube material 150. FIG. 41 shows the mandrel 140 of FIG. 40 with a layer of amorphous fluoropolymer 144 and subsequent base layer tube material 150 being passed through a braiding device 152 to apply a braided layer 154 to the base tube layer 150. FIG. 42 shows the mandrel 140 and layers 144, 150 and 154 being passed through an extruder 142 to apply an outer jacket layer 156. FIG. 43 shows an amorphous fluoropolymer solution 145 being injected into a catheter tube 38 by a pressurized amorphous solution source 158 which may be further processed to remove the solvent from the solution 145 in an oven 148 as shown in FIG. 39.

Figure 44:
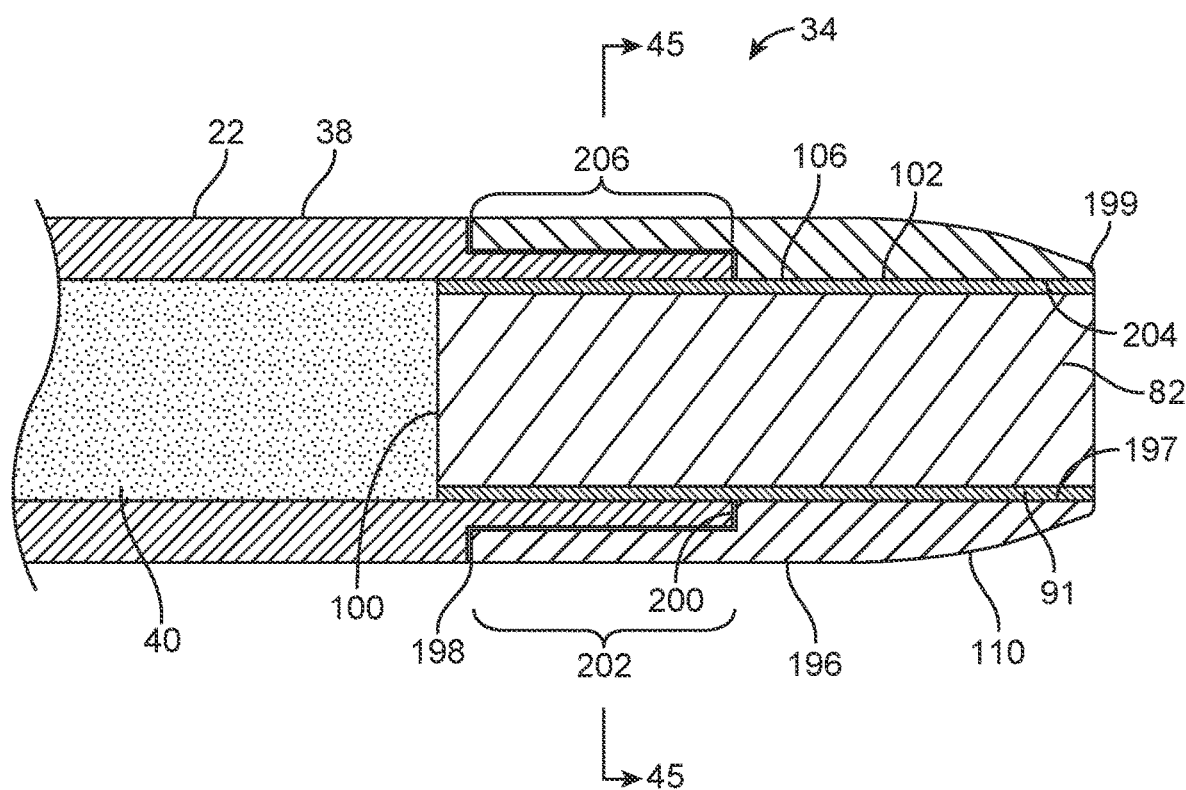
FIG. 44 is an elevation view in section of a distal portion of a liquid core ablation catheter embodiment including a tapered metal housing.
Figure 45:
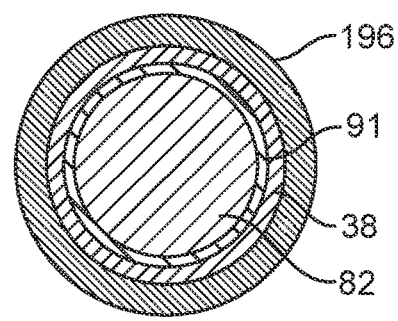
FIG. 45 is a transverse cross section view of the liquid core ablation catheter of FIG. 44 taken along lines 45-45 of FIG. 44.
Figure 46:
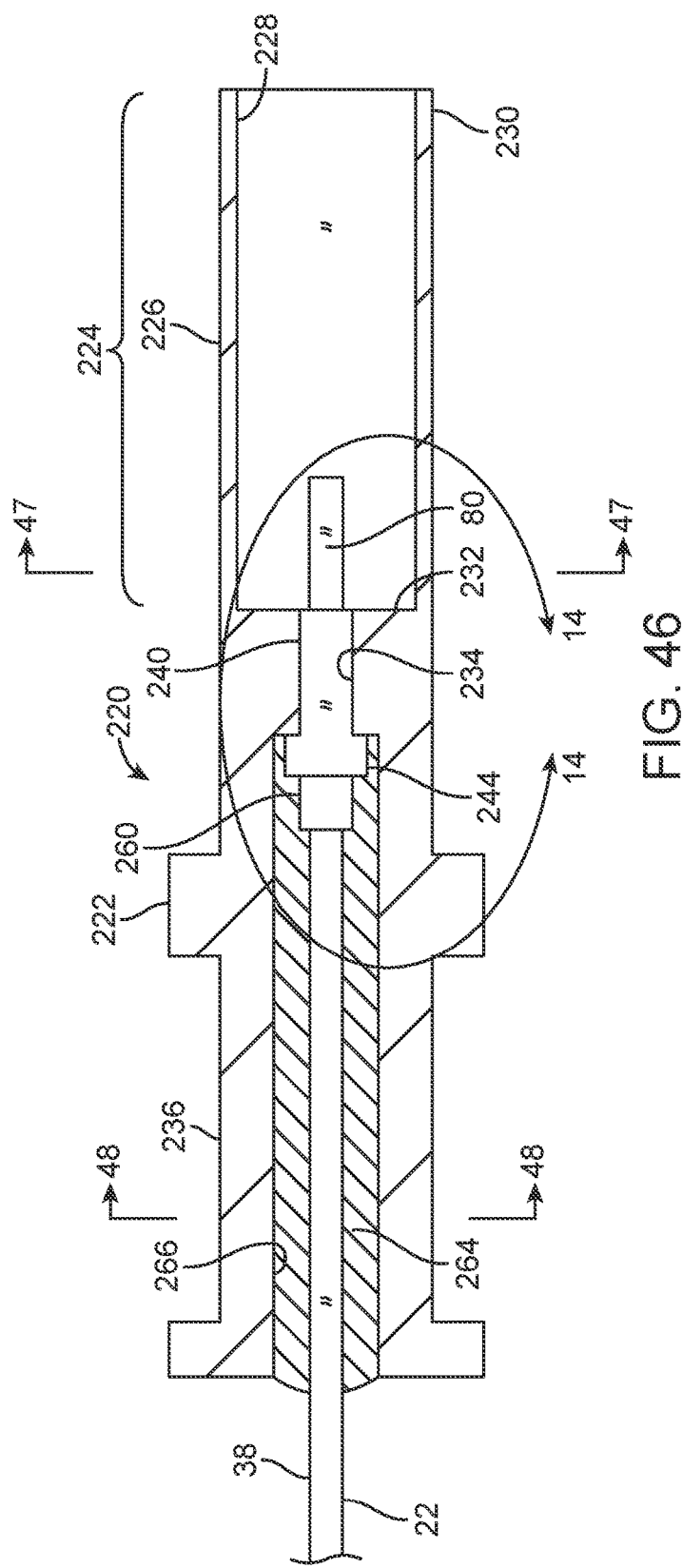
FIG. 46 is an enlarged elevation view in partial section of a laser connector ferrule embodiment of FIG. 3 for use with a liquid core ablation catheter.
Figure 48:
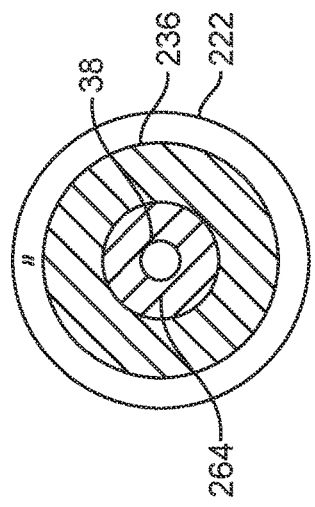
FIG. 48 is a transverse cross section view of the laser coupler of FIG. 46 taken along lines 48-48 of FIG. 46.
Figure 47:
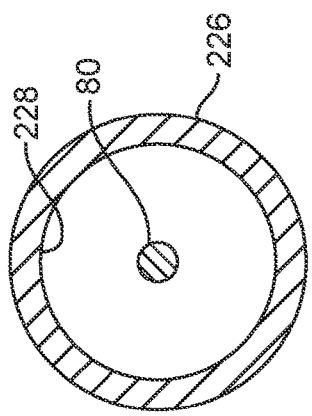
FIG. 47 is a transverse cross section view of the laser coupler of FIG. 46 taken along lines 47-47 of FIG. 46.

FIG. 44 shows a distal portion of an embodiment of a liquid core ablation catheter that may have some or all of the properties of liquid core ablation catheter 22 discussed above. Once again, in order to protect the output optical window 82 from stresses and to ease passage of the fluid filled ablation catheter 22 through tissue during ablation, a tapered metal housing 196 may be used to encapsulate the output optical window 82 as shown in the embodiment of FIG. 44. The output window 82 assembly at the distal end 34 of the ablation catheter 22 may be arranged with the proximal end 100 of the output optical window 82 extending proximally beyond a proximal end 198 of the tapered metal housing 196.

The proximal end 100 of the output optical window 82 may extend proximally slightly into the core liquid 40 of the ablation catheter 22 in some cases as shown in FIG. 44. The tapered metal housing 196 may include an inner bore 197 that extends the length of the tapered metal housing 196 in a proximal direction from a distal end 199 of the housing 196 to a distal end 200 of a stepped portion 202 of the housing 196. An inside surface 204 of the inner bore may be sized to fit closely with an outer surface 102 of the coating 91 of the output optical window 82 in some cases such that the output optical window 82 is stabilized laterally relative to the tapered housing but with enough gap to allow materials such as adhesives to extend therein. In some instances, the tapered metal housing 196 may be secured to the output optical window 82 by methods such as by crimping, adhesive bonding, soldering, brazing or the like. In some cases the tapered metal housing 196 may be secured such that there may be little to no gap between the inside surface 204 of the bore 197 of the tapered metal housing 196 and the outer surface 102 of the coating 91 of the output optical window 82. The tapered metal housing 196 may include a tapered distal section 110 that tapers down in outer diameter or dimension from a nominal outer diameter. The tapered distal section 110 may taper down to a reduced diameter or transverse dimension that may be up to about 0.012 inches larger than an outer transverse dimension or diameter of the output optical window 82, in some cases up to about 0.010 inches larger. In some cases, the tapered distal section 110 may have a wall thickness at the distal end 199 of the tapered distal section 110 of about 0.003 inches to about 0.005 inches. The stepped portion 202 of the housing 196 may have a thin wall disposed over a reduced diameter portion 206 of a distal section of the multilayer catheter tube 38.

In some cases, the stepped portion 202 of the tapered metal housing 196 may have the same or similar longitudinal length as that of the reduced diameter portion 206 of the distal section of the multilayer catheter tube 38. In some cases, the wall thickness of the stepped portion 202 may be about 0.002 inches to about 0.005 inches, more specifically, about 0.003 inches to about 0.004 inches. In some cases, the wall thickness of the reduced diameter portion 206 of the multilayer catheter tube 38 may be sized to have an overall outer diameter to substantially match an inside diameter or transverse dimension of the stepped portion 202 of the tapered metal housing 196. In addition, the inside surface of the stepped portion 202 may be secured to an outer surface of the reduced diameter portion 206 with an adhesive bond, crimp connection or the like. In some instances, it may be desirable for an outside diameter or transverse dimension of the tapered metal housing 196 to be the same as or substantially the same as an outside diameter or transverse dimension of the nominal multilumen catheter tube 38 so as to provide a smooth regular transition between an outside surface of the tapered metal housing 196 and an outside surface of the multilumen catheter tubing 38.

The outer surface 102 of the output optical window 82 may be bonded to an inside surface 204 of the metal housing 196 with any suitable adhesive 106, such as a medical grade class VI adhesive or the like. For all glass embodiments of the output optical window 82, methods such as soldering or bronzing may be used. The inside surface 204 of the bore 197 of the metal housing 196 may also be mechanically secured to the outer surface 102 of the output optical window 82 by methods such as crimping or any other suitable mechanical method as discussed herein. As discussed above, the tapered distal section 110 of the metal housing 196 may provide for a more efficient cutting tip during the laser ablation process in that the configuration may provide for more active cutting area relative to the non-cutting area at the distal end of the ablation catheter embodiment 22. In addition, the tapered end 110 of the metal housing 196 may facilitate passage of the ablation catheter 22 through a lumen created by the laser ablation process. For some embodiments, the tapered end 110 of the tapered metal housing 196 may have the same or similar configuration as that of tapered metal housing 96 discussed above and as shown in FIGS. 10-12. In particular, the tapered end 110 may form an angle 113 with respect to a longitudinal axis 109 of the ablation catheter 22 indicated by arrow 113 in FIG. 10 of up to about 5 degrees in some cases, more specifically, about 1 degree to about 2 degrees, for some embodiments. In some instances, the tapered end 110 of the tapered metal housing 96, or any other tapered metal housing embodiment discussed herein, may form an angle 113 of up to about 9 degrees, more specifically, of about 6 degrees to about 8 degrees. Further, the metal housing 196 may provide mechanical support and strength to the output optical window 82 which may be made from brittle or relatively fragile materials, such as quartz, silica or the like. The tapered metal housing 196 may be made from a single piece of high strength metal such as stainless steel, titanium or the like. Depending on the metal material of the tapered metal housing 196, the tapered metal housing 196 may be visible under fluoroscopic imaging and may be configured to serve as a radiopaque marker for the distal end of the liquid core ablation catheter 22. Other metals such as gold, tantalum, platinum or the like may also be included in the tapered metal housing 196 in order to facilitate radiopacity of the tapered metal housing 196.

FIGS. 46-50 illustrate an embodiment of a high energy laser coupler 220 that may be operatively coupled to a proximal end of any of the liquid core ablation catheters embodiments 22 discussed herein as well as any other suitable laser ablation catheter. For some embodiments, the high energy laser coupler 220 may include a coupler body 222 that has a proximal section 224 with a cylindrical outer surface 226 and an inner bore 228 which is disposed concentrically within the cylindrical outer surface 226. The inner bore 228 extends distally from a proximal end 230 of the coupler body 222 to a proximal end 232 of a window connector bore 234. The window connector bore 234 is disposed at a distal end of the inner bore 228. The coupler body 222 also includes a distal section 236 extending distally from the window connector bore 234.

A window connector body 240 includes a proximal section 241 with a cylindrical outer surface which may be configured to fit closely within an inside surface of the window connector bore 234 of the coupler body 222. A flange portion 244 of the window connector body 240 is disposed at a distal portion or distal end of the proximal section 241 and extends radially outward from a nominal outer surface 246 of the proximal section 241 of the window connector body 240. The window connector body 240 also includes a stepped portion 250 which extends distally from the proximal portion and has an outer diameter or transverse dimension that is less than an outer diameter or transverse dimension of the proximal section 241 of the window connector body 240. The outer diameter of the stepped portion 250 may be configured to extend within an inner lumen of a proximal section of the multilayer catheter tube 38. An outer surface 252 of the stepped portion 250 may be secured to an inside surface of the proximal section of the multilayer catheter tube 38 by an adhesive bond, crimp bond or the like. An inner bore 254 extends the length of the window connector body 240 from a proximal end 242 to a distal end 245 thereof. The inner bore 254 may be a straight bore that is configured to fit closely with an outer surface 256 of an optical input window 80 disposed within and secured to the inner bore 254 of the window connector body 240. The outer surface 256 of the optical input window 80 may be secured to an inside surface of the inner bore 254 of the window connector body 240 with an adhesive bond, crimp bond, solder bond, braze bond or the like. In some cases, it may be desirable for the bond between the outer surface 256 of the input optical window 80 and the inside surface of the bore 254 of the window connector body 240 to be fluid tight.

In some instances, a proximal end of the optical input window 80 may extend proximally from a proximal end 242 of the proximal section 241 of the window connector body 240. As shown in FIGS. 49 and 50, a proximal portion of the flexible waveguide catheter tube 38 is disposed over the stepped portion 250 of the window connector body 240 with a cylindrical metal sleeve 260 disposed over the proximal portion of the flexible waveguide catheter tube 38. The cylindrical metal sleeve 260 may be disposed so at to secure an inside surface of the catheter tube 38 to an outside surface of the stepped portion 250 of the window connector body 240 in a fluid tight seal. The inside surface of the multilayer catheter tube 38 may be secured to an outside surface of the stepped portion 250 with an adhesive bond 263. In some cases, an inside surface 262 of the metal sleeve 260 may be secured to an outside surface of a proximal portion 267 of the multilayer catheter tube 38 with an adhesive bond 263, with a crimp body or the like. In addition, a potting material 264 such as an adhesive or the like may be used to provide mechanical support and strain relief between an outer surface of the multilayer catheter tube 38 and an inside surface of a back bore 266 of the distal section of the coupler body 222.

The optical input window 80 may include a length of multi-mode optical fiber in some instances. In some embodiments, the optical input window 80 may extend distally of a distal end 245 of the stepped portion of the window connector body 240 making direct contact with liquid core fluid 40 of the liquid core ablation catheter. In some instances, the optical input window may have axial length of about 0.5 inches to about 1 inch. For some embodiments, the stepped portion of the window connector body may have a wall thickness of about 0.002 inches to about 0.004 inches.

Figure 51:
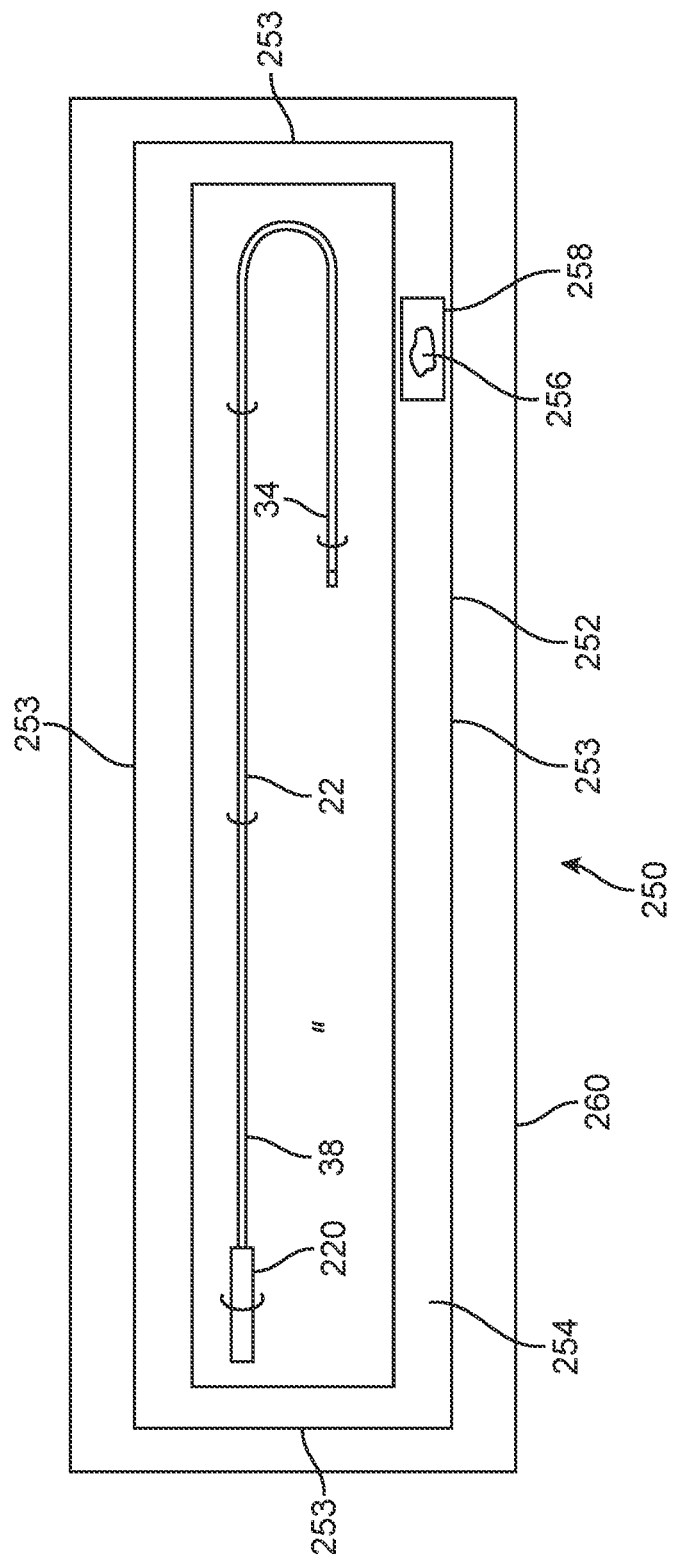
FIG. 51 shows a schematic representation of a packaging embodiment for use with a liquid core ablation catheter.

Regarding packaging and transportation of liquid core ablation catheter embodiments discussed herein, certain conditions or structures may be desirable in order to keep the catheter embodiments in good working order. In some cases, it may be important to maintain a minimum vapor pressure of liquid in the environment surrounding some liquid core ablation catheter embodiments 22 in order to prevent loss of core fluid 40 during storage or transportation of the catheter 22 due to diffusion through the catheter tube 38 (see FIG. 7). It may also be important to minimize temperature extremes to which some liquid core ablation catheter embodiments are exposed. FIG. 51 shows a liquid core ablation catheter package assembly 250 that includes a thin walled hermetically sealed enclosure 252 including an interior volume 254. In some cases, a material of the enclosure 252 may be suitable for gamma sterilization. A liquid core ablation catheter 22 is shown disposed within the interior volume 254 of the hermetically sealed enclosure 252, however, any suitable liquid core ablation catheter including any of the liquid core ablation catheters 22, 22' or the like, discussed herein may be so packaged. A second liquid 256 is disposed within the interior volume and is configured to maintain a vapor pressure within the interior volume 254 sufficient to prevent loss of a liquid 40 of a liquid core 40 of the liquid core ablation catheter 22 due to diffusion of the liquid core 40 into the interior volume 254. In some cases, it may be desirable to use a second liquid 256 which is soluble in or miscible with the liquid in the core 40 of the ablation catheter 22. Thus the liquid core 40 of the liquid core ablation catheter 22 may include the same liquid as that of the second liquid 256 or the liquid core 40 and second liquid 256 may be different liquids. The hermetic properties of the enclosure 252 prevents the second liquid 256 from escaping the enclosure 252, thus only a small amount of the second liquid 256 may be necessary. In some instances, the thin walled hermetically sealed enclosure 252 may be made from a thin metalized plastic or a non-metalized thin plastic such as PCTFE that functions as a suitable liquid vapor barrier in order to prevent escape of the second liquid 256 from the interior volume 254 of the enclosure 252. The thin walled plastic of the enclosure 252 may include heat sealed edges 253 in order to form the enclosure 252 from two flat thin sheets of the plastic material. The package assembly 250 may also include a liquid depot 258 that contains the second liquid 256 disposed within the interior volume 254. In some cases, the liquid depot 258 may include a sponge or the like that may also be configured to absorb a liquid such as the core liquid 40 and be suitable for gamma sterilization. In addition, the sealed enclosure 252 may be disposed within a substantially rigid box 260.

For some packaging methods and embodiments, the liquid core catheter embodiments 22, 22' and the like, discussed herein may be placed in a spiral tube 270 filled with a second liquid 256 and sealed at both ends of the spiral tube 270 as shown in FIGS. 52-54. In some cases, the spiral tube 270 may be releasably secured to cardboard type support sheet 271 with tabs 273 to hold the spiral tube 270 in the spiral configuration. This spiral tube container 270 is then sealed in an interior volume 272 of a hermetically sealed pouch 274. The hermetically sealed pouch 274 may include a hermetic metallized mylar heat sealed pouch 274, PCTFE pouch or other hermetic material. In some cases, the hermetically sealed pouch may be heat sealed along an entire edge at a seal line 275 as shown in FIG. 53. The hermetically sealed pouch 274 may then be placed in a rigid box 276 for sterilization and shipping. Examples of such embodiments are shown in FIGS. 52-54. In addition, multiples of the boxes 276 may be transported in insulated box containers i.e. Styrofoam lined boxes (not shown), to protect the catheters from temperature extremes during shipping.

Some particular package assembly embodiments to extend a shelf life of a liquid core catheter may include a liquid core catheter 22 comprising a core liquid 40, a polymer spiral tube 270 which includes an inner lumen 278 filled with a second liquid 256 that is soluble in or miscible with the core liquid 40 of the liquid core catheter 22 and which is sealed at both ends to contain the second liquid 256 in the inner lumen 278 of the polymer spiral tube 270, and a sealed pouch 274 which is made of either metallized plastic or polychlorotrifluoroethylene that acts as a hermetic seal for liquids disposed within the sealed pouch. The sealed pouch 274 may also include a hermetically sealed inner volume or lumen 272 with the polymer spiral tube and liquid core catheter 22 being disposed within the hermetically sealed inner volume 272.

In some cases, the spiral tube container 270 may include a first straight section 282 that extends away from a spiral portion of the polymer spiral tube 270. Such a straight section 282 may be useful for maintaining the straightness of an ablation catheter 22 disposed within the inner lumen 278 of the polymer spiral tube 270 for extended periods of time. In some cases, the straight section 282 may have a length that is about 10 cm to about 30 cm. A second straight section 284 may extend from the polymer spiral tube 270 at an end of the polymer spiral tube 270 that is opposite that of the first straight section 282. The second straight section 284 may also have a length of about 10 cm to about 30 cm for some embodiments. The second straight section 284 also includes a flared portion 286 at an end of the polymer spiral tube 270. The flared portion 286 has a flared internal lumen profile configured to provide a fluid tight seal 285 with an outside surface of a tapered strain relief 287 of the laser coupler 24' disposed within the inner lumen of the flared portion 286. The angle of the flared portion 286 maybe selected such that the outside surface of the tapered strain relief 287 seats in a sealed relation to the inside surface of the flared portion 286 when pushed into the flared portion 286. The laser connector 24' and tapered strain relief 287 may also be so seated such that it remains in fixed relation relative to the flared portion 286 during storage due to the static friction between the inside surface of the flared portion 286 and the outer surface of the strain relief 287 of the laser connector 24'. The sealed seating may also be facilitated by the elasticity of the material of the polymer spiral tube 270 at the flared portion 286. A user may unseat the laser connector 24' by merely pulling the laser connector 24' out of the flared portion 286. The end of the spiral tube 270 opposite that of the flared portion 286 is sealed with a cap 290 that is secured in fixed and sealed relation with the spiral tube 270. The spiral tube 270 may also be sealed at this location by any other suitable method such as adhesive bonding, heat sealing or the like.

Another way to reduce or prevent diffusion loss of core fluid 40 from a laser ablation catheter during storage is to select one or more materials for the multi-layer catheter tube 38 that are impervious to diffusion of the core liquid 40. As discussed above, some embodiments of a liquid core ablation catheter 22 may comprise a multi-layer catheter tube 38 including a fluoropolymer material and an internal coating 48 disposed on an inner surface of the catheter tube 38. In some cases, the internal coating 48 may include an amorphous fluoropolymer having a low index of refraction of less than about 1.34. The liquid core ablation catheter 22 may also have an outer layer 54 disposed on an outer surface 68 of the multi-layer catheter tube 38, the outer layer 54 including PCTFE material that acts as a barrier to liquid diffusion out of an inner lumen 46 of the catheter tube (see FIGS. 13 and 14). The base layer tube 50 may also include PCTFE material or the like which is impervious to diffusion of the core fluid 40. Such prevention of liquid diffusion may include prevention of water vapor diffusion. The liquid core ablation catheter 22 may also include a first solid window 80 that seals the inner lumen 46 at a first end of the catheter tube 38 and a second solid window 82 that seals the inner lumen 46 at a second end of the catheter tube 38 (see FIGS. 3 and 6).

Figure 55:
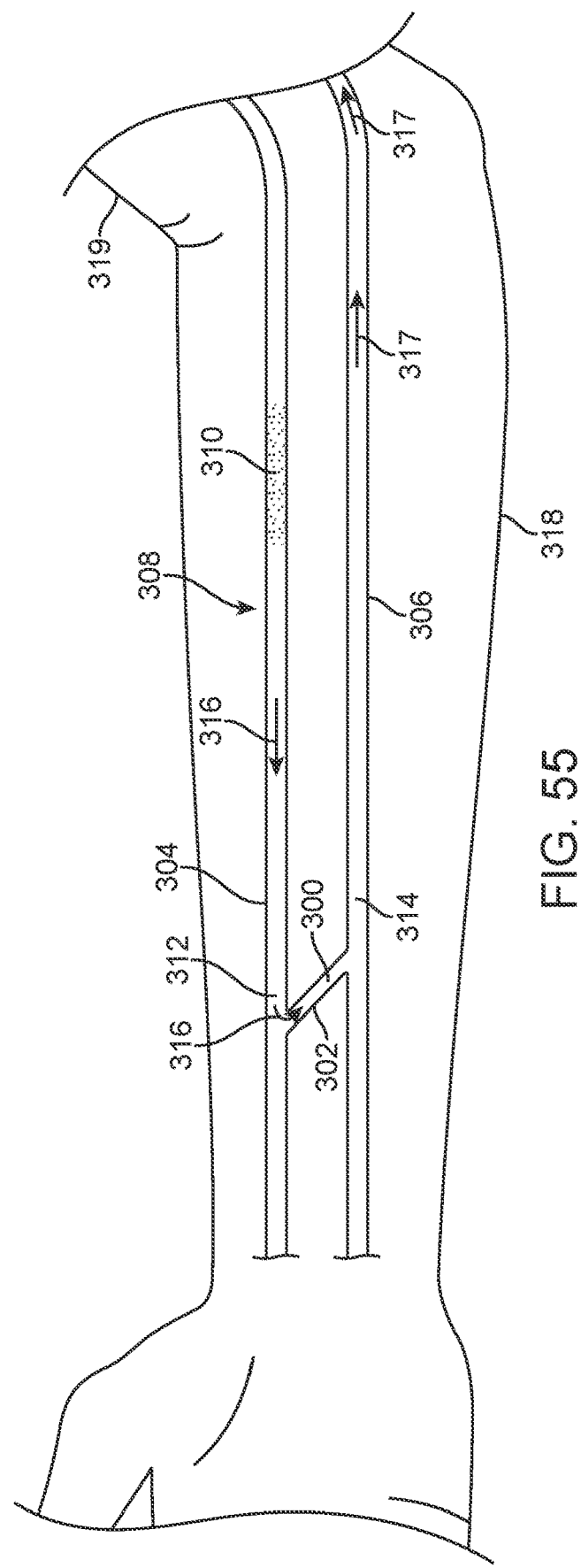
FIG. 55 is a schematic view of a patient's forearm showing an embodiment of an arteriovenous (AV) fistula formed between a vein and an artery of the patient's forearm by an arteriovenous graft.
Figure 55A:
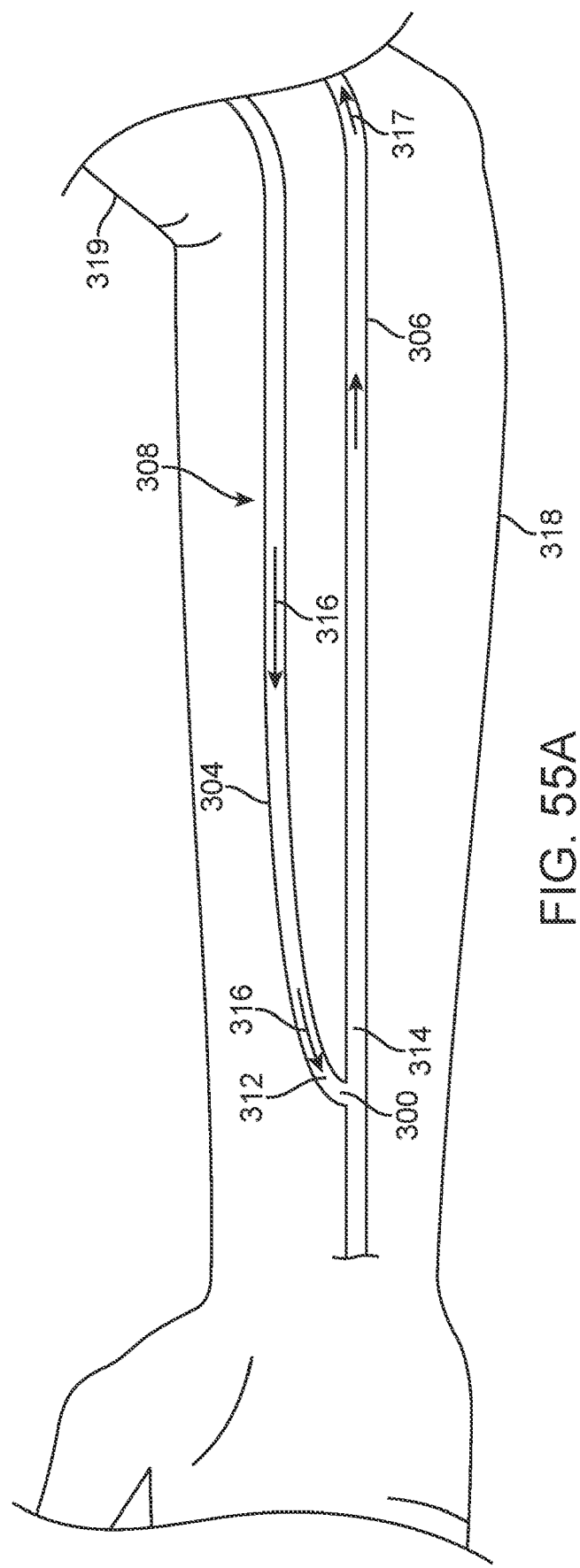
FIG. 55A is a schematic view of a patient's forearm showing an embodiment of an arteriovenous fistula formed between a vein and an artery of the patient's forearm without the use of an arteriovenous graft.

The systems and methods discussed above may be used to treat a wide variety of occlusive conditions in patient vessels including some that are difficult to treat by existing methods. A particularly difficult indication relates to vascular access required for dialysis procedures. Kidney dialysis is performed by accessing a patient's vasculature in order to provide circulation of the patient's blood to a dialyzer machine. Typically, access to the patient's vasculature for dialysis is achieved by placing a pair of dialysis needles into an AV fistula 300 of the patient or a suitable vessel adjacent an AV fistula as shown in FIGS. 55 and 55A. The AV fistula 300 may be created in the patient's body with a surgical procedure by forming an AV fistula graft (AVG) 302 as shown in FIG. 55 or by directly coupling a patient's artery 304 to a patient's vein 306 as shown in FIG. 55A. An AV fistula 300 may be useful because it causes the vein 306 to grow larger and stronger in the vicinity of the AV fistula 300 for easy access to the vascular system 308 of the patient. The AV fistula 300 is generally considered to be the best long-term vascular access modality for hemodialysis procedures because high pressure blood 310 in the vein 304 from the coupled artery provides adequate blood flow for dialysis and the AV fistula 300 generally remains useful for 1-2 years and has a lower complication rate than other types of dialysis access. If an AV fistula 300 cannot be created in a patient or a patient's AV fistula access site becomes unusable due to a blockage or some other reason, a venous catheter may be needed for dialysis access and such venous catheter access may have a high complication rate. It is estimated that over 300,000 patients are treated each year in the USA for these types of procedures, and with an aging population, a 9% growth rate per year, is expected in patients requiring this procedure.

As discussed above, vascular access for dialysis may include a point for fluid communication into the bloodstream of a patient, such as a dialysis patient, so that the patient can be properly connected to the dialysis machine. Without this vascular access point, repeated dialysis would not be possible without the troublesome use of venous catheters or the like. Generally speaking, an AV fistula 300 may be created internally and used for prolonged period of time. The most direct AV fistula creation involves a surgical procedure to put a lumen 312 of an artery 304 into direct fluid communication with a lumen 314 of a vein 306, and allowing arterial blood, as indicated by arrows 316, to flow directly into the vein 306 as shown in FIG. 55A. The blood vessels of the arm are usually chosen e.g. at the wrist/forearm 318 or in the upper arm 319 of a patient. Due to the arterial pressure, the vein 306 which makes up an AV fistula graft or is disposed downstream of an AV fistula typically increases in size and the walls of the vein would also thicken over time (not shown). Generally, it takes about 4 to 8 weeks for the AV fistula vein to mature and strengthen to a useable level suitable for dialysis access by needles. A pair of needles may then be inserted into this enlarged and strengthened vein 306 to allow blood flow through the vein 306, indicated by arrows 317, to flow through the dialyzer using a blood pump on the dialyzer machine. For some treatment embodiments, it may be desirable for a transverse dimension or diameter of the enlarged and strengthened AV fistula vein to expand to about 10 mm.

In addition to the creation of an AV fistula 300 by means of directly connecting an artery 304 to a vein 306, an AVG 302 may be created, as discussed above, which is an artificial blood vessel used to join an inner lumen 312 of an artery 304 into fluid communication with an inner lumen 314 of a vein 306 as shown in FIG. 55. Such an AVG 302 may be used in some cases when the patient's own blood vessels are too small for direct AV fistula construction. The AVG 302, which may be either straight or looped, is typically disposed close to the surface of the skin of the patient for ease of needle access for dialysis or the like. The AVG 302 may be formed from an artificial material such as PTFE or the like, or the AVG 302 may be an autologous graft obtained from the patient's own body e.g. a sacrificial vein taken from the patient's thigh or any other suitable location. AVGs 302 are most commonly placed in the upper arm 319, lower arm 318 or thigh. Two to four weeks are typically allowed to pass before the AVG 302 is suitable for vascular access use. The two to four week delay may allow adequate time post-operative for healing and sufficient growth of tissue to stabilize the AVG.

Figure 56:
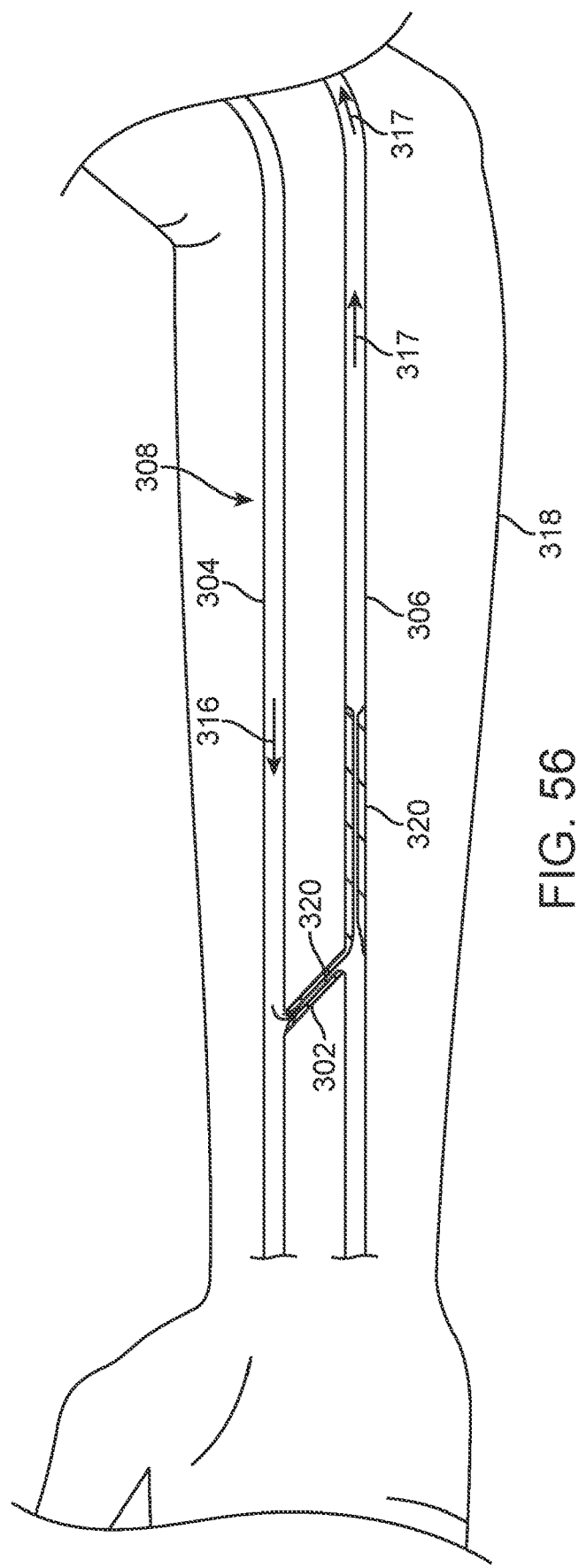
FIG. 56 shows the arteriovenous fistula embodiment of FIG. 5 with a blockage embodiment disposed within the arteriovenous fistula and the vein adjacent the arteriovenous fistula.
Figure 57:
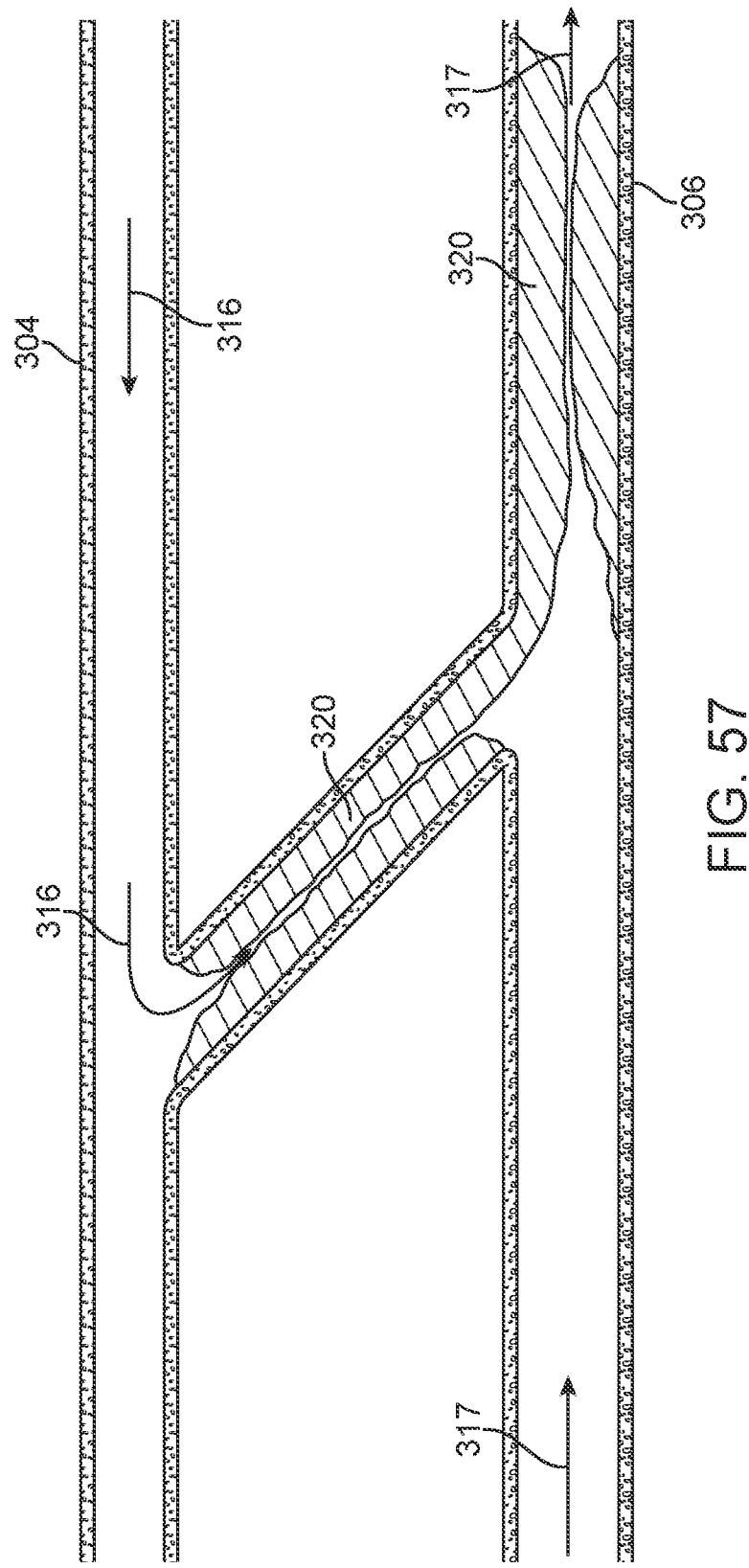
FIG. 57 is an enlarged view of the blockage embodiment of FIG. 56.

Notwithstanding the common use of AV fistulas 300, vascular access still represents the Achilles heel in today's hemodialysis treatment. In some patients the vessels are unsuitable for primary arteriovenous fistula creation. Thrombosis is also a leading cause of AV fistula failure as well as intimal thickening, leading to stenosis by means of cellular proliferation. Enhanced cellular proliferation in human stenotic tissue derived from AV fistulas 300 results in high proliferation rates associated with endothelial cell coverage of the lumen and low local flow velocities due to blockages 320 as shown in FIGS. 56 and 57. In particular, problems with blockages 320 in AV fistulas 300 typically occur at the junction of the vein 306 with the artery 304. The incidence of stenosis in the first postoperative year may be 50% to 60% in hemodialysis AV fistulas 300 when constructed with the use of AVGs 302. AVG failure usually occurs within 18 months from creation of the associated AV fistula 300. One problem with AV fistulas 300 is the continuing narrowing of the AV fistula 300 over time especially at the juncture of the artery 304 with the vein 306. Vascular muscle cells begin growing inwardly causing thrombosis in the AV fistula 300 and/or adjacent vessels such as the vein 306. When this thrombus becomes large, blood flow 317 decreases and the AV fistula 300 ceases to be effective.

Non-surgical options for treating this narrowing condition of AV fistulas 300 is primarily balloon angioplasty type procedures which just remolds the hyperplasia but does not remove the material and therefore, may not improve the blood flow characteristics through the AV fistula 300 over time. In particular percutaneous transluminal balloon angioplasty (PTA) of blockages 320 of AV fistulas 300 and adjacent vessels typically requires high pressure up to 30 atmospheres (atm) balloons to fully dilate the occluded vessel of the AVG 302 or adjacent vessel. Stenting, drug coated stents and photodynamic therapy have been proposed to treat stenosed or otherwise blocked AV fistulas 300. Blood thinning therapy may also used to minimize thrombosis in an AV fistula 300, although none of these treatment methods are particularly effective for long term treatment. However, the type of blockage 320 present in the AV fistula 300 and adjacent vessels appears to be similar to the type of blockage seen in an in-stent restenosis (ISR) and therefore, a combination of laser ablation and drug eluting balloon (DEB) therapy may be more effective for treatment yielding long term patency of a lumen of an AV fistula 300 and/or vessels adjacent to the AV fistula 300.

Pulsed UV ablation at 308 nm is effective in ablating neointimal hyperplasia as well as thrombus. Pulsed UV laser energy may be used for treating blockages 116 in coronary and peripheral arteries 119 for both de nova and restenosed lesions as shown in FIGS. 28-36 and discussed above. In addition, recent Food and Drug Administration (FDA) approval has been granted for the use of UV laser energy ablation of blockage material for treating in-stent restenosis (ISR). Recently published results for ISR have shown that such blockages are different than de nova plaque in that such blockages are made up mostly of neointimal hyperplasia. The mechanism of ISR lesions appears to be due to smooth muscle cell replication and accumulation of extracellular matrix. The extracellular matrix is composed of various collagen subtypes and proteoglycans and over time constitutes the major component of the mature restenotic plaque. Such extracellular matrix material does not appear to be susceptible to treatment by standard PTA, because the material of these type of restenosis lesions contains a large amount of water and the blockage material acts like a sponge which absorbs the water giving a blockage material much of its volume. Compression of the blockage material from the force exerted by an expanded angioplasty balloon squeezes the water out of the blockage material but water is then rapidly reabsorbed by the blockage material following a balloon dilatation by PTA. The reabsorption of the water by the blockage material results in re-expansion of the blockage material into the lumen of the patient's vessel and thereby reoccludes the vessel. As such, the long term results for treatment of ISR with PTA seems to be very poor. Furthermore, PTA with the use of drug-eluting balloons (DEB) coated for example with paclitaxel-iopromide mixture has been shown to improve the long term outcome in the treatment of de nova type lesions or blockages, but these methods have not fared as well when used to treat the plaque formed by ISR. The best results for thus far for treating ISR have been achieved with methods that include debulking of the blockage material of the ISR with laser ablation followed by DEB treatment.

To improve flow in AV fistulas, AVGs and vessels adjacent thereto which have narrowed or been occluded, in some cases, we propose using some or any of the embodiments discussed or incorporated herein of pulsed XeCl 308 nm short pulsed excimer lasers coupled with a liquid core ablation catheter having a solid output window (as discussed above) to ablate the blockage 320 which may include thrombosis and/or cellular plaque in order to treat the point of vascular access provided by an AV fistula. See commonly owned U.S. patent publication no. 2013-0096545, filed Oct. 12, 2012, now U.S. Pat. No. 9,700,655, issued Jul. 11, 2017, which is incorporated by reference herein in its entirety. Optionally, the treatment of AV fistulas 300, AVGs, and adjacent vessels by laser ablation may be combined with subsequent treatment with DEB. The liquid core ablation catheter 22 may also be configured to emit a red aiming beam from a distal end thereof to help visualize and guide the distal end of the ablation catheter 22 inside the patient's vasculature 308. Pulsed excimer laser atherectomy at 308 nm may be used to remove obstructions 320 in vessel lumens by photo dissociation, which may remove the material of the blockage 320 and produces patent circular lumens without thermal damage to the vessel wall.

For UV ablation of an AV fistula blockage 320, a shorter catheter can be used than that required to treat coronary vessels because the AV fistula 300 is typically formed in the wrist region 318 or upper arm 319. Thus, the recanalization procedure for laser ablation may be performed using vascular access directly into the vein 306 in the arm instead of entering through the groin as for coronary and peripheral arterial atherectomy. Because there is not a need to go around tight curves, a multilayer catheter 22 or 22' without a braided layer 52 (as shown in FIG. 13) can be used in most instances.

If the blockage 320 of a lumen of an AV fistula lesion is a total occlusion, guidance for the laser ablation catheter 22 may be a support catheter 26, 26' or 26", with the support catheter being either straight, tapered or angled at a distal section thereof as shown in FIGS. 20 and 21. In some cases, a deflectable tip support catheter 322 (as shown in FIG. 62) may be used to position the distal tip 34 of the ablation catheter 22 to a desired treatment site within a patient's vasculature 308. For non-total occlusions a UV liquid core ablation catheter 22' with a rapid exchange eccentric guide wire lumen 58 (see FIGS. 16 and 26) that may be used to keep the ablation catheter 22' coaxial to a vessel being treated and also to guide the distal tip 34 of the laser ablation catheter 22' within an AVG 302 from the artery 304 to the vein 306. An introducer sheath 323 (see FIG. 58) may also be inserted into the patient's vasculature 308 with a distal end 324 thereof disposed adjacent the occluded vessel followed by a guiding devices such as a support catheter and/or guidewire 56 passed through the introducer sheath 323. The distal tip 324 of the laser ablation catheter 22 is positioned to clear the blockage 320. In some cases, a patent AV fistula vein may have a diameter of about 10 mm, but the ablation catheter 22 might only about 1.5 mm to about 2.1 mm for some embodiments.

In order to ablate a lumen having a transverse inner dimension which is larger than a transverse outer dimension of the ablation catheter 22, an angled tip 57 of a support catheter 26' can be used to produce a larger lumen as shown in FIGS. 24, 25 and 33-36. A deflectable tip 324 of the deflectable tip support catheter 322, as shown in FIG. 62, may be used in a manner similar to the angled tip 57' of support catheter 26' shown in FIGS. 21 and 36. That is, the ablation catheter 22 may be axially advanced through an inner lumen of the tubular deflectable tip catheter 322 until the distal end 34 of the laser ablation catheter extends slightly from a distal end of the deflectable tip catheter 322. Thereafter, the distal tip 324 of the deflectable tip catheter 322 may be transversely deflected so as to transversely displace the distal tip 34 of the ablation catheter prior and during axial advancement of the laser catheter 22 and during ablation of the blockage 320. The transverse displacement of the distal tip 34 of the ablation catheter 22 during axial advancement of subsequent ablation passes results in the ablation of material of the blockage 320 that is transversely adjacent the previous lumen made by previous ablation passes. The distal end 324 of the deflectable tip catheter 322 can be either deflected, rotated or both. A deflected deflectable tip 324 of deflectable tip catheter 322 may be used to hold the distal end 34 of the laser ablation catheter 22 in a transversely displaced position during axial advancement or to provide nutation of the distal tip 34 as discussed with regard to FIGS. 23-25 and 36.

The deflectable tip 324 may be deflected by a deflection angle, indicated by arrow 326, of up to at least about 45 degrees. The deflectable tip 324 may also have an axial length, indicated by arrow 328, of about 2 mm to about 4 mm. Deflection of the deflectable distal tip 324 may be controlled by a knob 330 on a proximal handle portion 332 of the deflectable tip catheter 322. Recent clinical studies, however, have shown that all the plaque of a blockage need not be removed when followed by a DEB to achieve long term patency. Use of either a guidewire 56 or deflectable tip support catheter 322, or any other suitable support catheter 26', can position the laser catheter ablation tip 34 at the proper position for contact ablation of the blockage 320. Typically, PTA procedures for treating stenosed AV fistulas may use a 7 French (2.3 mm diameter) support catheter.

Some embodiments of a method of treating an AV fistula 300 of a patient may include inserting an introducer sheath 323 into a patient's vasculature 308 as shown in FIG. 58 to provide a conduit from a position outside the patient's body to a position within the patient's body. A guiding device such as a guidewire 56 or support catheter 26' or 322 may then be advanced to the AV fistula and a liquid core ablation catheter 22 or 22' then advanced through an inner lumen of the introducer sheath 323 and to a position adjacent a blockage 320. Such a blockage 320 may be disposed within or adjacent the AV fistula 300. During advancement, the distal end 34 of the liquid core ablation catheter 22 or 22' may be guided with the guiding device. In some cases, the guiding device includes a guidewire 56 and guiding the distal end 34 of the liquid core ablation catheter 22', as indicated by arrow 321, includes advancing the liquid core ablation catheter 22' over the guidewire 56 as shown in FIG. 59 with the guidewire 56 disposed within a guidewire lumen 58 as shown in FIG. 15. For some embodiments, the liquid core ablation catheter 22 may include an eccentric guidewire lumen 58 with a distal end of the eccentric guidewire lumen 58 being disposed adjacent the distal end 34 of the liquid core ablation catheter 22'. Such an eccentric guidewire lumen 58 may have an axial length of at least about 10 cm. For such embodiments, axially advancing the liquid core ablation catheter 22' may further include axially advancing the liquid core ablation catheter 22' over the guidewire 56 disposed within such an eccentric guidewire lumen 58.

Figure 60:
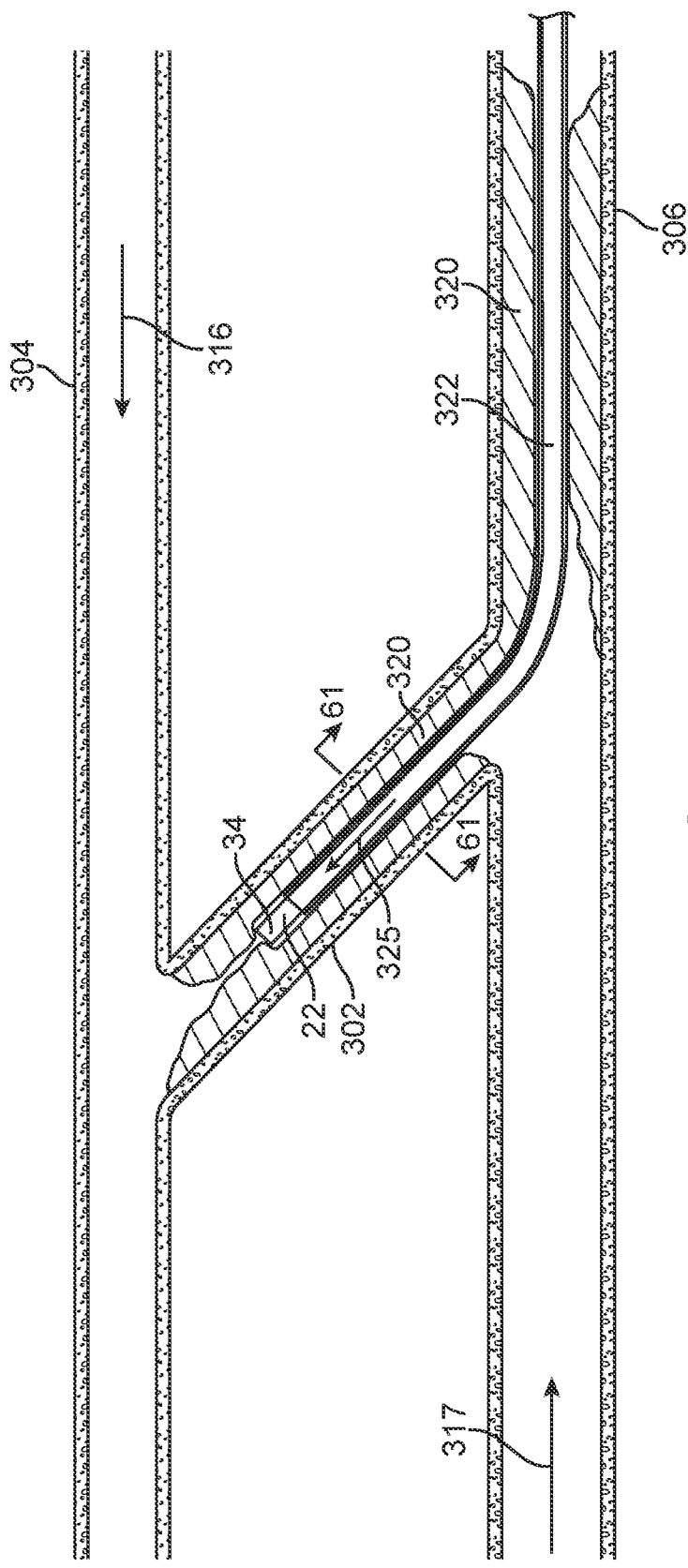
FIG. 60 illustrates the laser ablation catheter of FIG. 58 being guided by a support catheter and axially advanced through the blockage while emitting pulsed ultraviolet laser ablation energy from a distal end of the liquid core ablation catheter and ablating and debulking the blockage.
Figure 61:
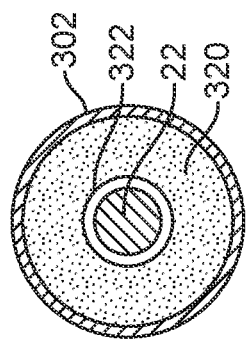
FIG. 61 is a view of the arteriovenous fistula, the blockage, the ablation catheter embodiment and the support catheter of FIG. 60 in transverse cross section taken along lines 61-61 of FIG. 60.

In other embodiments, the guiding device may include a support catheter 322 and guiding the distal end 34 of the liquid core ablation catheter 22 comprises advancing a distal end 34 of the liquid core ablation catheter 22 from a distal end 324 of the support catheter 322 as shown in FIG. 60. For method embodiments that include guiding with a support catheter 26', 322 or the like, the distal tip 34 of the laser ablation catheter 22 may be extended by a distance of up to about 5 mm from the distal end 324 of the support catheter 322. For some method embodiments, the distal end 34 of the ablation catheter 22 may be advanced, as indicated by arrow 325 in FIG. 60, and guided by advancing a distal end 324 of the liquid core ablation catheter 22 from a distal end 324 of the support catheter 322 up to about 5 mm from the distal end 324 of the support catheter 322 then axially advancing the support catheter 322 relative to the liquid core ablation catheter 22 while holding the liquid core ablation catheter 22 stationary. The support catheter 322 may be advanced until the distal end 324 of the support catheter 322 is disposed substantially evenly with the distal end 34 of the laser ablation catheter 22. The laser ablation catheter 22 may then be advanced relative to the support catheter 322 for a distance up to about 5 mm, and then this process repeated at least one additional time. In some cases, this step and repeat process may be continued until the blockage of the AV fistula is completely traversed by the laser ablation catheter 22. This step and repeat process may be the same as, or similar to the process shown in FIGS. 28-32 and discussed above.

For some method embodiments, a distal portion of the liquid core ablation catheter 22 may include a radiopaque marker 31 and a distal tip 324 of the support catheter 322 may include a radiopaque marker 334. For such an embodiment, guiding the distal end 34 of the liquid core ablation catheter 22 may be performed using the radiopaque markers 31 and 334 under fluoroscopy to visualize and identify an axial position of each of the support catheter 322 and liquid core ablation catheter 22 relative to each other while emitting pulsed ultraviolet laser ablation energy from the distal end 34 of the liquid core ablation catheter 22. In certain instances, red light (not shown) may be emitted from a red diode laser and from the distal surface 42 of the distal end 34 of the liquid core ablation catheter 22 and a position of the distal end 34 of the liquid core ablation catheter 22 visualized through skin of the patient by visualizing the red light through the skin of the patient.

Figure 17:
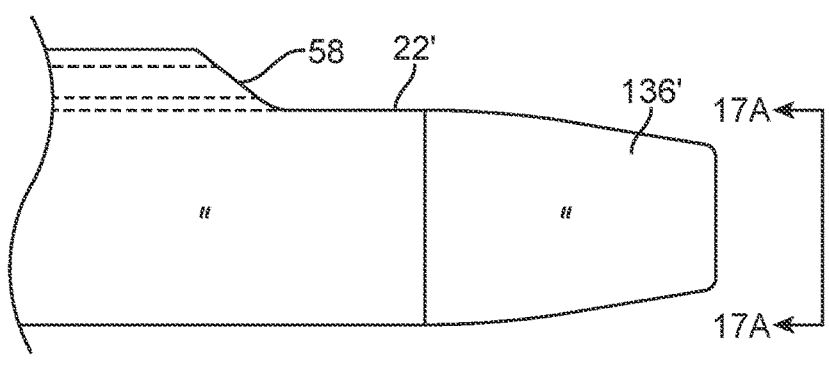
FIG. 17 is an elevation view of a distal portion of an embodiment of the liquid core ablation catheter embodiment of FIG. 15 having a tapered metal housing disposed at a distal end thereof.
Figure 17A:
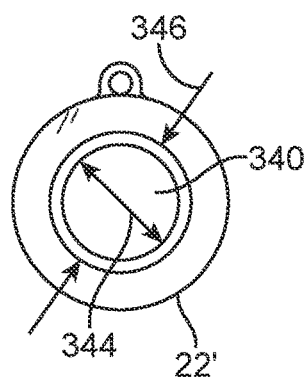
FIG. 17A is an end view of the distal end of the liquid core ablation catheter of FIG. 17.
Figure 63:
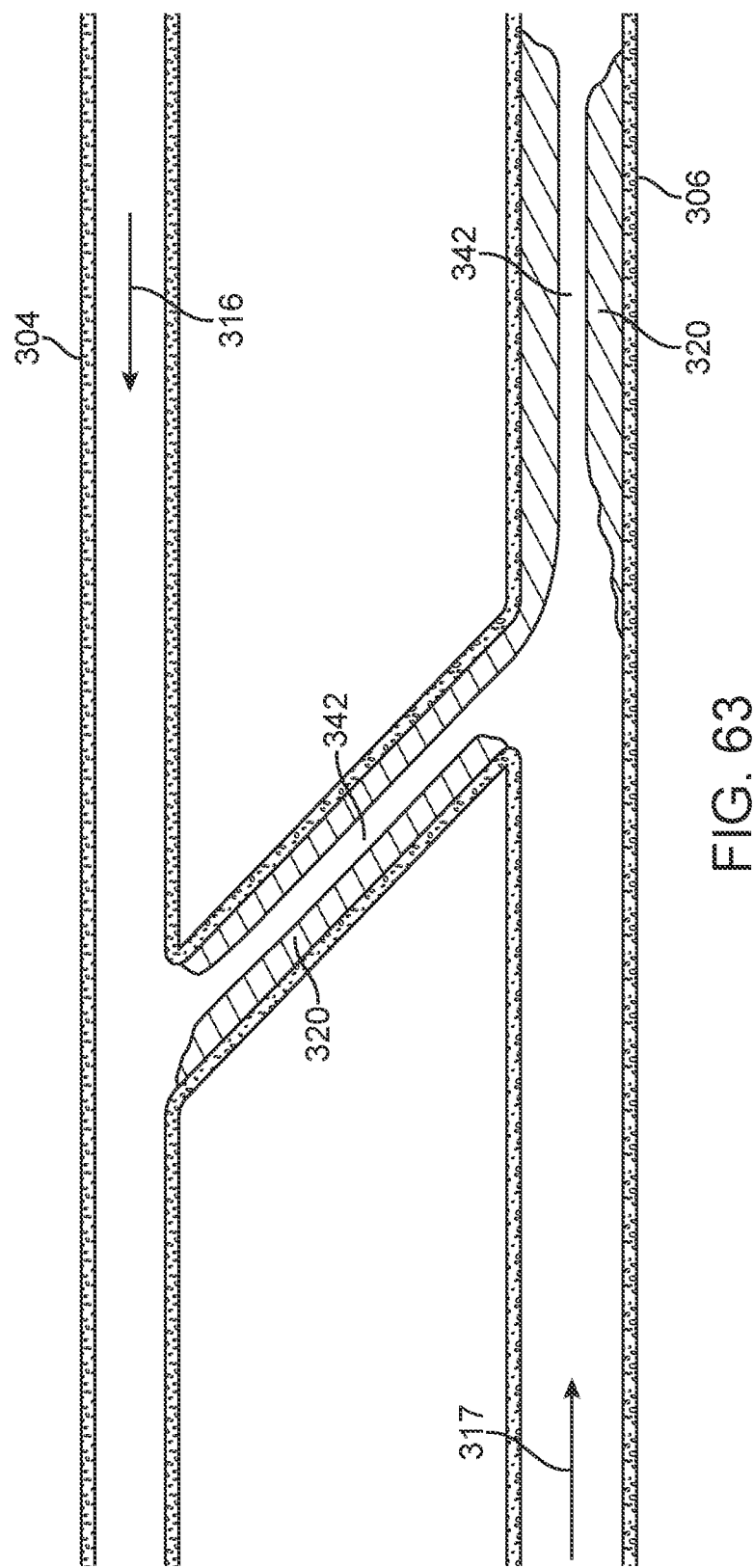
FIG. 63 shows the enlarged view of the arteriovenous fistula of FIG. 57 after ablation and debulking of the blockage by the ablation catheter embodiment as shown in FIG. 59 or 60.

While being guided by a guidewire 56, support catheter 26' or 322, or any other suitable guiding device, the liquid core ablation catheter 22 or 22' may be advanced through the blockage while emitting pulsed ultraviolet laser ablation energy from a distal surface 42 or 340 (as shown in FIG. 17A) of the liquid core ablation catheter 22 or 22' thereby ablating the blockage 320 and debulking the blockage 320. The liquid core ablation catheter 22 or 22' may continue to be advanced until the blockage 320 is axially traversed by the distal end 34 of the liquid core ablation catheter 22 or 22'. Thereafter, the liquid core ablation catheter 22 or 22' may be axially withdrawn or otherwise removed from the AV fistula vessel or vessels 302, 306, after the blockage 320 has been traversed. A neolumen 342 created by ablating and debulking of the blockage 320 after removal of the liquid core ablation catheter 22 or 22' is shown in FIG. 63.

For some liquid core ablation catheter embodiments 22 or 22' discussed herein, an active emitting surface of a distal end of the liquid core ablation catheter 22 or 22' may include at least about 50 percent of a total area of the distal end of the liquid core ablation catheter 22 or 22'. FIG. 17A shows an end view of a liquid core ablation catheter 22' having an eccentric guidewire lumen 58 and a tapered distal end. The surface area of the active emitting surface 340 indicated by arrow 344 is at least about 50 percent of the total area of the distal end surface of the liquid core ablation catheter 22' as indicated by arrow 346. The inactive dead space surrounding the active emitting area 340 is made up of the surface area of the distal end of the tapered metal tip 110. It should be noted that the active emitting surface 340 of the liquid core ablation catheter 22' shown in FIG. 17A is a continuous, uninterrupted emitting surface within the diameter indicated by arrow 344. A similar ratio of active emitting surface area 42 relative to total surface area at the distal end of the liquid core ablation catheter 22 may also be used in some cases. This continuous, uninterrupted active emitting surface is in contrast to other available ablation catheters that rely on a bundle of multiple fibers or waveguides. Due to the geometry of bundling multiple fibers with round transverse cross sections, there is a predetermined limit on the packing efficiency due to the dead space that does not emit laser ablation energy disposed between adjacent fiber tips. Liquid core ablation catheters 22 or 22' that have a continuous, uninterrupted active emitting surface do not include this dead space between bundled fibers and thus ablate tissue at the distal tip surface for contact ablation more efficiently.

Liquid core ablation catheter embodiments 22 or 22' having a large percentage of active emitting surface 42 or 340 relative to total surface area of the distal end produce more efficient ablation and debulking of blockages being treated. For some embodiments, axially advancing the liquid core ablation catheter 22 or 22' may include axially advancing a liquid core ablation catheter 22 or 22' that has a multilayer tube 38 with a base tube 50 made at least in part of fluorinated material and an inner coating 48 disposed on an inner surface of the base tube 50 (see FIG. 15). Such an inner coating 48 may include a material having a low index of refraction of up to about 1.34 or less, and a biocompatible liquid core 40 which fills an inner lumen 46 within the multilayer tube 38 and which is capable of transmitting pulsed 308 nm ultraviolet high energy pulsed radiation.

In some instances, during ablation and debulking of a blockage 320, pulsed ultraviolet laser ablation energy from a XeCl excimer laser 10 at a nominal output wavelength of about 308 nm and a repetition rate of less than about 100 Hz may be directed into an input end of the liquid core ablation catheter 22 or 22'. The pulsed ultraviolet laser ablation energy is then transmitted through the ablation catheter 22 or 22' and emitted from the active emitting surface 42 or 340 of the liquid core ablation catheter 22 or 22'. In some instances, emitting pulsed ultraviolet laser ablation energy includes emitting pulsed ultraviolet laser ablation energy at a pulsed energy fluence greater than a threshold of ablation of a type of blockage material 320 being ablated from a laser source 10 of the laser ablation energy comprising a XeCl pulsed 308 nm excimer laser with a pulse duration of less than about 100 nsec, and a repetition rate of less than about 100 Hz.

Figure 64:
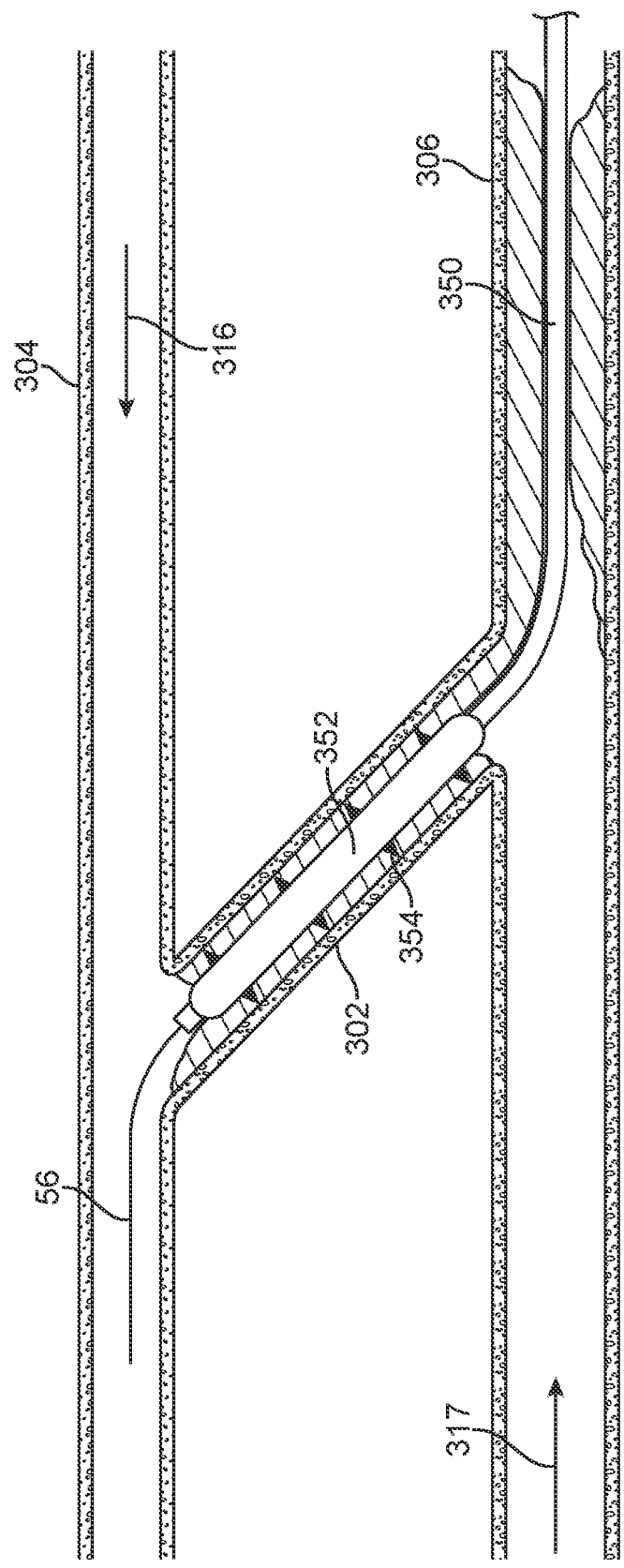
FIG. 64 shows the enlarged view of the arteriovenous fistula of FIG. 57 during treatment of the blockage in the arteriovenous fistula by a drug eluting angioplasty balloon embodiment.
Figure 65:
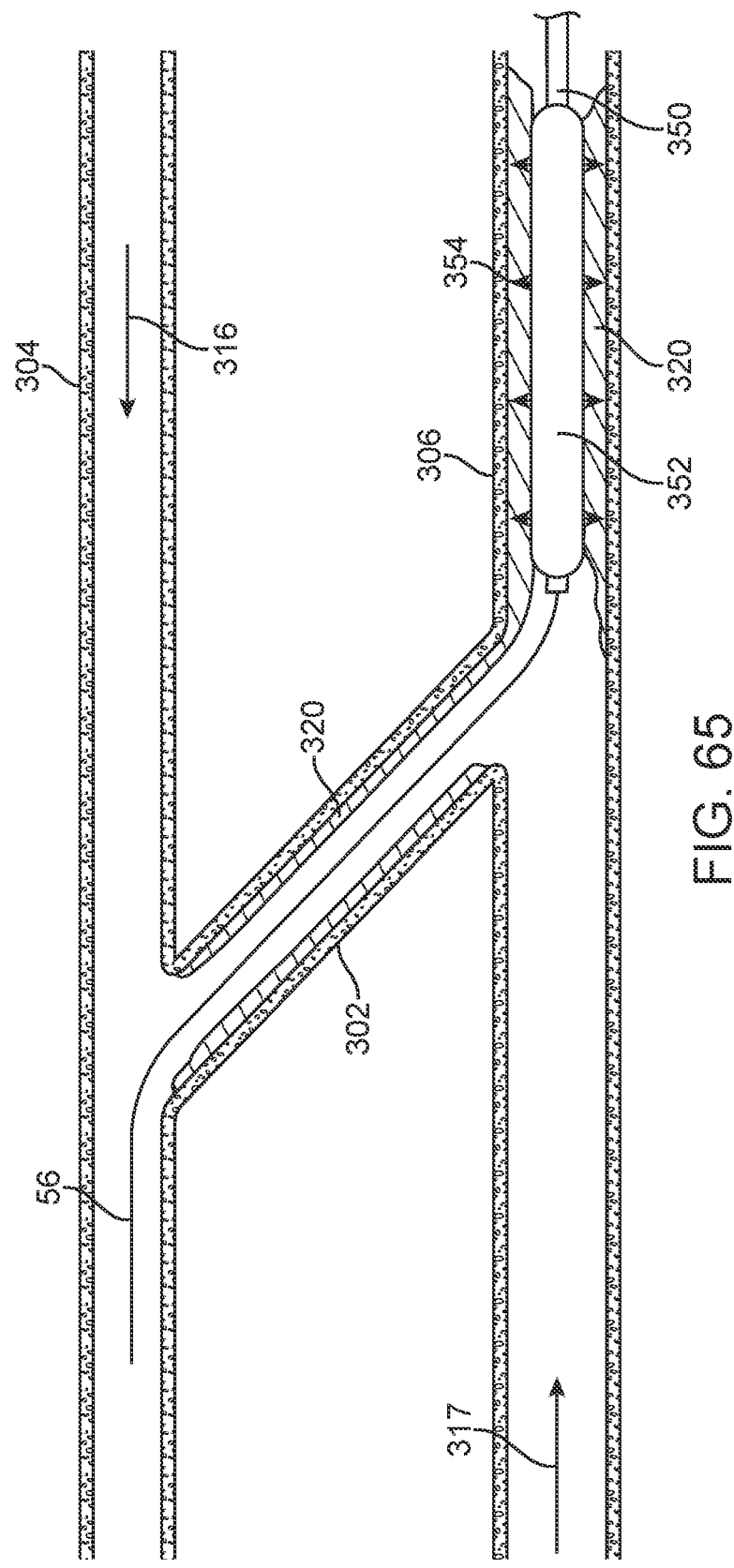
FIG. 65 shows the enlarged view of the arteriovenous fistula of FIG. 57 during treatment of the blockage in the vein adjacent the arteriovenous fistula by a drug eluting angioplasty balloon embodiment.
Figure 66:
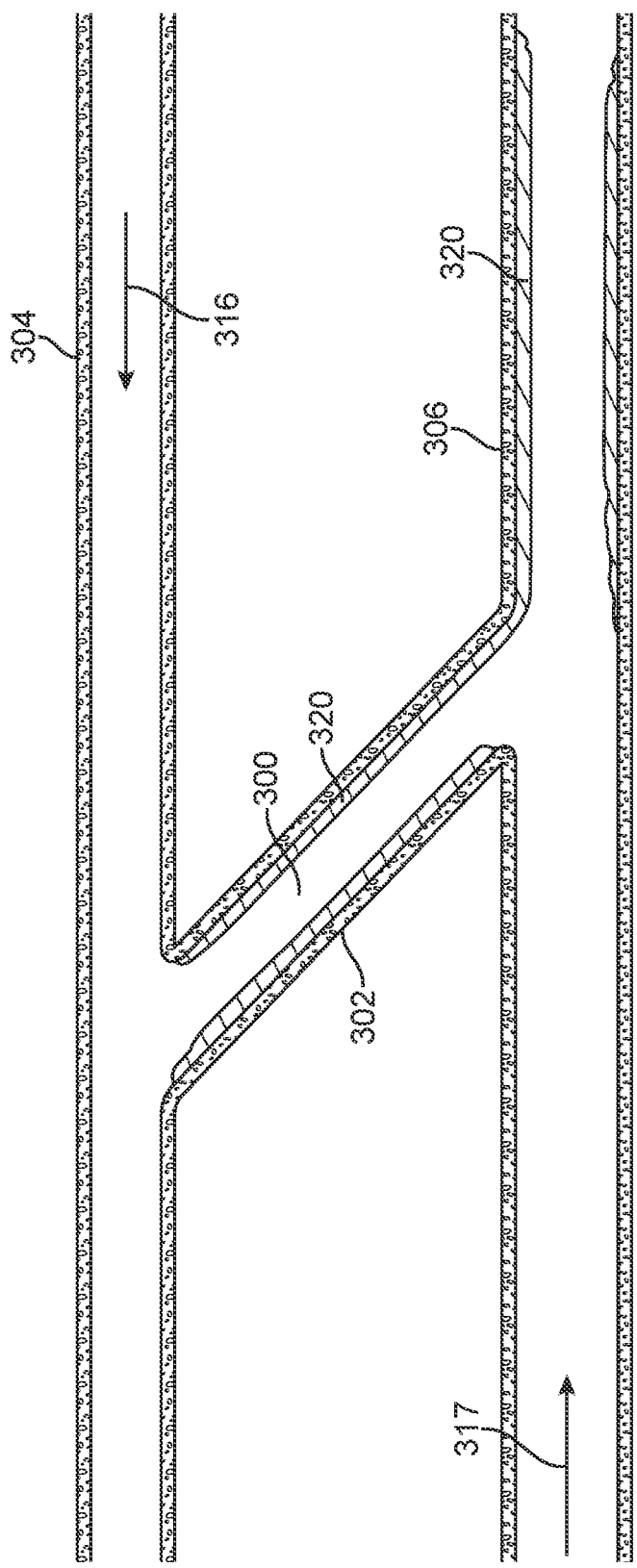
FIG. 66 illustrates a patent lumen through the blockage shown in FIG. 57 after treatment of the arteriovenous fistula.

Once the blockage 320 has been completely traversed, the AV fistula and adjacent vessels, for example, AVG 302 or vein 306, may be further treated by treating the neolumen 342 created by the laser ablation process with a drug eluting balloon catheter 350 as shown in FIGS. 64 and 65 in order to improve long term patency of the neolumen 342. The neolumen 342 for purposes of this step may be any lumen previously crossed and treated by a UV ablation catheter including liquid core ablation catheters 22 or 22' or any other such UV ablation catheters such as a fiber optic based ablation catheter. Such fiber optic based ablation catheters may also include multi-fiber fiber optic ablation catheters (not shown). FIG. 64 shows a blockage 320 disposed within the AVG 302 being treated with a dilated DEB 350. An inflatable balloon 352 of the DEB 350 is configured to expand within the blockage 320 surrounding the balloon 352. As discussed above, when blockages 320 are being treated by PTA alone, it may be necessary to inflate the PTA balloon to high pressures such as up to about 30 atm. However, for treatment embodiments that include laser ablation and debulking of a blockage 320 with subsequent treatment with DEB, the inflatable balloon 352 of the DEB 350 may be fully effective when inflated to lower pressures due to the effects of ablation and debulking of the material of the blockage 320 prior to the DEB treatment. Such lower inflation pressures may have a benefit of generating less mechanical damage to a wall of a vessel being treated which may also minimize injury response mechanisms at the treatment site including subsequent hyperplasia formation. In some cases, an inflatable balloon 352 of a DEB 350 may be inflated to a pressure of up to about 5 atm following ablation and debulking of the same blockage 320.

The balloon 352 is also configured to elute materials such as drugs into tissue of the blockage 320 that surrounds the balloon 352 during inflation as indicated by arrows 354 in FIG. 64. FIG. 65 shows a blockage 320 disposed within a vein 306 adjacent the AV fistula 300 and AVG 302 being treated with a dilated DEB 352. Once again the DEB 352 is shown eluting a drug into the tissue of the blockage 320 which surrounds the DEB 352 as indicated by arrows 354 in FIG. 65. Advancement of the DEB catheter 350 in FIGS. 64 and 65 is carried out with the DEB catheter 350 being advanced to the target treatment site over a guidewire 56. As discussed above, the combination of treating soft spongy blockages with laser ablation and debulking in combination with subsequent treatment by DEB 352 is believed to yield good long term patency results. In some cases, the DEB embodiment 352 may be configured to elute a suitable drug configured to control restenosis following an angioplasty procedure. In some cases, treating the neolumen 342 of the blockage 320 with a drug configured to control restenosis following an angioplasty procedure includes treating the blockage with a compound that includes paclitaxel. For some treatment embodiments, treating the blockage with a compound including paclitaxel includes treating the blockage with a paclitaxel-iopromide mixture.

During advancement of the laser ablation catheter 22 and/or the support catheter 26' or 322, a saline solution or contrast solution may be injected through a lumen disposed between an outside surface of the liquid core ablation catheter 22 and an inside surface of the support catheter 26' or 322 by a syringe 19 as shown in FIG. 58. The contrast or saline solution may thus be emitted from the distal end of the support catheter 26' or 322. In addition, if the support catheter 26' or 32 is introduced through an inner lumen of an introducer sheath 323, saline or contrast solution may be injected through a lumen disposed between an outside surface of the support catheter 26' or 322 and an inside surface of the introducer sheath 323. For this configuration, the saline or contrast solution will be ejected from the distal end of the introducer sheath 323.

As discussed above, for some treatment methods, it may be desirable to form a neolumen 342 in a blockage 320 that has an inner transverse dimension that is larger than an outer transverse dimension of the liquid core ablation catheter 22. For such method embodiments, the distal end 34 of the liquid core ablation catheter 22 may be laterally or transversely repositioned and then axially advanced through the blockage 320 for a second pass after a first ablation and debulking pass with the distal end 34 of the liquid core ablation catheter 22 transversely re-positioned while emitting pulsed ultraviolet laser ablation energy from the distal surface 42 of the liquid core ablation catheter 22. Additional material of the blockage 320 may be thereby ablated and debulked during the second pass with the distal tip 34 of the liquid core ablation catheter 22 so laterally repositioned. In order to maintain the transverse repositioning of the distal end 34 of the liquid core ablation catheter 22 during the second ablation and debulking pass, a support catheter 26' having an angled distal section may be used to transversely re-positioning the distal end of the support catheter 26' while nutating the angled distal section of the support catheter during advancement and ablation. In some instances, a support catheter 32 having a deflectable distal section or tip 324 may be used such as shown in FIG. 62. For such an embodiment, the distal end 34 of the liquid core ablation catheter 22 may be transversely re-positioned during a second pass while ablating and debulking the blockage 320 while transversely deflecting the deflectable distal section 324 of the support catheter 322 and thus the distal end 34 of the liquid core ablation catheter 22 which extends slightly therefrom. For any of the method embodiments discussed above, it may be desirable to deploy a filter device downstream (with regard to direction of blood flow) from a blockage 320 being treated in order to capture any thrombus or other blockage material 320 which is removed from a blockage 320 but which is not ablated.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

Certain embodiments of the technology are set forth in the claim(s) that follow(s).

What is claimed is:

1. A liquid core ablation catheter, comprising:
   a multi-layer catheter tube comprising:
      a base layer tube comprising a fluoropolymer material,
      an internal coating disposed on an inner surface of the base layer tube, the internal coating including an index of refraction,
      an outer layer disposed on an outer surface of the base layer tube;
   a first solid window that seals the inner lumen at a first end of the multi-layer catheter tube;
   a second solid window that seals the inner lumen at a second end of the multi-layer catheter tube; and
   a core liquid disposed within and completely filling the inner lumen of the multi-layer catheter tube, the core liquid including an index of refraction which is higher than the index of refraction of the internal coating and with the outer layer including a material that is impervious to diffusion of the core liquid.

2. The liquid core ablation catheter of claim 1 wherein the material of the outer layer that is impervious to diffusion of the core liquid comprises polychlorotrifluoroethylene.

3. The liquid core ablation catheter of claim 1 wherein the fluoropolymer material of the catheter tube comprises fluorinated ethylene propylene.

4. The liquid core ablation catheter of claim 1 further comprising a braided layer disposed over an outer surface of the base layer tube.

5. The liquid core ablation catheter of claim 1 wherein the internal coating on the inner surface of the base layer tube comprises an amorphous fluoropolymer.

6. The liquid core ablation catheter of claim 1 wherein the internal coating disposed on the inner surface of the base layer tube comprises a low index of refraction of less than about 1.34.

7. The liquid core ablation catheter of claim 1 wherein the base layer tube comprises a material that is impervious to diffusion of the core liquid disposed within the inner lumen of the multi-layer catheter tube.

8. The liquid core ablation catheter of claim 7 wherein the material of the base layer tube that is impervious to diffusion of the core liquid comprises polychlorotrifluoroethylene.

9. The liquid core ablation catheter of claim 1 wherein each of the first solid window and the second solid window comprises ultraviolet grade silica.

* * * * *